United States Patent
Matsumoto et al.

(10) Patent No.: US 6,218,135 B1
(45) Date of Patent: Apr. 17, 2001

(54) 1,2-DIOXETANE DERIVATIVE

(75) Inventors: Masakatsu Matsumoto, 4-8-1-509, Araisono, Sagamihara-shi, Kanagawa 228-0825; Nobuko Watanabe, Kamakura, both of (JP)

(73) Assignee: Masakatsu Matsumoto, Sagamihara (JP)

( * ) Notice: Subject to any disclaimer, the term of this patent is extended or adjusted under 35 U.S.C. 154(b) by 0 days.

(21) Appl. No.: 09/267,604

(22) Filed: Mar. 15, 1999

(30) Foreign Application Priority Data

Mar. 13, 1998 (JP) .................................................. 10-080518
Mar. 13, 1998 (JP) .................................................. 10-080519
Mar. 13, 1998 (JP) .................................................. 10-080520

(51) Int. Cl.⁷ ...................... G01N 33/535; G01N 33/542; C07D 307/04; C07D 413/14; C07D 417/14

(52) U.S. Cl. ...................... 435/7.91; 436/537; 436/805; 544/148; 548/159; 548/217; 549/58; 549/435

(58) Field of Search .................. 549/435, 58; 548/159, 548/217; 544/148; 435/7.91; 436/537, 805

(56) References Cited

FOREIGN PATENT DOCUMENTS 0 779 293 A1  6/1997 (EP) .

*Primary Examiner*—Mary E. Ceperley
(74) *Attorney, Agent, or Firm*—Connolly Bove Lodge & Hutz

(57) ABSTRACT

The present invention has its objects to provide a compound not only which is easy to handle, thermally stable, and high in emission efficiency, but also which can show high emission efficiency without coexisting enhancer in the system even in a protic solvent.

The present invention is related to a 1,2-dioxetane derivative of general formula (I).

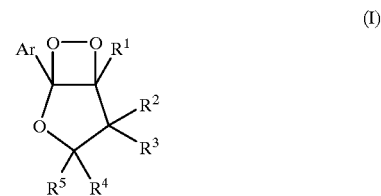

[wherein $R^1$, $R^2$, $R^3$, $R^4$ and $R^5$ each independently represents hydrogen, alkyl or aryl; a pair of $R^2$ and $R^3$ and a pair of $R^4$ and $R^5$ may respectively be joined to each other to form a cycloalkyl group.

20 Claims, No Drawings

1,2-DIOXETANE DERIVATIVE

TECHNICAL FIELD

This invention relates to novel 1,2-dioxetane derivatives, and more particularly to 1,2-dioxetane derivatives of value as chemiluminescent materials which can be used in immunological assay systems and other uses.

BACKGROUND ART

A variety of 1,2-dioxetane derivatives have so far been synthesized, and it is known that compounds having a spiroadamantyl group in the 3-position are particularly useful chemiluminescent materials (e.g. Japanese Kokai Publication Hei-5-21918 and Japanese Kokai Publication Hei-5-45590).

Furthermore, as compounds synthesized by the present inventors, the compounds disclosed in Japanese Kokai Publications Hei-8-245615, Hei-8-169885, and Hei-8-165287 are known. However, those 1,2-dioxetane derivatives do not have good thermal stability. The Japanese Kokai Publication Hei-9-216887 referred to above discloses a compound with improved thermal stability.

In regard of such 1,2-dioxetane derivatives, much research has been undertaken as inferable from the above list of publications and new compounds have also been created. Therefore, it is necessary for applying to a clinical examination and other fields to have a substance with a good thermal stability, easiness of handling, and high in emission efficiency.

However, those known compounds, e.g. compounds described in Japanese Kokai Publication Hei-9-216887 have the drawback that their chemiluminescent emission efficiencies are considerably sacrificed in the presence of protic solvents. Therefore, when used in immunoassays in a clinical examination, for instance, those compounds failed to give a practically useful intensity of emission when the assay system includes a protic solvent. Therefore, it is necessary to have a substance capable of increasing the intensity of emission, the so-called enhancer, to coexist in the system. Therefore, a compound showing high emission efficiency without coexisting enhancer in the system even in a protic solvent is more available.

Furthermore, in a clinical examination performed using an automatic instrument, for instance, compounds differing in emission wavelength from the conventional chemiluminescent materials should be of great use, for the detection and determination of a plurality of test items can be simultaneously performed. Moreover, if the difference in color be of the order which can be visually detected, such compounds should be of great convenience and are expected to find application in a variety of uses.

SUMMARY OF THE INVENTION

In view of the above state of the art, the present invention has for its object to provide a compound which is easy to handle, thermally stable, and high in emission efficiency.

Further, the present invention has for its object to provide a compound not only which is easy to handle, thermally stable, and high in emission efficiency, but also which has a different wavelength from conventional 1,2-dioxetane derivatives' (400 to 500 nm), emission of which can be identified with conventional derivatives' with equipments, and which can be identified with conventional derivatives visually.

Furthermore, the present invention has for its object to provide a compound not only which is easy to handle, thermally stable, and high in emission efficiency, but also which can show high emission efficiency without coexisting enhancer in the system even in a protic solvent.

The present invention is related to a 1,2-dioxetane derivative of general formula (I).

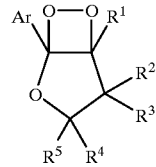

(I)

[wherein $R^1$, $R^2$, $R^3$, $R^4$ and $R^5$ each independently represents hydrogen, alkyl or aryl; a pair of $R^2$ and $R^3$ and a pair of $R^4$ and $R^5$ may respectively be joined to each other to form a cycloalkyl group; Ar represents a group of formula (A)

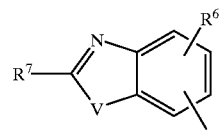

(A)

($R^6$ represents hydroxyl, alkoxyl, aralkyloxy, —OSi($R^8R^9R^{10}$) (where $R^8$, $R^9$ and $R^{10}$ each independently represents alkyl) or a phosphate group; $R^7$ represents hydrogen, alkyl, aryl, hydroxyl, alkoxyl, aryloxy or aralkyloxy; V represents oxygen or sulfur), formula (B)

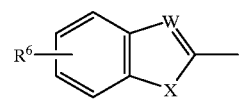

(B)

(wherein $R^6$ is the same as in formula (A); W represents nitrogen or C—$R^{11}$ (where $R^{11}$ represents hydrogen, alkyl, alkoxyl, aryl or aralkyloxy); X represents oxygen or sulfur), or formula (C)

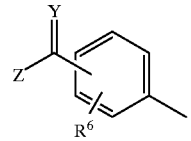

(C)

(wherein $R^6$ is the same as in formula (A); Y represents oxygen, sulfur or N—$R^{12}$; Z represents hydrogen, alkyl, aryl, $OR^{13}$, $SR^{14}$ or a group of the formula;

$R^{12}$ represents hydrogen, alkyl, aryl, hydroxyl, or alkoxyl group. $R^{13}$, $R^{14}$, $R^{15}$ and $R^{16}$ each independently represents hydrogen, alkyl or aryl; a pair of $R^{12}$ and $R^{13}$, a pair of $R^{12}$ and $R^{14}$, a pair of $R^{12}$ and $R^{15}$, and a pair of $R^{15}$ and $R^{16}$ may respectively be joined to each other to form a ring, which ring may contain 2 or more hetero-atoms)].

DETAILED DESCRIPTION OF THE INVENTION

As the term is used in this specification, "alkyl" includes but is not limited to straight-chain and branched-chain alkyl groups each containing 1 to 20 carbon atoms, such as methyl, ethyl, propyl, butyl, pentyl, hexyl, heptyl, octyl, nonyl, decyl, undecyl, dodecyl, tetradecyl, pentadecyl, hexadecyl, heptadecyl, octadecyl, nonadecyl, eicosanyl, etc. and groups formed as the above-mentioned groups are bound to each other in a branching manner in suitable combinations. Those alkyl groups may have one or more substituent groups.

The substituent group mentioned above includes but is not limited to hydroxyl, alkoxyl, and aryl. The alkoxyl mentioned above includes but is not limited to the alkoxyl groups formed as 1 to 5 alkoxy groups each containing 1 to 20 carbon atoms, such as methoxy, ethoxy, propoxy, butoxy, pentyloxy, hexyloxy, methoxyethoxy, methoxypropoxy, ethoxyethoxy, ethoxypropoxy, methoxyethoxyethoxy, etc., are bound together in a linear fashion or in a branched fashion. The aryl group mentioned above includes but is not limited to aromatic hydrocarbon groups each containing 6 to 20 carbon atoms such as phenyl, naphthyl, etc. and heteroaryl groups each containing 1 to 5 nitrogen, oxygen or sulfur atoms as ring atoms, such as furyl, thienyl, pyridyl, and so on.

As the term is used in this specification, "alkoxyl" includes the same alkoxyl groups as the above-mentioned alkoxyl groups with which said alkyl may be optionally substituted.

Further in this specification, "aryl" includes the same aryl groups as the above-mentioned aryl groups with which said alkyl may be optionally substituted.

As the term is used in this specification, "aralkyloxy" means an aralkyloxy group of 7 to 20 carbon atoms, such as benzyloxy, phenethyloxy, etc.

As the term is used in this specification "halogen" includes fluorine, chlorine and bromine, etc.

Referring to the above general formula (I), Ar is preferably a group of formula (a):

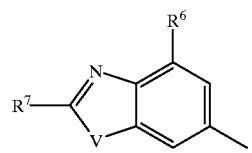

(a)

[$R^6$, $R^7$, and V are as defined in the formula (A)], formula (b):

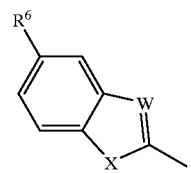

(b)

[$R^6$, W and X are as defined in the formula (B)], or formula (c):

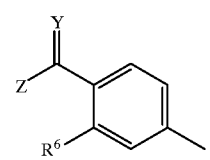

(c)

[$R^6$, Y and Z are as defined in the formula (C)].

Referring, further, to the above general formula (I), $R^1$, $R^2$ and $R^3$ each is preferably alkyl, more preferably alkyl of 1 to 4 carbon atoms, and $R^4$ and $R^5$ each is preferably hydrogen.

When Ar in general formula (I) represents a group of the above formula (C), preferably Y is oxygen and Z is a group of the following formula,

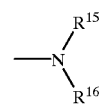

wherein a pair of $R^{15}$ and $R^{16}$ is joined to each other to form a 3- through 7-membered ring. More preferably, Z is a ring of the following formula.

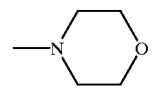

When Ar in the general formula (I) represents a group of the above formula (C), preferably Y is N—$R^{12}$, Z is O$R^{13}$, and a pair of $R^{12}$ and $R^{13}$ is joined to each other to form a 3- through 7-membered ring. More preferably, $R^{12}$ and $R^{13}$ taken together represents a ring of the following formula.

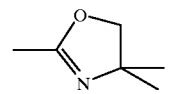

The 1,2-dioxetane derivative of general formula (I), the compound of the invention, can be produced from a dihydrofuran ring derivative having an aryl group substituted by $R^{61}$, which can be represented by the following general formula (II).

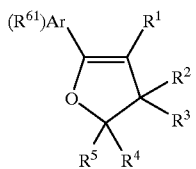

[wherein $R^1$ to $R^5$ are as defined in the general formula (I); $R^{61}$ represents alkoxyl or aralkyloxy; $(R^{61})Ar$ is a group of formula (A')

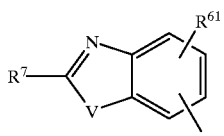

[$R^7$ and V are as defined in formula (A)], formula (B')

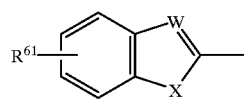

[W and X are as defined in formula (B)] or formula (C')

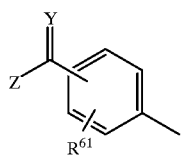

[Y and Z are as defined in formula (C)].

Starting with the compound of the above general formula (II), the compound of the invention, i.e. the 1,2-dioxetane derivative of general formula (I), can be produced in accordance with the following reaction schema.

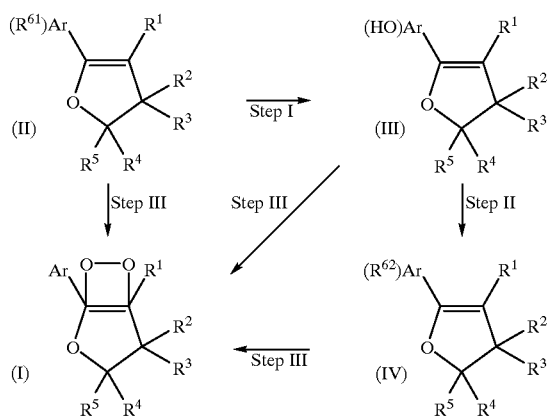

[wherein $R^1$ to $R^5$ and $R^{61}$ are as defined above; $R^{62}$ represents —OSi;$(R^8R^9R^{10})$ (where $R^8$, $R^9$ and $R^{10}$ are as defined above) or a phosphate group of the formula

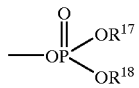

[wherein $R^{17}$ and $R^{18}$ each is alkyl or a pair of $R^{17}$ and $R^{18}$ may be joined to each other to form a ring]. The (HO)Ar in general formula (III) has OH group in the same position as the substituent $R^{61}$ in general formula (II) and the $(R^{62})Ar$ in general formula (IV) has $R^{62}$ in the same position as the substituent $R^{61}$ in general formula (II)].

Step I

In this step, the compound of general formula (II) is deprotected to give the compound of general formula (III).

The compound to be used in this deprotection reaction is a compound of the above general formula (II) [wherein $R^{61}$ is a hydroxy-protecting group (preferably methoxy or benzyloxy)]. This reaction can be carried out by the procedure well known to one skilled in the art, i.e. by using an alkylthiol anion or by hydrogenolysis, and which of such deprotection procedures to be selected is dependent on the kind of group to be deprotected.

Step II

In this step, the above compound of general formula (III) is reacted with a halotrialkylsilane or a halophosphate to introduce the corresponding silyloxy or phosphate group and thereby give the compound of general formula (IV).

For example, when chloroethylene phosphate is used for introducing a phosphate group in this step, the resulting compound can be first converted to the cyanoethyl phosphate sodium salt using sodium cyanide and, then, the cyanoethyl group be eliminated to give the ammonium sodium salt. This ammonium sodium salt can be reacted with sodium hydrogen carbonate or the like to give the disodium salt in an efficient manner.

Step III

In this step, the compound of general formula (II), (III) or (IV) is reacted with singlet oxygen to give the 1,2-dioxetane derivative of general formula (I), i.e. the compound of the invention.

This reaction with singlet oxygen can be effected by irradiating the dihydrofuran derivative of the general formula (II), (III) or (IV) with visible light in the presence of a photosensitizer, such as methylene blue, Rose Bengal, tetraphenylporphyrin (TPP) or the like, in an oxygen atmosphere.

The solvent which can be used for this reaction includes but is not limited to halogenated hydrocarbons such as dichloromethane, dichloroethane, carbon tetrachloride, etc. and alcohols such as methanol and ethanol. This reaction is preferably conducted at −80° C. through room temperature.

There is no particular limitation on the method for the production of said dihydrofuran ring derivative of general formula (II). For example, the following processes can be mentioned.

(1) When $(R^{61})Ar$ is a group of formula (A'):

When $(R^{61})Ar$ in the above general formula (II) is a group of formula (A'), the dihydrofuran ring derivative of general formula (II) can be synthesized in accordance with the following reaction schema.

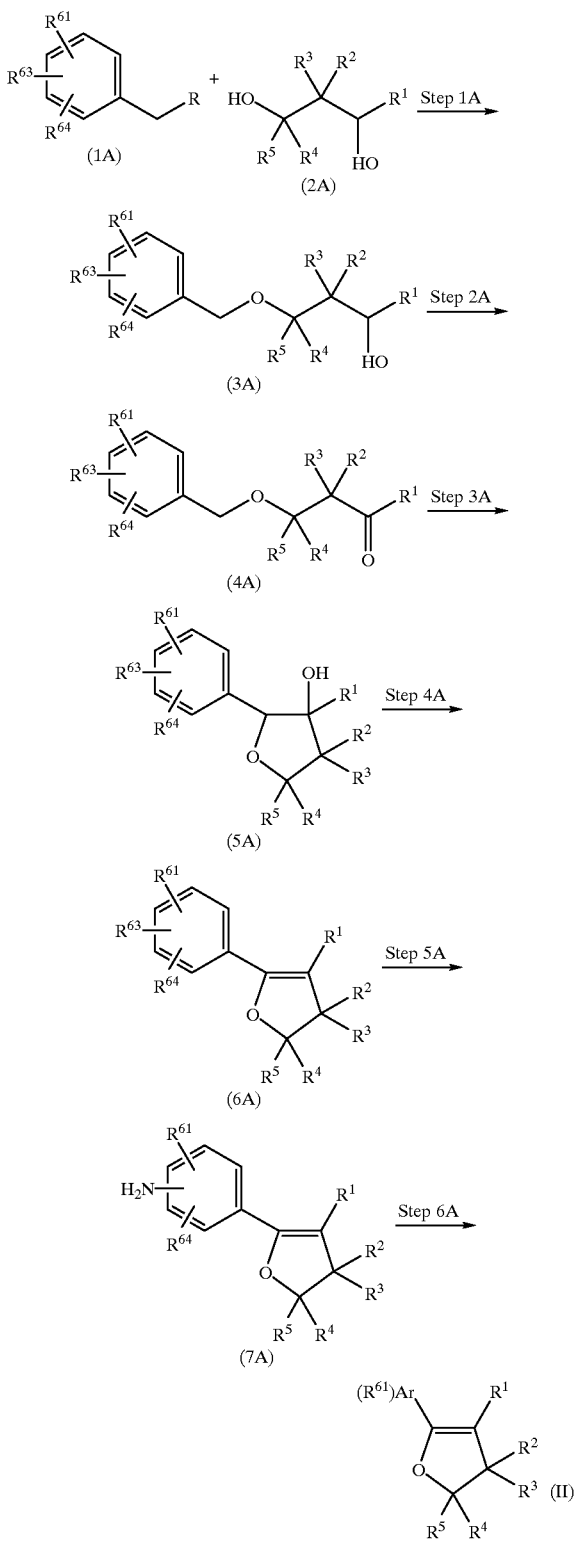

[wherein $R^1$ to $R^5$, and $R^{61}$ are as defined hereinbefore; $R^{63}$ represents halogen; $R^{64}$ represents alkoxyl or aralkyloxy (where $R^{63}$ and $R^{64}$ are respectively joined to the adjacent carbon atom); R represents halogen, substituted sulfonyloxy, or hydroxy; $(R^{61})$Ar the in general formula (II) is a group of formula (A')].

Step 1A

In this step, the compound of general formula (1A) is reacted with the compound of general formula (2A) to give the compound of general formula (3A).

This reaction can be carried out by the method known as Williamson Synthesis.

Here, when the substituent group R of the compound of general formula (1A) is halogen or substituted sulfonyloxy, the compound (1A) is directly submitted to the reaction. When R is hydroxy, R is converted to sulfonyloxy with a tosyl halide or the like within the reaction system and, then, the above reaction is conducted.

Step 2A

In this step, the above compound of general formula (3A) is oxidized to the compound of general formula (4A).

The oxidation reaction in this step can be carried out using a chromium-series oxidizing agent or an activator.

The chromium-series oxidizing agent mentioned above includes but is not limited to pyridinium chlorochromate (PCC) and pyridinium dichrochromate (PDC) and this reaction can be conducted in a halogenated hydrocarbon solvent such as dichloromethane.

When an activator is used, the reaction can be conduced using it in combination with a solvent, for example Py SO$_3$/triethylamine/DMSO, Ac$_2$O/DMSO, etc.

Step 3A

In this step, the above-mentioned compound of general formula (4A) is subjected to cyclization reaction to give the compound of general formula (5A).

This reaction is carried out using a secondary amine salt of lithium, such as lithium diisopropylamide, or a base such as t-butoxypotassium.

The solvent may be an organic solvent such as tetrahydrofuran (THF) or dimethyl sulfoxide (DMSO), and the reaction is preferably conduced at 0° C. through room temperature for 1 to 5 hours.

Step 4A

In this step, the above compound of general formula (5A) is dehydrated to give the compound of general formula (6A).

This reaction is carried out using thionyl chloride in the presence of a base such as pyridine or using an acid such as phosphoric acid, p-toluenesulfonic acid or the like as the catalyst.

The solvent may for example be a halogenated hydrocarbon such as methylene chloride or an aromatic hydrocarbon such as toluene, and the choice is dependent on the reagent to be used.

Step 5A

In this step, the above compound of general formula (6A) is reduced to the compound of general formula (7A).

This step can be carried out by reacting compound (6A) with a lithium salt such as butyllithium, reacting it further with an azide such as p-toluenesulfonyl azide, reducing the reaction product with triphenylphosphine or the like, and causing a thiol such as ethanethiol to act on the reduction product.

The solvent may be an organic solvent such as THF and N,N-dimethylformamide (DMF), and the reaction is preferably carried out under refluxing.

Step 6A

This step comprises synthesizing the compound of the general formula (II) from the compound of the general formula (7A).

In this reaction, $R^{64}$ of the compound of general formula (7A) is converted to hydroxy or SH and, then, an ortho-carboxylate, a carbonylimidazole or the like is reacted to give a condensed-ring structure.

When an ortho-carboxylic acid ester is used, this reaction is preferably conducted under heating at 100 to 200° C. When a carbonylimidazole is used, the reaction is preferably conducted at 0° C. through room temperature.

(2) When $(R^{61})Ar$ is a group of formula (C'):

When, in the above general formula (II), $(R^{61})Ar$ is a group of formula (C'), the dihydrofuran ring derivative of general formula (II) can be synthesized in accordance with the following reaction schema.

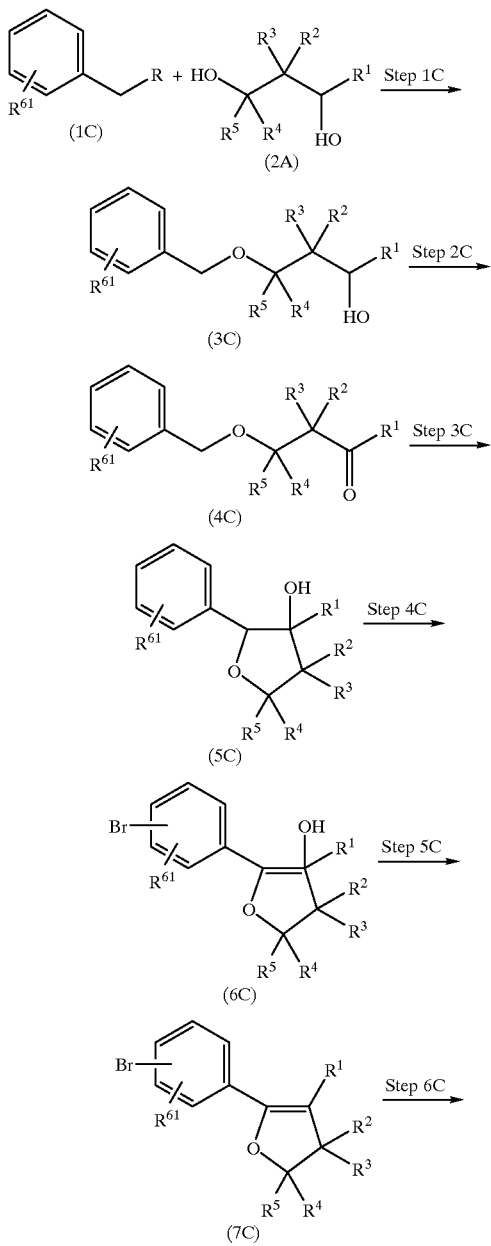

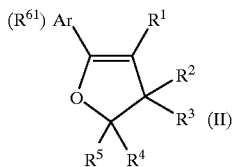

[wherein $R^1$ to $R^5$, $R^{61}$ and R are as defined hereinbefore; $(R^{61})Ar$ in general formula (II) is a group of formula (C')].

Step 1C

In this step, the compound of general formula (1C) is reacted with the compound of general formula (2A) to give the compound of general formula (3C).

The above compound of general formula (2A) is the same compound as that used when $(R^{61})Ar$ is a group of formula (C'), and this 1C step can be carried out by Williamson Synthesis as in said Step 1A.

Step 2C and Step 3C

The production of the compound of general formula (5C) through these steps can be carried out in the same manner as the above-mentioned Step 2A and Step 3A.

Step 4C

In this step, the above compound of general formula (5C) is brominated to give the compound of general formula (6C).

This reaction is carried out using a brominating agent such as N-bromosuccinimide. The solvent may be selected from among such organic solvents as aqueous THF, dioxane and DMF.

Step 5C

This step can be carried out in the same manner as said Step 4A.

Step 6C

In this step, a carboxyl group is first introduced the objective substituent by substituting bromine in the compound of general formula (7C) to give the above compound of the general formula (II).

The introduction of a substituted amino group can be carried out by using a lithium salt such as butyllithium to introduce a carboxyl group and, then, reacting an amine or ammonia in the presence of a condensing agent such as a carbonylimidazole.

For convertion of the amide obtained by the above reaction to the compound having an oxazoline ring, for instance, the reaction can be carried out with a substituted or unsubstituted ethanolamine.

The introduction of an acyl group can be carried out by using a lithium salt such as butyllithium to react with N-methylformanilide or to react aldehyde such as acetaldehyde and benzaldehyde etc. and then, oxidizing hydroxyl group by using an oxidizing agent such as manganese dioxide. In this step, the compounds introduced an acyl group can be used as a starting material of the step III by conducting Step I and reacting with hydroxylamine or alkoxylamine to give an oxime.

(3) When $(R^{61})Ar$ is a group of formula (B'):

When, in the above general formula (II), $(R^{61})Ar$ is a group of formula (B'), the dihydrofuran ring derivative of general formula (II) can be synthesized in accordance with the following reaction schema.

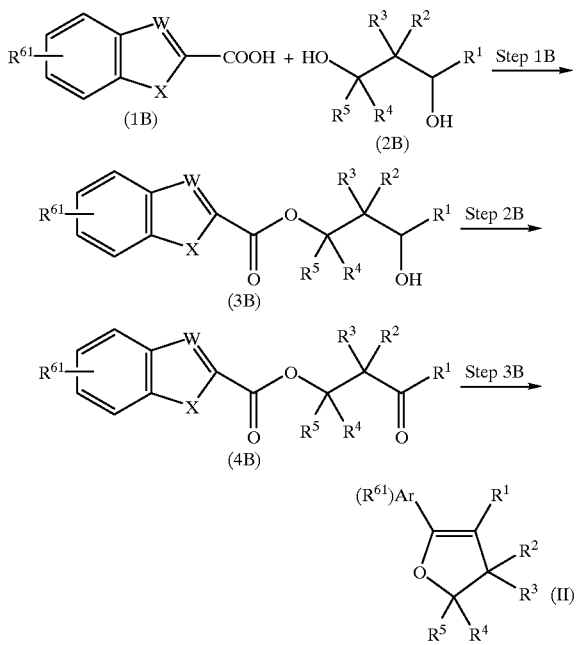

[wherein $R^1$ to $R^5$, W, X and $R^{61}$ are as defined hereinbefore; $(R^{61})Ar$ in general formula (II) is a group of formula (B')]

Step 1B

In this step, the compound of general formula (1B) and the compound of general formula (2B) are subjected to condensation reaction to give the compound of general formula (3B).

This reaction can be carried out in the presence of a condensing agent which may for example be a carbodiimide or a carbonylimidazole.

In conducting this reaction, a halogenated hydrocarbon such as dichloromethane can be used as the solvent.

Step 2B

This step can be carried out in the same manner as said Step 2A.

Step 3B

In this step, the compound of general formula (4B) is reacted with a reducing agent and a base in the presence of titanium to give the alcohol derivative and then subjected to dehydrative cyclization in the presence of an acid catalyst to give the compound of general formula (II).

It is essential that the first stage of this step be conducted in the presence of titanium. The titanium is preferably a titanium halide such as titanium chloride. To mention a preferred example, the compound (4B) is reduced by using lithium aluminum hydride as the reducing agent and triethylamine or pyridine as the base. This reaction can be carried out in an organic ether such as tetrahydrofuran (THF). While this reaction proceeds at 0 to 100° C., the reflux condition is preferred from the standpoints of easiness of operation and reactivity.

The dehydrative cyclization reaction in the second stage of this step is preferably carried out using PPTS, p-toluenesulfonic acid or the like as the acid catalyst. The reaction solvent may for example be a halogenated hydrocarbon or an aromatic hydrocarbon such as benzene, toluene or xylene.

The 1, 2-dioxetane derivative of general formula (I), i.e. the compound of the invention, decomposes into the carbonyl compound with the emission of a chemiluminescence under alkaline conditions or decomposes with the emission of a chemiluminescence in the presence of an enzyme, e.g. an esterase (carboxylic ester hydrase) such as aryl esterase, acetylcholine esterase, etc. or an acid or alkaline phosphatase. Therefore, it can be used not only as an immunoassay reagent in the immunological assay system for determination of the concentration of a substance to be detected in samples but also in enzyme assays, chemical assays and nucleotide probe method.

The substance to be detected in the above-mentioned immunoassay system is not particularly restricted but includes hormones such as hCG, TSH, LH, etc.; cancer-related substances such as AFP, CEA, etc.; viral antigens such as HIV, HTLV-1, etc., the corresponding antibodies, and nucleic acids (DNA, RNA), among others.

The above-mentioned immunoassay is not particularly restricted. For example, it may comprise a step of coupling said enzyme to a substance having a specific binding affinity for said substance to be detected, mixing it with a sample containing the substance to be detected, and allowing the mixture to react for a predetermined time to let the substance to be detected be coupled to said substance having a binding affinity therefor and a step of determining the amount of said substance having said binding affinity which was either coupled or not coupled. This step of determining the amount of the substance having said specific binding affinity which was either coupled or not coupled is based on the following principle. Thus, as the enzyme reacts with the 1,2-dioxetane derivative of the invention, the intensity of emission from the 1,2-dioxetane derivative increases proportionally with the amount of the enzyme so that the concentration of the substance to be detected can be determined by measuring the intensity of the chemiluminescence.

The immunoassay kit containing the 1,2-dioxetane derivative of the invention and the above-mentioned immunological assay methods using it also fall within the scope of the present invention.

The 1,2-dioxetane derivative of general formula(I), thus the compound of the present invention is capable of showing a steady chemiluminescent emission efficiency with high quantum yields and, in addition, is thermally so stable that decomposition products are not observed at all after some refrigerator storage for a year. Therefore, the determination of chemiluminescence can be conveniently carried out with good efficiency. Thus, the derivative of the invention is useful for clinical examinations, for instance.

Particularly, when the 1,2-dioxetane derivative of the invention has the moiety of the above formula (B), the derivative has high thermal stability and a steady chemiluminescent emission, in addition, its luminescence is shifted toward the longer wavelength side compared with the conventional 1,2-dioxetane derivatives (wavelengths 400 to 500 nm), thus containing a red component, with the result that it can be clearly identified from the conventional luminescence by means of an instrument or even visually. Therefore, by using this derivative in combination with a compound having a different luminescent characteristic, multi-item determinations can be carried out in automatic assays in the clinical examination.

Furthermore, the 1,2-dioxetane derivative of the invention has the moiety of the above formula (C), the derivative has high thermal stability and a steady chemiluminescent emission, in addition, is capable of showing a steady chemiluminescent emission efficiency with high quantum yields in protoic solvents even without the aid of an enhancer. Therefore, when using the 1,2-dioxetane derivative of the invention, the enhancers themselves and the step of adding the enhancers are not required so that waste of time and cost can be avoid.

BEST MODE FOR CARRYING OUT THE INVENTION

The following examples illustrate the present invention in further detail and should by no means be construed as defining the scope of the invention.

Examples 1, 2, 9, 10, and 11 describe the synthesis of the 1,2-dioxetane derivative of the invention where Ar represents a group of formula (A); Examples 3 to 6 describe the synthesis of the 1,2-dioxetane derivative of the invention where Ar represents a group of formula (B); and Examples 7, 8, 12, 13, and 14 describe the synthesis of the 1,2-dioxetane derivative of the invention where Ar represents a group of formula (C).

Reference Example 1

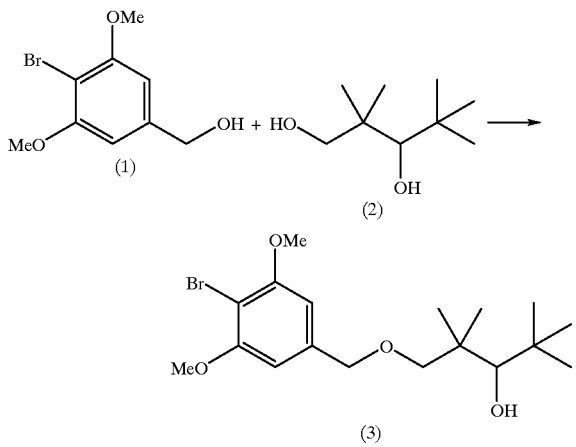

In nitrogen atmosphere at a room temperature, 251 mg (6.28 mmol) of 60% sodium hydride was added to 4 mL of tetrahydrofuran (THF), followed by cooling on ice. To this was added dropwise 603 mg (2.44 mmol) of 4-bromo-3,5-dimethoxybenzyl alcohol (Compound [1]) dissolved in 4 mL of THF. Then, 466 mg (2.45 mmol) of tosyl chloride dissolved in 4 mL of THF was added dropwise. After 30 minutes, 403 mg (2.52 mmol) of 2,2,4,4-tetramethyl-1,3-pentanediol (Compound [2]) dissolved in 4 mL of THF was added dropwise and the mixture was stirred for 5 hours. To this reaction mixture was added 2 mL of pure water, and the mixture was poured in saturated aqueous solution of sodium chloride and extracted with ethyl acetate. The extract was washed with saturated aqueous solution of sodium chloride, dehydrated over anhydrous magnesium sulfate, and concentrated. The concentrate was applied to a silica gel column and the elution was carried out with the mixture of hexane and ethyl acetate (hexane:ethyl acetate =5:1) to obtain 815 mg (2.09 mmol) of 1-(4-bromo-3,5-dimethoxybenzyloxy)-2,2,4,4-tetramethyl-3-pentanol (Compound [3]). Yield 85.9%.

$^1$HNMR(400 MHz, CDCl$_3$); δ1.03 (s, 9H), 1.05 (s, 3H), 1.08 (s, 3H), 3.25 (s, 1H), 3.33 (q$_{AB}$, J=8.1 Hz, 2H), 3.90 (s, 6H), 4.47 (q$_{AB}$, J=12 Hz, 2H), 6.55 (s, 2H) ppm IR (liquid film); 3484, 2955, 1236 cm$^{-1}$ Mass (m/z, %); 390 (M$^+$+1,7), 246(96), 217(14), 151(43), 127(62), 109(22), 97(26), 84(68), 55(100)

Reference Example 2

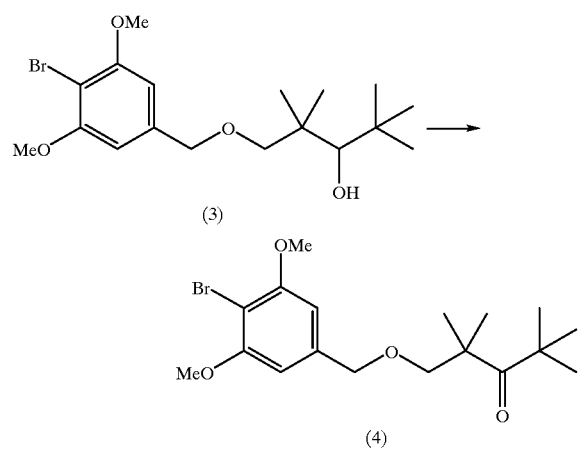

In nitrogen atmosphere at a room temperature, 5 g of Celite was added to 40 mL of methylene chloride, followed by addition of 1.43 g (6.66 mmol) of PCC. Then, 2.34 g (6.05 mmol) of 1-(4-bromo-3,5-dimethoxybenzyloxy)-2,2,4,4-tetramethyl-3-pentanol (Compound [3]) dissolved in 10 mL of methylene chloride was added and the mixture was stirred for 24 hours. Then, 20 mL of 2-propanol and 80 mL of ether were serially added to the above reaction mixture, and filtered with Celite. The filtrate was concentrated and applied to a silica gel column and the elution was carried out with the mixture of hexane and ethyl acetate (hexane:ethyl acetate =10:1) to obtain 2.25 g (5.80 mmol) of 1-(4-bromo-3,5-dimethoxybenzyloxy)-2,2,4,4-tetramethylpentan-3-one (Compound [4]). Yield 95.8%.

$^1$HNMR(400 MHz, CDCl$_3$); δ1.24 (s, 9H), 1.32 (s, 6H), 3.50 (s, 2H), 3.89 (s, 6H), 4.45 (s, 2H), 6.52 (s, 2H) ppm IR (liquid film); 2967, 2869, 1589, 1236 cm$^{-1}$ Mass (m/z, %) ; 388 (M$^+$+1,21), 332(10), 246(39), 231 (100), 151(19), 97(13), 85(15), 69(15), 55(69)

Reference Example 3

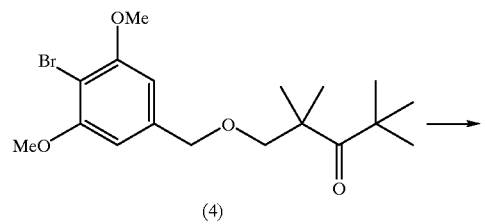

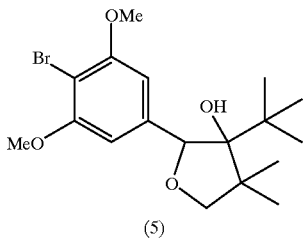

(5)

In nitrogen atmosphere at a room temperature, 2.0 mL (14.2 mmol) of diisopropylamine was added to 15 mL of THF, and after addition of 7.4 mL (11.9 mmol) of 1.6 M butyllithium/hexane, the mixture was stirred for 30 minutes. Then, at −78° C., 4.09 g (10.6 mmol) of 1-(4-bromo-3,5-dimethoxybenzyloxy)-2,2,4,4-tetramethylpentan-3-one (Compound [4]) dissolved in 5 mL of THF was added dropwise and the mixture was stirred for 2 hours. To this reaction mixture was added 10 mL of pure water, and the mixture was poured in 1 M hydrochloric acid and extracted with ethyl acetate. The extract was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=5:1) to obtain 2.39 g (6.18 mmol) of 2-(4-bromo-3,5-dimethoxyphenyl)-3-t-butyl-3-hydroxy-4,4-dimethyl-2,3,4,5-tetrahydrofuran (Compound [5]). Yield 77.4%.
Melting point; 130 to 131° C. (Colorless granular crystals as recrystallized from ether)
$^1$HNMR(400 MHz, CDCl$_3$); δ0.90(s, 9H), 1.21 (s, 3H), 1.38 (s, 3H), 1.92 (s, 1H), 3.81 (q$_{AB}$, J=8.8 Hz, 2H), 3.89 (s, 6H), 4.99 (s, 1H), 6.79 (s, 2H) ppm
IR (KBr); 3482, 2965, 1587, 1232 cm$^{-1}$
Mass (m/z, %) ; 388 (M$^+$+1, 4), 370(25), 355(98), 313(11), 299(42), 246(76), 231(14), 218(14), 55(63)

Reference Example 4

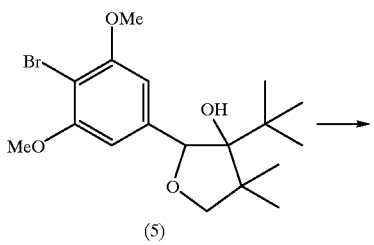

In nitrogen atmosphere at a room temperature, 1.09 g (2.81 mmol) of 2-(4-bromo-3,5-dimethoxyphenyl)-3-t-butyl-3-hydroxy-4,4-dimethyl-2,3,4,5-tetrahydrofuran (Compound [5]) was added to 7 mL of toluene, followed by addition of 34.6 mg (0.18 mmol) of tosyl alcohol, and the mixture was refluxed for 24 hours. This reaction mixture was poured in saturated aqueous solution of sodium chloride and extracted with ethyl acetate. The extract was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate =4:1) to obtain 0.85 g (2.29 mmol) of 5-(4-bromo-3,5-dimethoxyphenyl)-4-t-butyl-3,3-dimethyl-2,3-dihydrofuran (Compound [6]). Yield 81.7%.
Melting point; 139 to 140° C. (colorless granular crystals as recrystallized from ether)
$^1$HNMR(400 MHz, CDCl$_3$); δ1.08 (s, 9H), 1.34 (s, 6H), 3.89 (s, 2H), 3.90 (s, 6H), 6.51 (s, 2H) ppm
IR (KBr);2949, 1651, 1579, 1235 cm$^{-1}$
Mass (m/z, %) ; 370 (M$^+$+1, 25), 353(96), 297(28), 245(24), 218(12), 55(30)

Reference Example 5

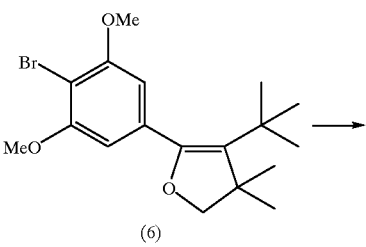

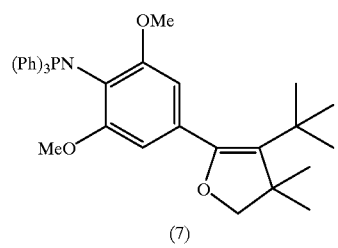

In nitrogen atmosphere at a room temperature, 814 mg (2.21 mmol) of 5-(4-bromo-3,5-dimethoxyphenyl)-4-t-butyl-3,3-dimethyl-2,3-dihydrofuran (Compound [6]) was added to 3 mL of THF. Then, at −78° C., 1.6 mL (2.56 mmol) of 1.6 M butyllithium in hexane was added and the mixture was stirred for 20 minutes. Then, 803 mg (4.07 mmol) of tosyl azide dissolved in 3 mL of THF was added dropwise and the mixture was stirred for 15 minutes. Then, 690 mg (2.63 mmol) of triphenylphosphine and 52.5 mg of rhodium (II) acetate were serially added, followed by stirring for 2 hours. This reaction mixture was poured in a mixture of saturated aqueous solution of sodium chloride and saturated aqueous solution of sodium hydrogen carbonate and extracted with ethyl acetate. The extract was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=10:1) to obtain 882 mg (1.56 mmol) of 4-t-butyl-5-(3,5-dimethoxy-4-triphenylphosphorousiminophenyl)-3,3-dimethyl-2,3-dihydrofuran (Compound [7]) as white solid. Yield 70.9%.
$^1$HNMR(400 MHz, CDCl$_3$); δ1.05 (s, 9H), 1.31 (s, 6H), 3.46 (s, 6H), 3.84 (s, 2H), 6.38 (s, 2H), 7.30–7.80 (m, 15H) ppm
Mass (m/z, %); 303 (M$^+$ 23), 288(100), 258(9), 232(38), 178(42), 150(7), 109(19)

Reference Example 6

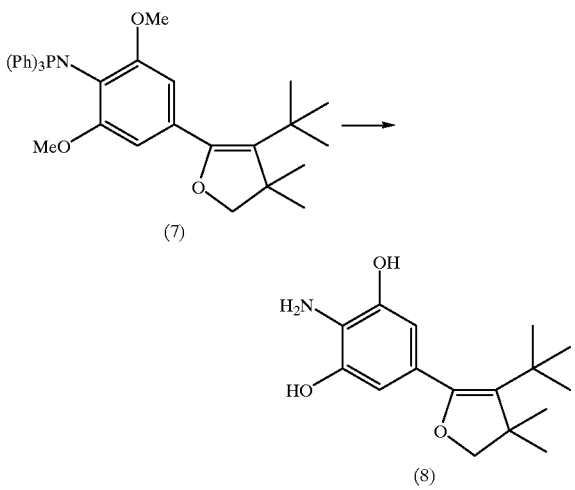

In nitrogen atmosphere, 679 mg (17.0 mmol) of 60% sodium hydride was added to 13 mL of DMF, followed by cooling on ice. Then, ice-cooled 1.2 mL (16.2 mmol) of ethanethiol was added. Thereafter, 876 mg (1.55 mmol) of 4-t-butyl-5-(3,5-dimethoxy-4-triphenylphosphorousiminophenyl)-3,3-dimethyl-2,3-dihydrofuran (Compound [7]) dissolved in 5 mL of DMF was added dropwise and the mixture was refluxed for 3 hours. This reaction mixture was poured in saturated aqueous solution of sodium chloride and extracted with ethyl acetate. The extract was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate =1:1) to obtain 142 mg (0.51 mmol) of 5-(4-amino-3,5-dihydrophenyl)-4-t-butyl-3,3-dimethyl-2,3-dihydrofuran (Compound [8]). Yield 34.2%.

$^1$HNMR(400 MHz, CDCl$_3$); δ1.07 (s, 9H), 1.30 (s, 6H), 3.20–4.00 (Br, 1H), 3.845 (s, 2H), 4.60–5.20 (Br, 1H), 6.36 (s, 2H) ppm

Reference Example 7

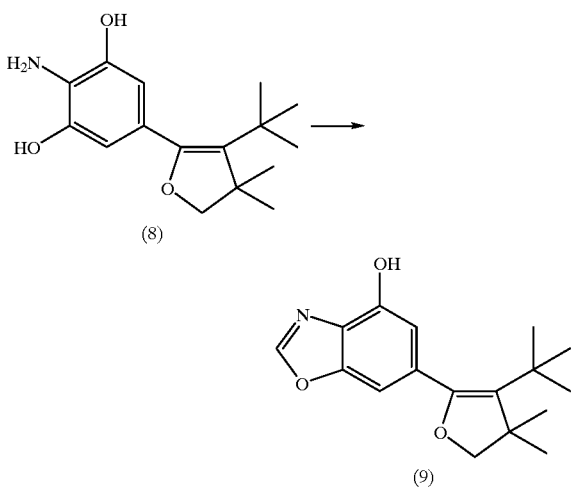

To 3 mL of trimethyl ortho-formate was added 114 mg (0.41 mmol) of 5-(4-amino-3,5-dihydroxyphenyl)-4-t-butyl-3,3-dimethyl-2,3-dihydrofuran (Compound [8]) at a room temperature, and the mixture was refluxed for 12 hours. This reaction mixture was poured in saturated aqueous solution of sodium chloride and extracted with ethyl acetate. The extract was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate =3:1) to obtain 12.3 mg (0.04 mmol) of 4-t-butyl-5-(4-hydroxybenzo[d]oxazol-6-yl)-3,3-dimethyl-2,3-dihydrofuran (Compound [9]) as colorless solid. Yield 10.4%.

$^1$HNMR(400 MHz, CDCl$_3$); δ1.06 (s, 9H), 1.35 (s, 6H), 3.89 (s, 2H), 6.41 (s, 1H), 6.85 (s, 1H), 7.11 (s, 1H), 8.01 (s, 1H) ppm Mass (m/z, %); 287 (M$^+$, 17), 272(64), 216(44), 162(79), 149(35), 134(10), 97(21), 55(100)

Example 1

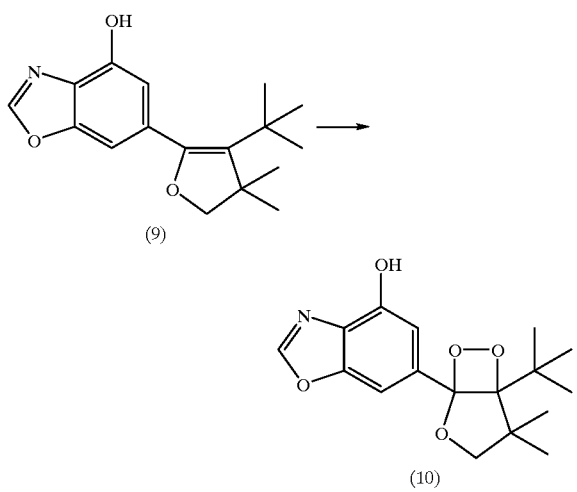

To 1 mL of methylene chloride were added 1.0 mg of tetraphenylporphyrin (TPP) and 12.3 mg (0.04 mmol) of 4-t-butyl-5-(4-hydroxybenzo[d]oxazol-6-yl)-3,3-dimethyl-2,3-dihydrofuran (Compound [9]), and the mixture was externally irradiated with a 940 W sodium lamp in an oxygen atmosphere at −78° C. for 30 minutes. Then, at 0° C., the mixture was externally irradiated with the 940 W sodium lamp for another 15 minutes and, then, concentrated. The residue was subjected to preparative thin-layer chromatography (silica gel 60F$_{254}$) and the elution was carried out with the mixture of hexane and ethyl acetate (hexane:ethyl acetate =5:1) to obtain 10.2 mg (0.03 mmol) of 5-t-butyl-4,4-dimethyl-1-(4-hydroxy-benzo[d]oxazol-6-yl)-2,6,7-trioxabicyclo[3.2.0]heptane (Compound [10]) as white solid. Yield 79.8%.

$^1$HNMR(400 MHz, CDCl$_3$); δ1.01 (s, 9H), 1.17 (s, 3H), 1.41 (s, 3H), 4.22(q$_{AB}$, 8.3 Hz, 2H), 7.19 (s, 1H), 7.51 (s, 1H), 8.14 (s, 1H) ppm Mass (m/z, %); 287 (M$^+$−32, 14), 272(85), 216(7), 162(95), 149(19), 134(9), 97(30), 55(100)

Reference Example 8

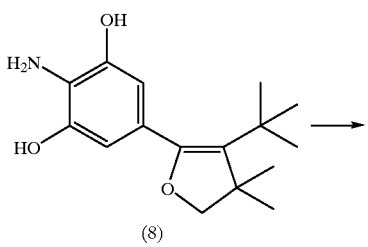

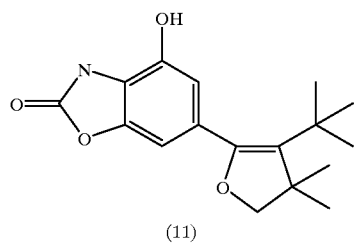

In nitrogen atmosphere at a room temperature, 41.4 mg (0.15 mmol) of 5-(4-amino-3,5-dihydroxyphenyl)-4-t-butyl-3,3-dimethyl-2,3-dihydrofuran (Compound [8]) was added to 1 mL of THF, followed by addition of 31.5 mg (0.19 mmol) of 1,1'-carbonylbis-1H-imidazole. The mixture was stirred for 30 minutes and then concentrated. The concentrate was applied to a silica gel column and the elution was carried out with the mixture of hexane and ethyl acetate (hexane:ethyl acetate=2:1) to obtain 40.3 mg (0.13 mmol) of 4-t-butyl-5-(4-hydroxy-2-oxobenzo[d]oxazol-6-yl)-3,3-dimethyl-2,3-dihydrofuran (Compound [11]) as colorless granular crystals. Yield 88.6%.

$^1$HNMR(400 MHz, CDCl$_3$); δ1.06 (s, 9H), 1.33 (s, 6H), 3.86 (s, 2H), 5.60–6.40 (m, 1H), 6.63 (d, J=1.5 Hz, 1H), 6.79 (d, J=1.5 Hz, 1H), 8.00–8.60 (Br, 1H) ppm Mass (m/z, %); 303 (M$^+$, 23), 288(100), 258(9), 232(38), 178(42), 150(7), 109(19)

Example 2

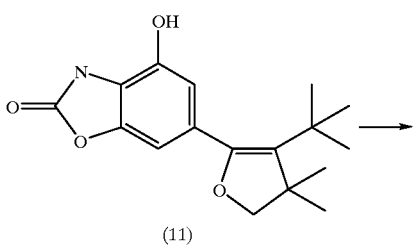

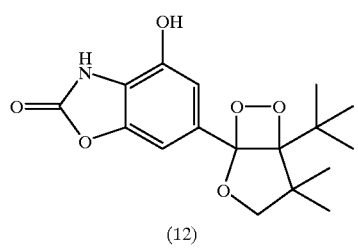

To 1 mL of methylene chloride were added 1.0 mg of TPP and 30.2 mg (0.10 mmol) of 4-t-butyl-5-(4-hydroxy-2-oxobenzo[d]oxazol-6-yl)-3,3-dimethyl-2,3-dihydrofuran (Compound [11]), and the mixture was externally irradiated with a 940 W sodium lamp in an oxygen atmosphere at −78° C. for 1 hour. Then, 2.0 mg of TPP was further added and at 0° C. the reaction mixture was externally irradiated with the 940 W sodium lamp for a further 40 minutes and, then, concentrated. The residue was applied to a silica gel column and the elution was carried out with the mixture of hexane and ethyl acetate (hexane:ethyl acetate=4:1) to obtain 11.7 mg (0.03 mmol) of 5-t-butyl-4,4-dimethyl-1-(4-hydroxy-2-oxobenzo[d]oxazol-6-yl)-2,6,7-trioxabicyclo[3.2.0]heptane (Compound [12]) as white solid. Yield 34.3%.

$^1$HNMR(400 MHz, CDCl$_3$); δ1.00 (s, 9H), 1.15 (s, 3H), 1.36 (s, 3H), 4.18(q$_{AB}$, J=7.3 Hz, 2H), 7.05 (s, 1H), 7.11 (s, 1H) ppm Mass (m/z, %); 335 (M$^+$, 0.2), 303(0.2), 279(17), 195(21), 178(100), 151(6), 123(3), 55(57)

Reference Example 9

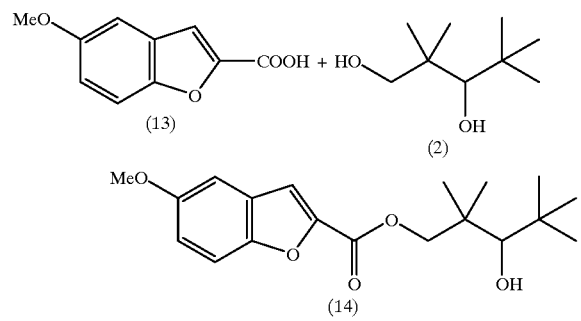

In nitrogen atmosphere at a room temperature, 390 mg (3.19 mmol) of DIMAP was added to 40 ml of methylene chloride containing 2.63 g (13.7 mmol) of 5-methoxybenzofuran-2-carboxylic acid (Compound [13]) and 2.73 g (16.4 mmol) of 2,2,4,4-tetramethyl-1,3-pentandiol (Compound [2]), 50 ml of methylene chloride dissolving 14.20 g (21.9 mmol) of WSC HCl was added dropwise, and the mixture was stirred for 24 hours. Sulfuric acid (1N, 150 ml) was added to the reaction mixture, then the organic layer thereof was washed with saturated aqueous solution of sodium hydroxide, dried with magnesium sulfate anhydride and concentrated. The concentrate was applied to a silica gel column and the elution was carried out with the mixture of hexane and ethyl acetate (hexane:ethyl acetate= 4:1) to obtain 824 mg (2.18 mmol) of 3-hydroxy-2,2,4,4-tetramethylpentane-1-yl 5-methoxybenzofuran-2-carboxylate (Compound [14]). Yield:90.1% melting point 113.5–114.5° C. (colorless needle crystal obtained by recrystallization from the mixture of hexane and ethyl acetate)

$^1$HNMR(400 MHz, CDCl$_3$); δ1.07 (s, 9H), 1.12 (s, 3H), 1.19 (s, 3H), 2.08 (d, J=6.4 Hz, 1H), 3.28 (d, J=6.4 Hz, 1H), 3.86 (s, 3H), 4.25 (q$_{AB}$, J=10.7 Hz, 2H), 7.05–7.08 (m,2H), 7.45–7.49 (m, 2H) ppm IR (KBr); 3543, 2954, 1711, 1552, 1469, 1218 cm$^{-1}$ Mass (m/z, %); 334 (M$^+$ 1), 316(2), 192(92), 175(100), 127(23), 119(20)

Reference Example 10

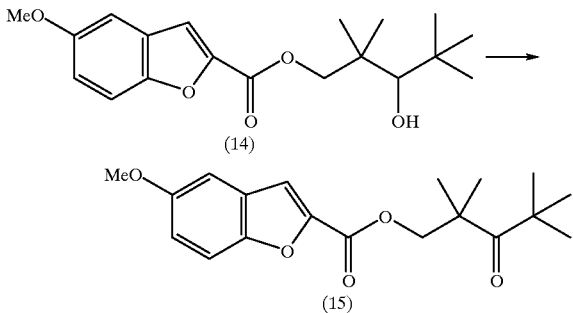

In nitrogen atmosphere at a room temperature, 2.80 mg (13.2 mmol) of PCC and 4.50 g of Celite were suspended with 40 ml of methylene chloride, 25 ml of methylene chloride dissolving 2.90 g (8.68 mmol) of 3-hydroxy-2,2,4,4-tetramethylpentane-1-yl 5-methoxybenzofuran-2-carboxylate (Compound [14]) was added dropwise, and the mixture was stirred for 24 hours. Adding 2 ml of 2-propanol, the reaction mixture was stirred for 1 hour. Then adding 100ml of ether, the resulting mixture was filtrated by Celite and the filtrate was concentrated. The concentrate was applied to a silica gel column and the elution was carried out with the mixture of hexane and ethyl acetate (hexane:ethyl acetate=10:1) to obtain 2.82 g (8.94 mmol) of 2,2,4,4-tetramethyl-3-oxopentane-1-yl 5-methoxybenzofuran-2-carboxylate (Compound [15]). Yield 97.8%.
melting point 81.5–82.5° C. (colorless needle crystal obtained by recrystallization from the mixture of hexane and ethyl acetate)
$^1$HNMR(400 MHz, CDCl$_3$); δ1.30 (s, 9H), 1.39 (s, 6H), 3.85 (s, 3H), 4.44 (s, 2H), 7.06–7.08 (m,2H), 7.35–7.47 (m,2H) ppm
IR (KBr); 2966, 1717, 1567, 1470, 1318, 1215, 1156 cm$^{-1}$
Mass (m/z, %); 332 (M$^+$ 6), 276(20), 192(56), 175(100), 119(14)

Reference Example 11

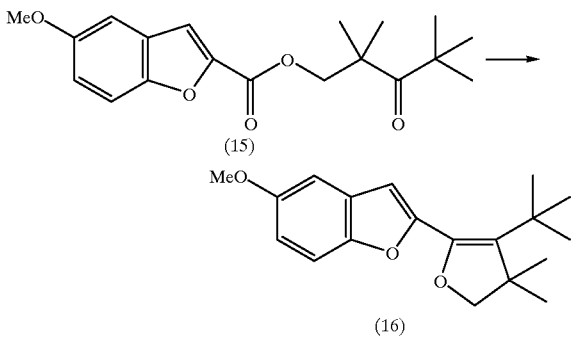

In nitrogen atmosphere, under cooling with ice bath, 6.32 g (41.0 mmol) of titanium chloride was added to 70 ml of THF, the mixture was stirred for 15 minutes. Then adding 770 mg (20.5 mmol) of aluminium lithium hydride, the mixture was stirred for 15 minutes. Adding 2.80 ml (20.5 mmol) of dropwise triethylamine, the mixture was refluxed for 30 minutes. Adding dropwise 20 ml of THF dissolving 970 mg (2.58 mmol) of 2,2,4,4-tetramethyl-3-oxopentane-1-yl 5-methoxybenzofuran-2-carboxylate (Compound [15]), the mixture was refluxed for 2 hours. After standing to cool, a saturated aqueous solution of sodium hydrogencarbonate was added to the mixture and extracted with ethyl acetate. The organic layer was washed with saturated aqueous solution of sodium chloride, then dried with magnesium sulfate anhydride and concentrated. The concentrate (713 mg) was dissolved in 10 ml of methylene chloride and added 75 mg (0.30 mmol) of PPTS, then the mixture was stirred at a room temperature for 24 hours. The reaction mixture was added to a saturated aqueous solution of sodium hydrogencarbonate and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=15:1) to obtain 245 mg (0.711 mmol) of 4-t-butyl-5-(5-methoxybenzofuran-2-yl)-3,3-dimethyl-2,3-dihydrofuran (Compound [16]) as a pale yellow oil. Yield 27.6%.
$^1$HNMR(400 MHz, CDCl$_3$); δ1.26 (s, 9H), 1.33 (s, 6H), 3.84 (s, 3H), 3.91 (s, 2H), 6.76 (s, 1H), 6.89 (dd, J=8.8 and 2.4 Hz, 1H), 7.01 (d, J=2.4 Hz, 1H), 7.38 (d, J=8.8 Hz, 1H) ppm
IR (liquid film);2956, 2867, 1615, 1467, 1205, 1030 cm$^{-1}$
Mass (m/z, %); 300 (M$^+$ 32), 285(100), 229(21), 175(20)

Reference Example 12

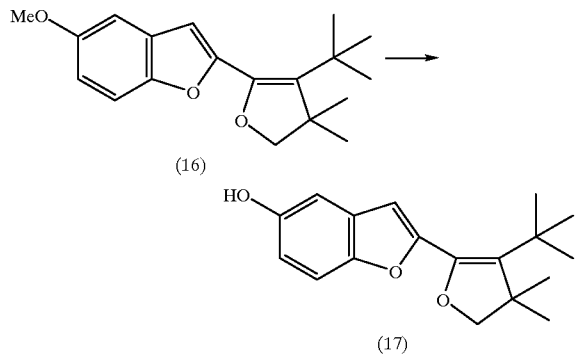

In nitrogen atmosphere, under cooling with ice bath, 110 mg (2.75 mmol) of 60% sodium hydride was added to 3 ml of DMF. Adding 0.30 ml (4.1 mmol) of ethanethiol, the mixture was stirred for 15 minutes. Adding 3.0 ml of DMF dissolving 209 mg (0.608 mmol) of 4-t-butyl-5-(5-methoxybenzofuran-2-yl)-3,3-dimethyl-2,3-dihydrofuran (Compound [16]), the mixture was refluxed for 3 hours. After cooling the reaction mixture, the mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 205 mg (0.592 mmol) of 4-t-butyl-5-(5-hydroxybenzofuran-2-yl)-3,3-dimethyl-2,3-dihydrofuran (Compound [17]). Yield 62.0%.
melting point; 129.0–130.0° C. (colorless granular crystal obtained by recrystallization from the mixture of hexane and ethyl acetate)
$^1$HNMR(400 MHz, CDCl$_3$); δ1.26 (s, 9H), 1.33 (s, 6H), 3.90 (s, 2H), 4.60 (s, 1H), 6.72 (s, 1H), 6.79 (dd, J=8.8 and 2.4 Hz, 1H), 6.95 (d, J=2.4 Hz, 1H), 7.33 (d, J=8.8 Hz, 1H) ppm
IR (KBr); 3389, 2963, 1614, 1466, 1203, 1035, 806 cm$^{-1}$
Mass (m/z, %); 286 (M$^+$ 35), 271(100), 215(27), 169(25), 105(8)

Reference Example 13

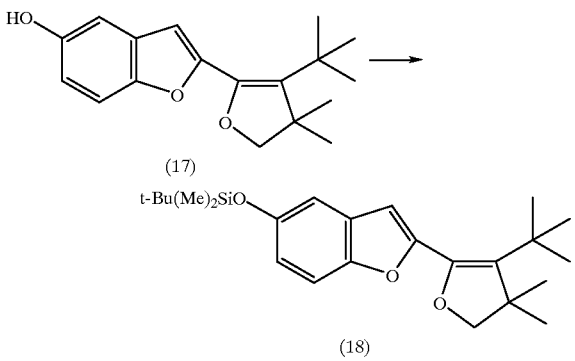

In nitrogen atmosphere, under cooling with ice bath, adding 0.20 ml (1.50 mmol) of triethylamine to 3.0 ml of DMF dissolving 190 mg (0.549 mmol) of 4-t-butyl-5-(5-hydroxybenzofuran-2-yl)-3,3-dimethyl-2,3-dihydrofuran (Compound [17]), the mixture was stirred for 15 minutes. Adding 150 mg of t-butyldimethylchlorosilane (1.00 mmol), the mixture was stirred for 2 hours at a room temperature. The resulting mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate= 5:1) to obtain 225 mg (0.489 mmol) of 4-t-butyl-5-(5-(t-butyldimethylsiloxy)benzofuran-2-yl)-3,3-dimethyl-2,3-dihydrofuran (Compound [18]) as a pale yellow oil. Yield 89.1%.

$^1$HNMR(400 MHz, CDCl$_3$); δ0.19 (s, 6H), 0.99 (s, 9H), 1.27 (s, 9H), 1.33 (s, 6H), 1.39 (t, J=6.8 Hz, 3H), 3.90 (s, 2H), 6.71(s, 1H), 6.78 (dd, J=8.8 and 2.4 Hz, 1H), 6.97 (d, J=2.4 Hz, 1H), 7.31 (d, J=8.8 Hz, 1H) ppm
IR (liquid film); 2956, 2863, 1459, 1255, 1195, 885 cm$^{-1}$
Mass (m/z, %); 400 (M$^+$ 24), 385(100), 343(6), 329(15), 287(10), 73 (59)

Example 3

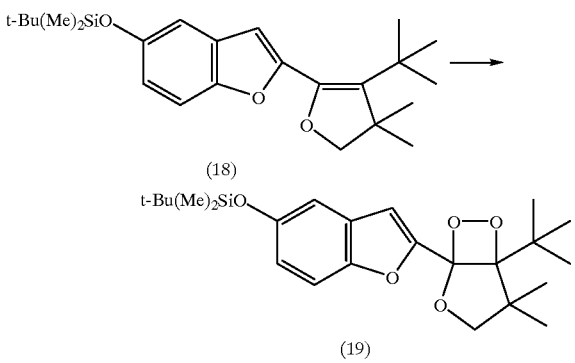

Adding 1 mg of TPP to 4 ml of methylene chloride dissolving 132 mg (0.286 mmol) of 4-t-butyl-5-(5-(t-butyldimethylsiloxy)benzofuran-2-yl)-3,3-dimethyl-2,3-dihydrofuran (Compound [18]), the mixture was stirred in oxygen atmosphere, at the temperature of −78° C. This solution was externally irritated with a 940 W sodium lamp for 4 hours. The reaction mixture was concentrated and fractionated with aliquot thin layer chromatography using the mixture of hexane and ethyl acetate (hexane:ethyl acetate=7:1) to obtain 114 mg of 5-t-butyl-1-(5-(t-butyldimethylsiloxy)benzofuran-2-yl)-4,4-dimethyl-2,6,7-trioxabicyclo[3.2.0]heptane (Compound [19]) as a white solid. Yield 85.0%.

melting point; 117–118° C. (white granular crystal)
$^1$HNMR(400 MHz, CDCl$_3$); δ0.20 (s, 6H), 1.00 (s, 9H), 1.09 (s, 9H), 1.14 (s, 3H), 1.39 (s, 6H), 4.23 (q$_{AB}$, J=8.3 Hz, 2H), 6.84 (dd, J=8.8 and 2.4 Hz, 1H), 6.96 (s, 1H), 7.01 (d, J=2.4 Hz, 1H), 7.36 (d, J=8.8 Hz, 1H) ppm
IR (KBr); 2957, 1466, 1225, 1196, 1034, 873 cm$^{-1}$

Reference Example 14

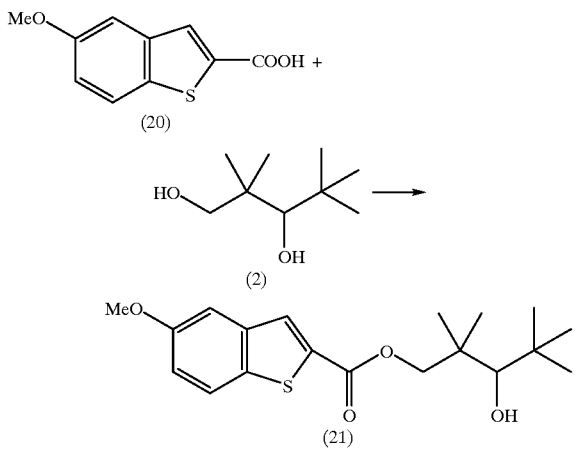

In nitrogen atmosphere at a room temperature, 290 mg (2.37 mg) of DIMAP was added to 10 ml of methylene chloride dissolving 2.02 g (9.71 mmol) of 5-methoxybenzothiophen-2-carboxylic acid (Compound [20]), 2.40 g(15.0 mmol) of 2,2,4,4-tetramethyl-1,3-pentandiol (Compound [2]) and 25 ml of methylene chloride dissolving 13.17 g (16.5 mmol) of WSC.HCl was added dropwise, then the mixture was stirred for 24 hours. The resulting mixture was added to a saturated aqueous solution of ammonium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate= 10:1) to obtain 3.11 mg (8.89 mmol) of 3-hydroxy-2,2,4,4-tetramethylpentane-1-yl 5-methoxybenzothiophen-2-carboxylate (Compound [21]) as a colorless needle crystal. Yield 91.5% melting point; 121.0–122.0° C. (colorless needle crystal obtained by recrystallization from the mixture of hexane and ethyl acetate)
$^1$HNMR(400 MHz, CDCl$_3$); δ1.07 (s, 9H), 1.12 (s, 3H), 1.19 (s, 3H), 1.97 (d, J=6.4 Hz, 1H), 3.29 (d, J=6.4 Hz, 1H), 3.88 (s, 3H), 4.25 (q$_{AB}$, J=10.7 Hz, 2H), 7.07 (dd, J=8.8 and 2.4 Hz, 1H), 7.28 (d, J=2.4 Hz, 1H), 7.73 (d, J=8.8 Hz, 1H), 7.99 (s, 1H) ppm
IR (KBr); 3537, 2960, 1681, 1295, 1154 cm$^{-1}$
Mass (m/z, %); 350 (M$^+$ 1), 332(9), 263(6), 208(87), 191 (100), 165(24), 109(11), 97(15), 69(20)

Reference Example 15

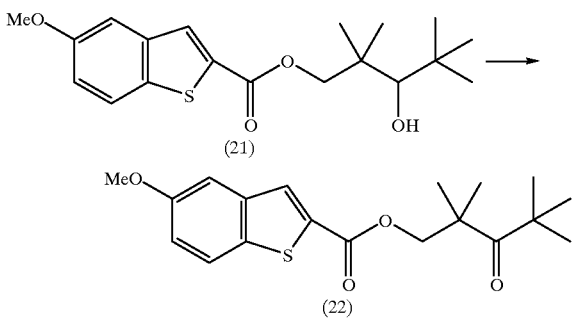

In nitrogen atmosphere at a room temperature, 2.70 g (12.5 mmol) of PCC and 4.5 g of Celite were suspended with 20 ml of methylene chloride. Adding dropwise 15 ml of methylene chloride dissolving 2.84 g (8.11 mmol) of 3-hydroxy-2,2,4,4-tetramethylpentane-1-yl 5-methoxybenzothiophen-2-carboxylate (Compound [21]), the mixture was stirred for 24 hours. Adding 2 ml of 2-propanol, the reaction mixture was stirred for 1 hour. Then adding 100 ml of ether, the resulting mixture was filtrated by Celite and the filtrate was concentrated. The concentrate was applied to a silica gel column and the elution was carried out with the mixture of hexane and ethyl acetate (hexane:ethyl acetate=10:1) to obtain 2.68 mg (7.70 mmol) of 2,2,4,4-tetramethyl-3-oxopentane-1-yl 5-methoxybenzothiophen-2-carboxylate (Compound [22]). Yield 88.7%.
melting point;74.0–75.5° C. (colorless needle crystal obtained by recrystallization from the mixture of hexane and ethyl acetate)
$^1$HNMR(400 MHz, CDCl$_3$); δ1.30 (s, 9H), 1.39 (s, 6H), 3.87 (s, 3H), 4.41(s, 2H), 7.10(dd, J=8.8 and 2.4 Hz, 1H), 7.28 (d, J=2.4 Hz, 1H), 7.70 (d, J=8.8 Hz, 1H), 7.93 (s, 1H) ppm
IR (KBr); 2968, 1689, 1525, 1292, 1218, 1069 cm$^{-1}$
Mass (m/z, %); 348 (M$^+$ 14), 292(22), 208(39), 191(100), 163(10),

Reference Example 16

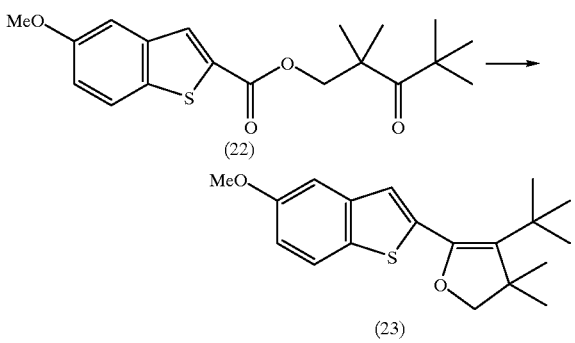

In nitrogen atmosphere, under cooling with ice bath, adding 3.15 g (20.4 mmol) of titanium chloride to 70 ml of THF, the mixture was stirred for 15 minutes, then adding 380 mg (10.5 mmol) of aluminium lithium hydride, the mixture was further stirred for 15 minutes. Adding 1.4 ml (10.5 mmol) of triethylamine, the mixture was refluxed for 30 minutes. Then adding dropwise 20 ml of THF dissolving 1.44 g (3.82 mmol) of 2,2,4,4-tetramethyl-3-oxopentane-1-yl 5-methoxybenzothiophen-2-carboxylate (Compound [22]), the mixture was refluxed for 2 hours. After cooling the reaction mixture, the mixture was added to 500 ml of saturated sodium hydrogencarbonate and extracted with 300 ml of ethyl acetate. The organic layer was washed with 500 ml of saturated aqueous solution of sodium chloride, then dried with magnesium sulfate anhydride and concentrated. The concentrate was dissolved in methylene chloride and added 121 mg of PPTS (0.482 mmol), then the mixture was stirred at a room temperature for 24 hours. The reaction mixture was added to a saturated aqueous solution of sodium hydrogencarbonate and extracted with ethyl acetate. The organic layer was washed with saturated aqueous solution of sodium chloride, then dried with magnesium sulfate anhydride and concentrated. The concentrate purified with silica gel column using the mixture of hexane and ethyl acetate (hexane:ethyl acetate=15:1) to obtain 624 mg (1.97 mmol) of 4-t-butyl-5-(5-methoxybenzothiophen-2-yl)-3,3-dimethyl-2,3-dihydrofuran (Compound [23]). Yield 51.7%.
melting point; 58–59° C. (colorless granular crystal obtained by recrystallization from hexane)
$^1$HNMR(400 MHz, CDCl$_3$); δ1.18 (s, 9H), 1.34 (s, 6H), 3.96 (s, 3H), 3.90(s, 2H), 6.97(dd, J=8.8 and 2.4 Hz, 1H), 7.20(s, 1H), 7.20(d, J=2.4 Hz, 1H), 7.65 (d, J=8.8 Hz, 1H) ppm
IR (KBr); 2981, 2870, 1598, 1453, 1216, 1021, 806 cm$^{-1}$
Mass (m/z, %); 316 (M$^+$ 34), 301(100), 245(30), 191(27)

Reference Example 17

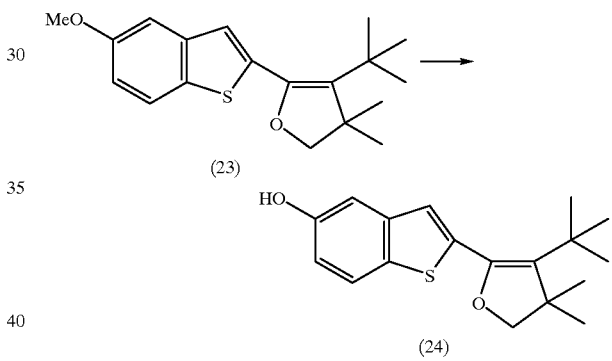

In nitrogen atmosphere, under cooling with ice bath, 160 mg (4.0 mmol) of 60% sodium hydride was added to 3 ml of DMF. Adding 0.40 ml (5.4 mmol) of ethanethiol, the mixture was stirred for 15 minutes. Adding 3 ml of DMF dissolving 370 mg (1.17 mmol) of 4-t-butyl-5-(5-methoxybenzothiophen-2-yl)-3,3-dimethyl-2,3-dihydrofuran (Compound [23]), the mixture was refluxed for 3 hours. After standing to cool the reaction mixture, the mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 308 mg (1.02 mmol) of 4-t-butyl-5-(5-hydroxybenzothiophen-2-yl)-3,3-dimethyl-2,3-dihydrofuran (Compound [24]). Yield 87.3%
melting point; 195.5–196.5° C. (colorless needle crystal obtained by recrystallization from the mixture of hexane and ethyl acetate)
$^1$HNMR(400 MHz, CDCl$_3$); δ1.18 (s, 9H), 1.34 (s, 6H), 3.90 (s, 2H), 4.65(s, 1H), 6.88(dd, J=8.8 and 2.4 Hz, 1H), 7.15(s, 1H), 7.16(d, J=2.4 Hz, 1H), 7.63 (d, J=8.8 Hz, 1H) ppm IR (KBr); 3363, 2963, 1599, 1438, 1210, 1024 cm$^{-1}$
Mass (m/z, %); 302 (M$^+$ 36), 287(100), 246(6), 231(39)

Reference Example 18

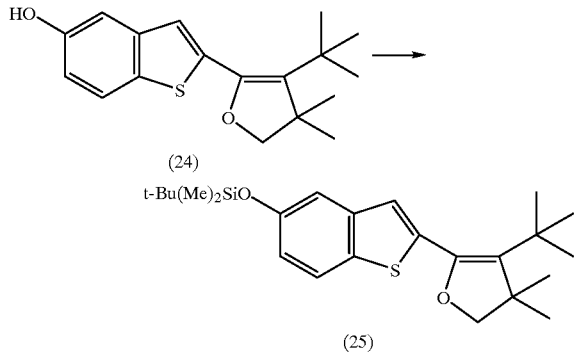

In nitrogen atmosphere, under cooling with ice bath, adding 0.20 ml (1.5 mmol) of triethylamine to 3 ml of DMF dissolving 113 mg (0.379 mmol) of 4-t-butyl-5-(5-hydroxybenzothiophen-2-yl)-3,3-dimethyl-2,3-dihydrofuran (Compound [24]), the mixture was stirred for 15 minutes. Adding 150 mg (1.00 mmol) of t-butyldimethylchlorosilane, the mixture was stirred for 2 hours at a room temperature. The resulting mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 154 mg (0.370 mmol) of 4-t-butyl-5-(5-(t-butyldimethylsiloxy)benzothiophen-2-yl)-3,3-dimethyl-2,3-dihydrofuran (Compound [25]). Yield 97.4%.
melting point; 88–89° C. (colorless granular crystal obtained by recrystallization from hexane)
$^1$HNMR(400 MHz, CDCl$_3$); δ0.21 (s, 6H), 1.00 (s, 9H), 1.19 (s, 9H), 1.34(s, 6H), 3.90(s, 2H), 6.88(dd, J=8.8and2.4 Hz, 1H), 7.14(s, 1H), 7.14(d, J=2.4 Hz, 1H), 7.61(d, J=8.8 Hz, 1H) ppm
IR (KBr); 2955, 2862, 1599, 1451, 1228, 870 cm$^{-1}$
Mass (m/z, %); 416(M$^+$ 27), 401(100), 345(18), 291(9)

Example 4

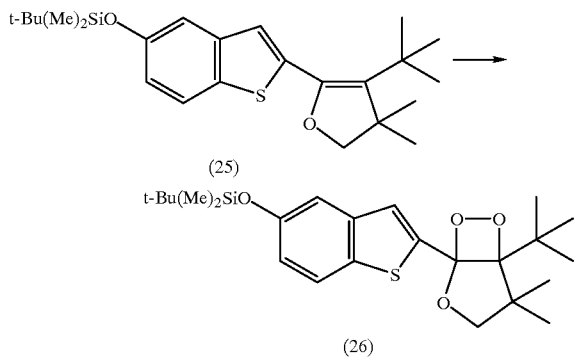

Adding 1 mg of TPP to 4 ml of methylene chloride dissolving 121 mg (0.298 mmol) of 4-t-butyl-5-(5-(t-butyldimethylsiloxy)benzothiophen-2-yl)-3,3-dimethyl-2,3-dihydrofuran (Compound [25]), the mixture was stirred in oxygen atmosphere, at the temperature of −78° C. This solution was externally irritated with a 940 W sodium lamp for 1 hours. The reaction mixture was concentrated and fractionated with aliquot thin layer chromatography using the mixture of hexane and ethyl acetate (hexane:ethyl acetate=7:1) to obtain 105 mg (0.234 mmol) of 5-t-butyl-1-(5-(t-butyldimethylsiloxy)benzothiophen-2-yl)-4,4-dimethyl-2,6,7-trioxabicyclo[3.2.0]heptane (Compound [26]). Yield 78.5%.
melting point; 125–126° C. (pale yellow solid)
$^1$HNMR(400 MHz, CDCl$_3$); δ0.23 (s, 6H), 1.00 (s, 9H), 1.13 (s, 6H), 1.15(s, 3H), 1.46(s, 6H), 4.17 (q$_{AB}$, J=8.3 Hz, 2H), 6.92(dd, J=8.8and2.4 Hz, 1H), 7.21(d, J=2.4 Hz, 1H), 7.50(s, 1H), 7.63(d, J=8.8 Hz, 1H) ppm
IR (KBr); 2956, 2892, 1598, 1534, 1451, 1227, 847 cm$^{-1}$ Reference Example 19

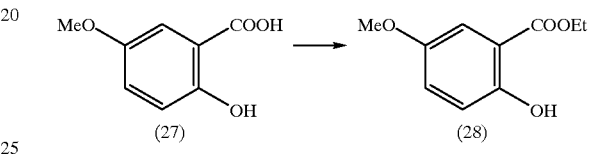

In nitrogen atmosphere, under cooling with ice bath, 8.58 g (51.0 mmol) of 5-methoxy salicylate (Compound [27]) was dissolved in 50 ml of DMF, and 6.42 g (76.4 mmol) of sodium hydrogencarbonate was added and then the mixture was stirred for 30 minutes. Adding 4.20 ml (52.5 mmol) of methyl iodide, the mixture was stirred for24 hours at a room temperature. The resulting mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 8.52 g (43.5 mmol) of ethyl 2-hydroxy-5-methoxy benzoate (Compound [28]) as a colorless oil. Yield 85.1 %.
$^1$HNMR(400 MHz, CDCl$_3$); δ1.42(t, J=6.8 Hz, 3H), 3.79(s, 3H), 4.42 (q, J=6.8 Hz, 2H), 6.91(d, J=8.8 Hz, 1H), 7.07(dd, J=8.8 and 2.4 Hz, 1H), 7.30 (d, J=2.4 Hz, 1H), 10.4 (s, 1H) ppm
IR (liquid film); 3207, 2985, 2835, 1677, 1490, 1222, 828 cm$^{-1}$
Mass (m/z, %); 196 (M$^+$ 35), 150(100), 135(17), 111(19), 95(31), 83(26)

Reference Example 20

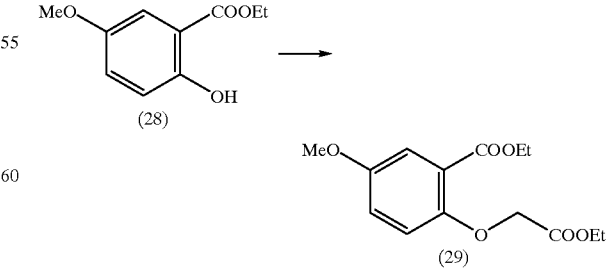

In nitrogen atmosphere, under cooling with ice bath, 6.00 g (30.6 mmol) of ethyl 2-hydroxy-5-methoxy benzoate (Compound [28]) was dissolved in 50 ml of DMF, and 4.56 g (33.0 mmol) of potassium carbonate was added and then the mixture was stirred for 30 minutes. Adding 3.4 ml (30.7 mmol) of bromoacetate, the mixture was stirred for 24 hours at a room temperature. The resulting mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 7.72 g (27.4 mmol) of ethyl 2-ethoxycarbonylmethoxy-5-methoxy benzoate (Compound [29]) as a colorless oil. Yield 89.4 %

$^1$HNMR(400 MHz, CDCl$_3$); δ1.30(t, J=6.8 Hz, 3H), 1.38(t, J=6.8 Hz, 3H), 3.80(s, 3H), 4.26(q, J=6.8 Hz, 2H), 4.37(q, J=6.8 Hz, 2H), 4.63(s, 2H), 6.93(d, J=8.8 Hz, 1H), 6.96(dd, J=8.8 and 2.4 Hz, 1H), 7.34(d, J=2.4 Hz, 1H) ppm IR (liquid film); 2982, 1728, 1498, 1287, 1195, 1075 cm$^{-1}$ Mass (m/z, %); 282 (M$^+$ 54), 209(23), 195(24), 179(97), 163(70), 151(100), 135(22), 107(25)

Reference Example 21

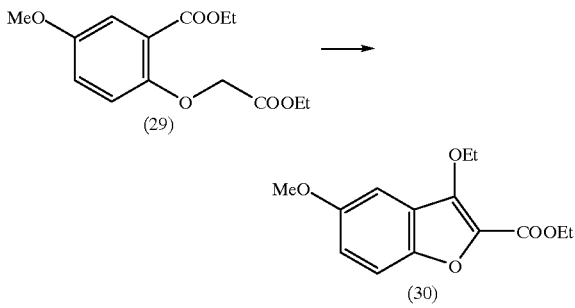

In nitrogen atmosphere, 1.69 ml (12.0 mmol) of diisopropylamine was dissolved in 10 ml of THF, and 6.2 ml (10 mmol) of 1.6M butyl lithium hexane solution was added and the mixture was stirred for 30 minutes. Adding dropwise 15 ml of THF dissolving 1.37 g (4.86 mmol) of ethyl 2-ethoxycarbonylmethoxy-5-methoxy benzoate (Compound [29]) at the temperature of −78° C., the mixture was stirred for 30 minutes. After increasing a room temperature, an aqueous saturated solution of ammonium chloride was added. The resulting mixture was added to an aqueous saturated solution of ammonium chloride and extracted with ethyl acetate. The organic layer was washed with saturated aqueous solution of sodium chloride, then dried with magnesium sulfate anhydride and concentrated. The concentrate was dissolved in 15 ml of DMF and 700 mg (5.07 mmol) of potassium carbonate was added and the mixture was stirred for 30 min. Adding 0.6 ml (7.3 mmol) of ethyl iodide, the mixture was stirred for 24 hours at a room temperature. The resulting mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate= 5:1) to obtain 580 mg (2.20 mmol) of ethyl 3-ethoxy-5-methoxybenzofuran-2-carboxylate (Compound [30]). Yield 45.1%.

melting point:50–51° C. (colorless granular crystal obtained by recrystallization from the mixture of hexane and ethyl acetate)

$^1$HNMR(400 MHz, CDCl$_3$); δ1.43 (t, J=6.8 Hz, 3H), 1.46 (t, J=6.8 Hz, 3H), 3.86 (s, 3H), 4.43(q, J=6.8 Hz, 2H), 4.45(q, J=6.8 Hz, 2H), 7.05–7.40 (m, 3H) ppm IR (KBr); 3394, 2984, 1697, 1571, 1233, 1024 cm$^{-1}$ Mass (m/z, %); 265 (M$^+$ 7), 252(25), 206(100), 191(11), 180(69), 166(43), 151(32)

Reference Example 22

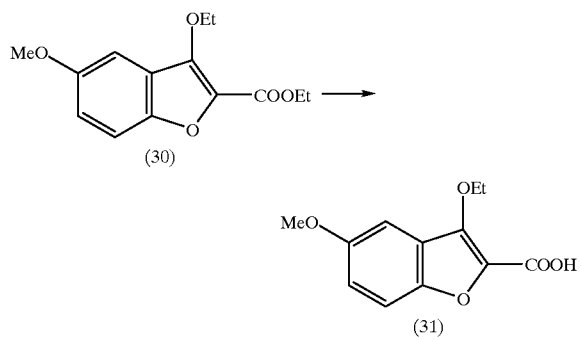

Under cooling with ice bath, 840 mg (15.0 mmol) of potassium hydroxide and 2.0 ml of pure water were added to 10 ml of methanol dissolving 1.23 g (4.66 mmol) of ethyl 3-ethoxy-5-methoxybenzofuran-2-carboxylate (Compound [30]) was added and the mixture was stirred for 4 hours. The reaction mixture was added to 100 ml of 1N sulfuric acid, and extracted with ethyl acetate. The organic layer was washed with saturated aqueous solution of sodium chloride, then dried with magnesium sulfate anhydride and concentrated to obtain 1.01 g (4.28 mmol) of 3-ethoxy-5-methoxybenzofuran-2-carboxylate (Compound [31]). Yield:92.2% melting point; 157–158° C. (colorless granular crystal obtained by recrystallization from ethanol)

$^1$HNMR(400 MHz, CDCl$_3$); δ1.50 (t, J=6.8 Hz, 3H), 3.87(s, 3H), 4.58(q, J=6.8 Hz, 2H), 7.09–7.43 (m, 3H) ppm IR (KBr); 2991, 1671, 1570, 1484, 1234, 1185, 1026 cm$^{-1}$ Mass (m/z, %); 236 (M$^+$ 25), 192(75), 190(100), 177(12), 164(47)

Reference Example 23

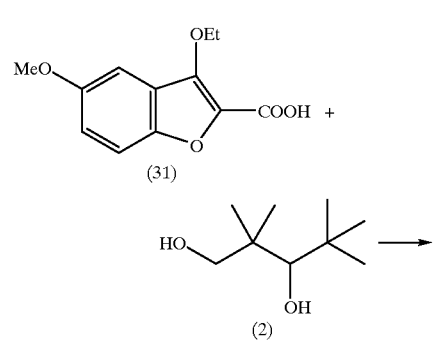

-continued

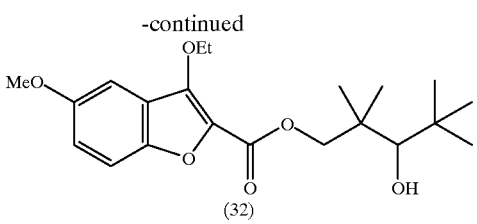

In nitrogen atmosphere at a room temperature, 34 mg (0.28 mmol) of DIMAP was added to the 10 ml of methylene chloride dissolving 570 mg (2.42 mmol) of 3-ethoxy-5-methoxybenzofuran-2-carboxylate (Compound [31]) and 465 mg (2.90 mmol) of 2,2,4,4-tetramethyl-1,3-pentandiol (Compound [2]) and 10 ml of methylene chloride dissolving 605 mg (3.15 mmol) of WSC.HCl was added dropwise, then the mixture was stirred for 24 hours. The resulting mixture was added to a saturated aqueous solution of ammonium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=10:1) to obtain 824 mg (2.18 mmol) of 3-hydroxy-2,2,4,4-tetramethylpentane-1-yl 3-ethoxy-5-methoxybenzofuran-2-carboxylate (Compound [32]). Yield 90.3%.

melting point; 100.3–101.3° C. (colorless needle crystal obtained by recrystallization from the mixture of hexane and ethyl acetate)

$^1$HNMR(400 MHz, CDCl$_3$); δ1.06(s, 9H), 1.13(s, 3H), 1.22 (s, 3H), 1.50(t, J=6.8 Hz, 3H), 2.68(d, J=6.4 Hz, 1H), 3.25(d, J=6.4 Hz, 1H), 3.86(s, 3H), 4.25(q$_{AB}$, J=10.7 Hz, 2H), 4.49(q, J=6.8 Hz, 2H), 7.07(dd, J=8.8 and 2.4 Hz, 1H), 7.11(d, J=2.4 Hz, 1H), 7.41(d, J=8.8 Hz, 1H) ppm IR (KBr); 3505, 2954, 1681, 1572, 1481, 1237, 1040 cm$^{-1}$ Mass (m/z, %); 378 (M$^+$ 3), 265(16), 236(24), 219(100), 190(74), 150(47), 127(52)

Reference Example 24

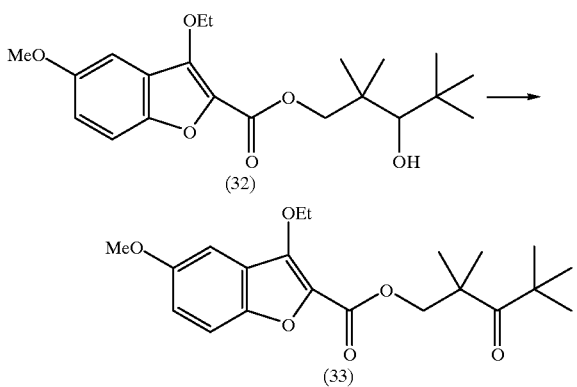

In nitrogen atmosphere at a room temperature, 1.13 mg (5.25 mmol) of PCC and 2.50 g of Celite were suspended with 20 ml of methylene chloride. Adding dropwise 15 ml of methyl chloride dissolving 1.2 g (3.17 mmol) of 3-hydroxy-2,2,4,4-tetramethylpentane-1-yl 3-ethoxy-5-methoxybenzofuran-2-carboxylate (Compound [32]), the mixture was stirred for 24 hours. Adding 2 ml of 2-propanol, the reaction mixture was stirred for 1 hour. Then adding 100 ml of ether, the resulting mixture was filtrated by Celite and the filtrate was concentrated. The concentrate was applied to a silica gel column and the elution was carried out with the mixture of hexane and ethyl acetate (hexane:ethyl acetate= 10:1) to obtain 1.06 g (2.81 mmol) of 2,2,4,4-tetramethyl-3-oxopentane-1-yl 3-ethoxy-5-methoxybenzofuran-2-carboxylate (Compound [33]). Yield 88.8% melting point; 105–106° C. (colorless needle crystal obtained by recrystallization from the mixture of hexane and ethyl acetate)

$^1$HNMR(400 MHz, CDCl$_3$); δ1.29(s, 9H), 1.39(s, 6H), 1.45 (t, J=6.8 Hz, 3H), 3.85(s, 3H), 4.44(s, 2H), 4.44(q, J=6.8 Hz, 2H), 7.04–7.36 (m, 3H) ppm IR (KBr); 2976, 1710, 1482, 1416, 1230, 1169, 963 cm$^{-1}$ Mass (m/z, %); 376 (M$^+$ 17), 336(9), 236(18), 219(100), 208(18), 190(39), 179(49)

Reference Example 25

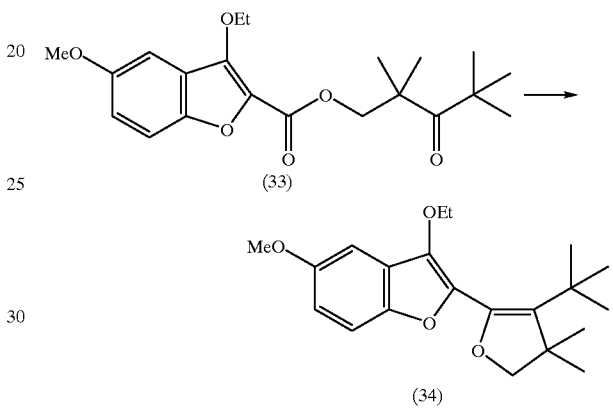

In nitrogen atmosphere, under cooling with ice bath, 6.32 g (41.0 mmol) of titanium chloride was added to 70 ml of THF, and the mixture was stirred for 15 minutes. Adding 770 mg (20.3 mmol) of aluminium lithium hydride, the mixture was stirred for 15 minutes. Adding dropwise 2.8ml (20.1 mmol) of Triethylamine, the mixture was refluxed for 30 minutes. Adding dropwise 20 ml of THF dissolving 970 mg (2.58 mmol) of 2,2,4,4-tetramethyl-3-oxopentane-1-yl 3-ethoxy-5-methoxybenzofuran-2-carboxylate (Compound [33]), the mixture was refluxed for 2 hours. After cooling the reaction mixture, the mixture was added to a saturated aqueous solution of sodium hydrogencarbonate and extracted with ethyl acetate. The organic layer was washed with saturated aqueous solution of sodium chloride, then dried with magnesium sulfate anhydride and concentrated. Dissolving 713 mg of concentrate with 10 ml of methylene chloride and adding 75 mg (0.30 mmol) of PPTS, the mixture was stirred at a room temperature for 24 hours. The reaction mixture was added to a saturated aqueous solution of sodium hydrogencarbonate and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=15:1) to obtain 245 mg (0.711 mmol) of 4-t-butyl-5-(3-ethoxy-5-methoxybenzofuran-2-yl)-3,3-dimethyl-2,3-dihydrofuran (Compound [34]). Yield 27.6%.

melting point; 60–61° C. (colorless granular crystal obtained by recrystallization from hexane)

$^1$HNMR(400 MHz, CDCl$_3$); δ1.15(s, 9H), 1.32(s, 6H), 1.40 (t, J=6.8 Hz, 3H), 3.87(s, 3H), 3.88(s, 2H), 4.36(q, J=6.8 Hz,

2H), 6.97(dd, J=8.8and2.4 Hz, 1H), 7.16(d, J=2.4 Hz, 1H), 7.53(d, J=8.8 Hz, 1H) ppm
IR (KBr); 2957, 1671, 1483, 1363, 1213, 1051, 805 cm$^{-1}$
Mass (m/z, %); 344 (M$^+$ 27), 329(100), 285(8), 273(6), 151(16)

Reference Example 26

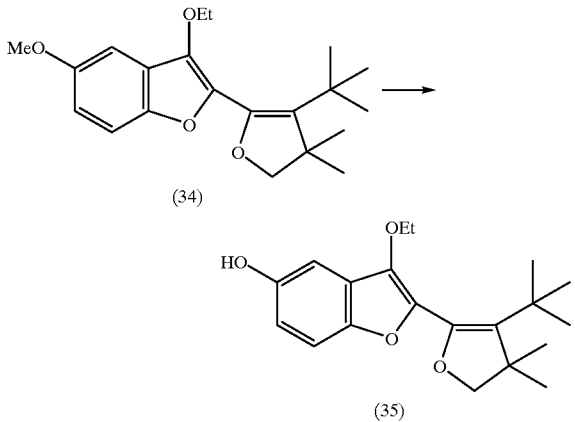

In nitrogen atmosphere, under cooling with ice bath, 110 mg (2.75 mmol) of 60% sodium hydride was added to 3 ml of DMF. Adding 0.30 ml (4.1 mmol) of ethanethiol, the mixture was stirred for 15 minutes. Adding 3 ml of DMF dissolving 209 mg (0.608 mmol) of 4-t-butyl-5-(3-ethoxy-5-methoxybenzofuran-2-yl)-3,3-dimethyl-2,3-dihydrofuran (Compound [34]), the mixture was refluxed for 3 hours. After standing to cool the reaction mixture, the mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 121 mg (0.367 mmol) of 4-t-butyl-5-(3-ethoxy-5-hydroxybenzofuran-2-yl)-3,3-dimethyl-2,3-dihydrofuran (Compound [35]) as a pale yellow oil. Yield:60.3%
$^1$HNMR(400 MHz, CDCl$_3$); δ1.15(s, 9H), 1.33(s, 6H), 1.38 (t, J=6.8 Hz, 3H), 3.90(s, 2H), 4.25(q, J=6.8 Hz, 2H), 4.59(s, 1H), 6.79(dd, J=8.8 and 2.4 Hz, 1H), 6.95 (d, J=2.4 Hz, 1H), 7.23(d, J=8.8 Hz, 1H) ppm
IR (liquid film); 3399, 2960, 1461, 1369, 1204, 1106, 807 cm$^{-1}$
Mass (m/z, %); 330 (M$^+$ 30), 315(100), 231(9), 177(13), 137(20)

Reference Example 27

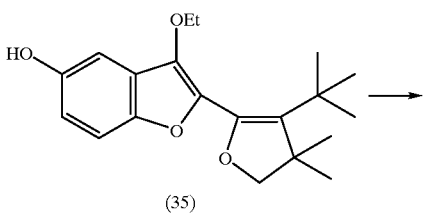

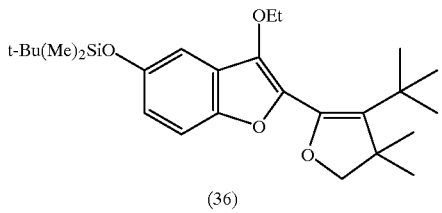

In nitrogen atmosphere, under cooling with ice bath, adding 0.2 ml (1.5 mmol) of triethylamine to 3 ml of DMF dissolving 49 mg (0.15 mmol) of 4-t-butyl-5-(3-ethoxy-5-hydroxybenzofuran-2-yl)-3,3-dimethyl-2,3-dihydrofuran (Compound [35]), the mixture was stirred for 15 minutes. Adding 150 mg (1.00 mmol) of t-butyldimethylchlorosilane, the mixture was stirred for 2 hours at a room temperature. The resulting mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate= 5:1) to obtain 56 mg (0.13 mmol) of 4-t-butyl-5-(5-(t-butyldimethylsiloxy)-3-ethoxybenzofuran-2-yl)-3,3-dimethyl-2,3-dihydrofuran (Compound [36]) as a pale yellow oil. Yield 84.9%.
$^1$HNMR(400 MHz, CDCl$_3$); δ0.21(s, 6H), 1.00(s, 9H), 1.16 (s, 9H), 1.31(s, 6H), 1.39(t, J=6.8 Hz, 3H), 3.89(s, 2H), 4.24(q, J=6.8 Hz, 2H), 6.78(dd, J=8.8 and 2.4 Hz, 1H), 6.95 (d, J=2.4 Hz, 1H), 7.20(d, J=8.8 Hz, 1H) ppm
IR (liquid film); 2957, 2859, 1741, 1617, 1577,1470, 1255, 1105, 838 cm$^{-1}$
Mass (m/z, %); 444 (M$^+$ 24), 429(100), 385(9), 251(9), 177(6), 73(20)

Example 5

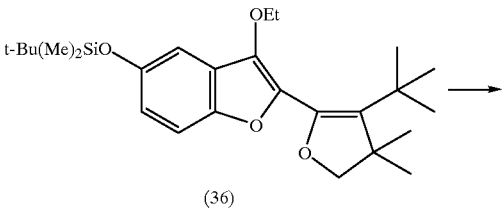

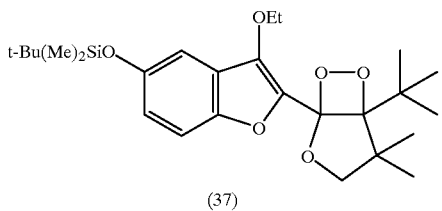

Adding 1 mg of TPP to 2 ml of methylene chloride dissolving 47 mg (0.066 mmol) of 4-t-butyl-5-(5-(t-butyldimethylsiloxy)-3-ethoxybenzofuran-2-yl)-3,3-dimethyl-2,3-dihydrofuran (Compound [36]), the mixture was stirred in oxygen atmosphere, at the temperature of −78° C. This solution was externally irritated with a 940 W sodium lamp for 4 hours. The reaction mixture was concentrated to obtain 5-t-butyl-1-(5-(t-butyldimethylsiloxy)-3-ethoxybenzofuran-2-yl)-4,4-dimethyl-2,6,7-trioxabicyclo [3.2.0]heptane (Compound [37]) as a crude product.

Reference Example 28

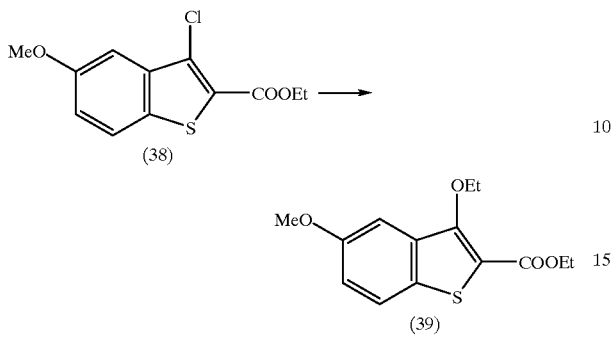

In nitrogen atmosphere, 2.0 ml (5.34 mmol) of 21% sodium ethoxide ethanol was added dropwise to 10 ml of THF dissolving 720 mg (2.67 mmol) of ethyl 3-chloro-5-methoxybenzothiophene-2-carboxylate (Compound [38]) and the mixture was refluxed for 4 hours. The mixture was added to the solution of saturated ammonium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=10:1) to obtain 630 mg (2.26 mmol) of ethyl 3-ethoxy-5-methoxybenzothiophen-2-carboxylate (Compound [39]). Yield 84.6% melting point; 42–43° C. (colorless needle crystal obtained by recrystallization from the mixture of hexane and ethyl acetate)

$^1$HNMR(400 MHz, CDCl$_3$); δ1.41(t, J=6.8 Hz, 3H), 1.48(t, J=6.8 Hz, 3H), 3.89(s, 3H), 4.37(q, J=6.8 Hz, 2H), 4.38(q, J=6.8 Hz, 2H), 7.12(dd, J=8.8 and 2.4 Hz, 1H), 7.24(d, J=2.4 Hz, 1H), 7.60 (d, J=8.8 Hz, 1H) ppm IR (KBr); 2975, 1709, 1523, 1302, 1218, 1028 cm$^{-1}$ Mass (m/z, %); 280 (M$^+$ 25), 206(100), 179(10), 150(7)

Reference Example 29

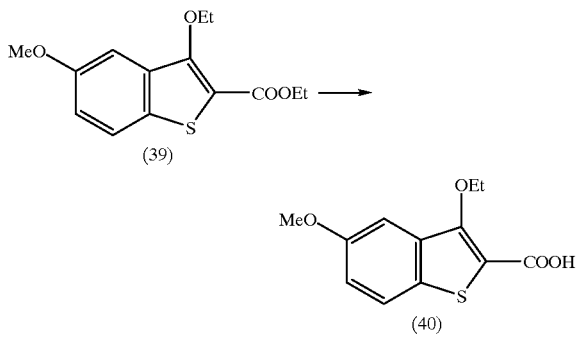

Under cooling with ice bath, 560 mg (10.0 mmol) of potassium hydroxide and 2 ml of pure water were added to 10 ml of methanol dissolving 1.00 g (3.57 mmol) of ethyl 3-ethoxy-5-methoxybenzothiophen-2-carboxylate (Compound [39]) and the mixture was stirred at a room temperature for 4 hours. The reaction mixture was added to 100 ml of 1N sulfuric acid, and extracted with ethyl acetate. The organic layer was washed with saturated aqueous solution of sodium chloride, then dried with magnesium sulfate anhydride and concentrated to obtain 850 mg (3.37 mmol) of 3-ethoxy-5-methoxybenzothiophen-2-carboxylic acid (Compound [40]). Yield 94.5% melting point 162–164° C. (colorless granular crystal obtained by recrystallization from the mixture of hexane and ethyl acetate)

$^1$HNMR(400 MHz, CDCl$_3$); δ1.51(t, J=6.8 Hz, 3H), 3.85(s, 3H), 4.48(q, J=6.8 Hz, 2H), 7.12(dd, J=8.8 and 2.4 Hz, 1H), 7.23(d, J=2.4 Hz, 1H), 7.65(d, J=8.8 Hz, 1H) ppm IR (KBr); 2976, 2597, 1682, 1524, 1253, 1221, 1066 cm$^{-1}$ Mass (m/z, %);252 (M$^+$, 25), 206(100), 180(69), 166(43), 151(32), 123(25)

Reference Example 30

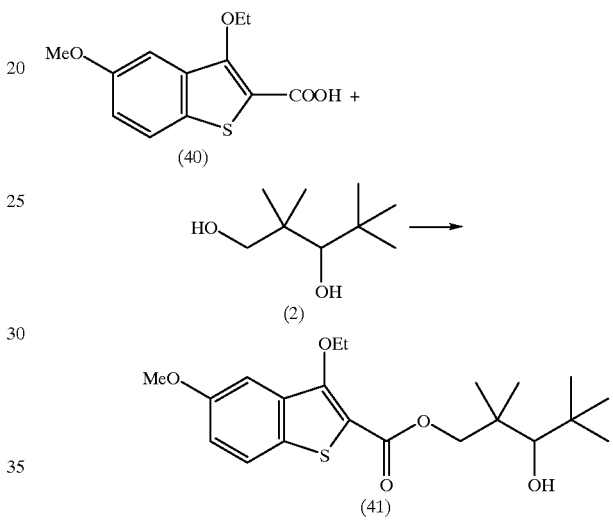

In nitrogen atmosphere, under cooling with an ice bath, 34 mg (0.28 mmol) of DIMAP was added to 10 ml of methylene chloride dissolving 771 mg (3.06 mmol)of 3-ethoxy-5-methoxybenzothiophen-2-carboxylic acid (Compound [40]) and 541 mg (3.38 mmol) of 2,2,4,4-tetramethyl-1,3-pentandiol (Compound [2]) and 10 ml of methylene chloride dissolving 650 mg of WSC.HCl (3.38 mmol) was added dropwise, then the mixture was stirred at a room temperature for 24 hours. The resulting mixture was added to a saturated aqueous solution of ammonium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 962 mg (2.43 mmol) of 3-hydroxy-2,2,4,4-tetramethylpentane-1-yl 3-ethoxy-5-methoxybenzothiophen-2-carboxylate (Compound [41]) as a pale yellow oil. Yield 79.8%

$^1$HNMR(400 MHz, CDCl$_3$); δ1.06(s, 9H), 1.13(s, 3H), 1.19 (s, 3H), 1.48(t, J=6.8 Hz, 3H), 2.17(d, J=6.4 Hz, 1H), 3.25(d, J=6.4 Hz, 1H), 3.89(s, 3H), 4.20(q$_{AB}$, J=10.7 Hz, 2H), 4.41(q, J=6.8 Hz, 2H), 7.13 (dd, J=8.8 and 2.4 Hz, 1H), 7.25 (d, J=2.4 Hz, 1H), 7.61 (d, J=8.8 Hz, 1H) ppm IR (liquid film);3553, 2960, 1604, 1525, 1308, 1216, 809 cm$_{-1}$ Mass (m/z, %); 394 (M$^+$ 1), 376(18), 252(17), 235(63), 206(100), 191(12), 180(29), 166(35), 151(21)

Reference Example 31

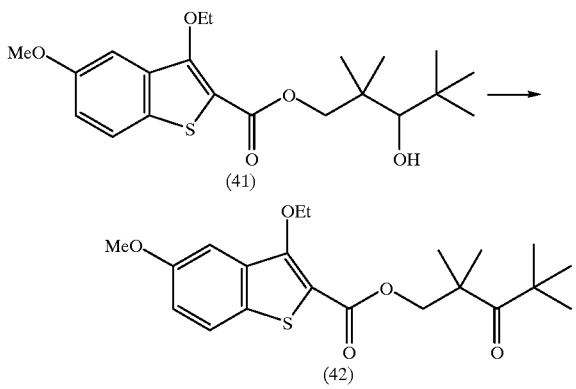

In nitrogen atmosphere at a room temperature, 1.13 mg (5.25 mmol) of PCC and 2.50 g of Celite were suspended with 20 ml of methylene chloride. Adding dropwise 15 ml of methyl chloride dissolving 1.38 g (3.50 mmol) of 3-hydroxy-2,2,4,4-tetramethylpentane-1-yl 3-ethoxy-5-methoxybenzothiophen-2-carboxylate (Compound [41]), the mixture was stirred for 24 hours. Adding 2 ml of 2-propanol, the reaction mixture was stirred for 1 hour. Then adding 100 ml of ether, the resulting mixture was filtrated by Celite and the filtrate was concentrated. The concentrate was applied to a silica gel column and the elution was carried out with the mixture of hexane and ethyl acetate (hexane:ethyl acetate=10:1) to obtain 1.18 g (3.01 mmol) of 2,2,4,4-tetramethyl-3-oxopentane-1-yl 3-ethoxy-5-methoxybenzothiophen-2-carboxylate (Compound [42]) as a colorless oil. Yield 86.0%.
$^1$HNMR(400 MHz, CDCl$_3$); δ1.30(s, 9H), 1.38(s, 6H), 1.47 (t, J=6.8 Hz, 3H), 3.88(s, 3H), 4.37(s, 2H), 4.39(q, J=6.8 Hz, 2H), 7.13(dd, J=8.8 and 2.4 Hz, 1H), 7.23(d, J=2.4 Hz, 1H), 7.57(d, J=8.8 Hz, 1H) ppm
IR (liquid film); 2972, 1711, 1524, 1469, 1307, 1215, 1061 cm$^{-1}$
Mass (m/z, %); 392 (M$^+$, 46), 336(10), 235(100), 206(64),

Reference Example 32

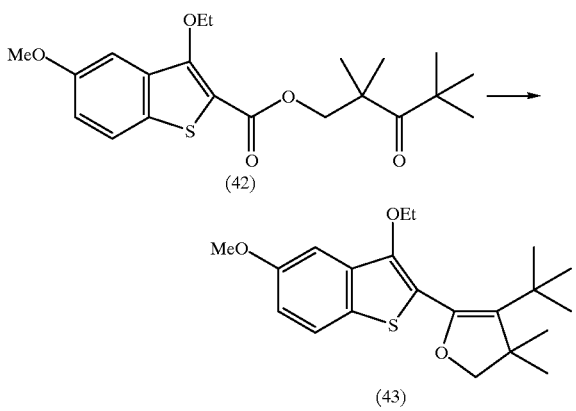

In nitrogen atmosphere, under cooling with ice bath, 3.98 g (25.8 mmol) of titanium chloride was added to 70 ml of THF, and the mixture was stirred for 15 minutes. Adding 480 mg (12.8 mmol) of aluminium lithium hydride, the mixture was stirred for 15 minutes. Adding 1.80 ml (12.9 mmol) of triethylamine, the mixture was refluxed for 30 minutes. Adding dropwise 20 ml of THF dissolving 990 mg (2.52 mmol) of 2,2,4,4-tetramethyl-3-oxopentane-1-yl 3-ethoxy-5-methoxybenzothiophen-2-carboxylate (Compound [42]), the mixture was refluxed for 2 hours. After cooling the reaction mixture, the mixture was added to a saturated aqueous solution of sodium hydrogencarbonate and extracted with ethyl acetate. The organic layer was washed with saturated aqueous solution of sodium chloride, then dried with magnesium sulfate anhydride and concentrated. The concentrate (802 mg) was dissolved with 10 ml of methylene chloride and added 75 mg (0.30 mmol) of PPTS, then the mixture was stirred at a room temperature for 24 hours. The reaction mixture was added to a saturated aqueous solution of sodium hydrogencarbonate and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=15:1) to obtain 490 mg (1.35 mmol) of 4-t-butyl-5-(3-ethoxy-5-methoxybenzothiophen-2-yl)-3,3-dimethyl-2,3-dihydrofuran (Compound [43]) as a pale yellow oil. Yield 53.9%
$^1$HNMR(400 MHz, CDCl$_3$); δ1.15(s, 9H), 1.32(s, 6H), 1.41 (t, J=6.8 Hz, 3H), 3.87(s, 3H), 3.88(s, 2H), 4.36(q, J=6.8 Hz, 2H), 6.97(dd, J=8.8 and 2.4 Hz, 1H), 7.16(d, J=2.4 Hz, 1H), 7.53(d, J=8.8 Hz, 1H) ppm
IR (liquid film); 2960, 2864, 1602, 1311, 1223, 1036 cm$^{-1}$
Mass (m/z, %); 360(M$^+$ 41), 345(100), 301(21), 289(14), 261(11), 245(11), 207(18), 179(14), 139(10)

Reference Example 33

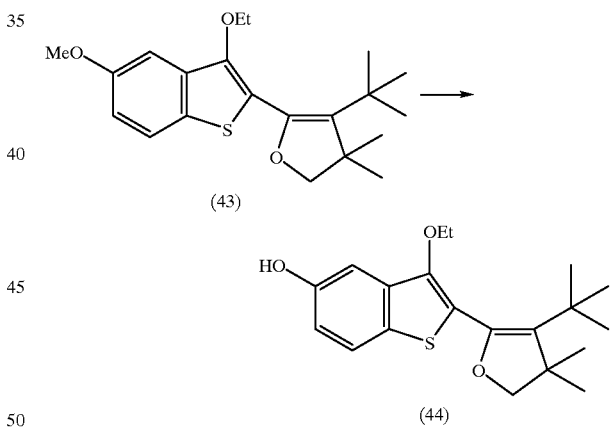

In nitrogen atmosphere, under cooling with ice bath, 110 mg (2.75 mmol) of 60% sodium hydride was added to 3.0 ml of DMF. Then, adding 0.3 ml (4.1 mmol) of ethanethiol, the mixture was stirred for 15 minutes. Adding 3 ml of DMF dissolving 341 mg (0.948 mmol) of 4-t-butyl-5-(3-ethoxy-5-methoxybenzothiophen-2-yl)-3,3-dimethyl-2,3-dihydrofuran (Compound [43]), the mixture was refluxed for 3 hours. After cooling, the reaction mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 205 mg (0.592 mmol) of 4-t-butyl-5-(3-ethoxy-5-hydroxy benzothiophen-2-yl)-3,3-dimethyl-2,3-dihydrofuran (Compound [44]) as a pale yellow oil. Yield 62.4%.

¹HNMR(400 MHz, CDCl₃); δ1.15(s, 9H), 1.32(s, 6H), 1.39 (t, J=6.8 Hz, 3H), 3.88(s, 2H), 4.33(q, J=6.8 Hz, 2H), 4.78(s, 1H), 6.89(dd, J=8.8 and 2.4 Hz, 1H), 7.14(d, J=2.4 Hz, 1H), 7.51(d, J=8.8 Hz, 1H) ppm IR (liquid film); 3396, 2957, 1685, 1602, 1559, 1448, 1260 cm⁻¹

Mass (m/z, %); 346 (M⁺ 44), 331(100), 287(18), 220(15), 193 (11)

Reference Example 34

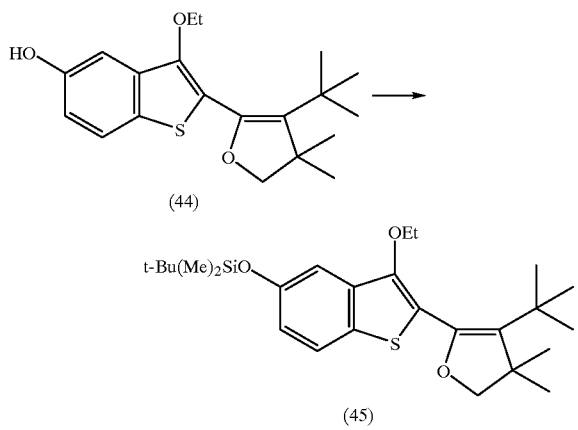

In nitrogen atmosphere, under cooling with ice bath, adding 0.2 ml (1.5 mmol) of triethylamine to 3 ml of DMF dissolving 190 mg (0.549 mmol) of 4-t-butyl-5-(3-ethoxy-5-hydroxybenzothiophen-2-yl)-3,3-dimethyl-2,3-dihydrofuran (Compound [44]), the mixture was stirred for 15 minutes. Adding 150 mg (1.00 mmol) of t-butyldimethylchlorosilane, the mixture was stirred for 2 hours at a room temperature. The resulting mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=5:1) to obtain 225 mg (0.489 mmol) of 4-t-butyl-5-(5-(t-butyldimethylsiloxy)-3-ethoxybenzothiophen-2-yl)-3,3-dimethyl-2,3-dihydrofuran (Compound [45]). Yield 89.1%.

melting point 64–65° C. (colorless granular crystal obtained by recrystallization from the mixture of hexane and ethyl acetate)

¹HNMR(400 MHz, CDCl₃); δ0.21(s, 6H), 1.00(s, 9H), 1.16 (s, 9H), 1.31(s, 6H), 1.39(t, J=6.8 Hz, 3H), 3.87(s, 2H), 4.33(q, J=6.8 Hz, 2H), 6.87(dd, J=8.8 and 2.4 Hz, 1H), 7.14(d, J=2.4 Hz, 1H), 7.49(d, J=8.8 Hz, 1H) ppm IR (KBr); 2957, 2861, 1651, 1445, 1258, 1216 cm⁻¹

Mass (m/z, %);460 (M⁺ 37), 445(100), 401(20), 389(10), 285(11), 73(15)

Example 6

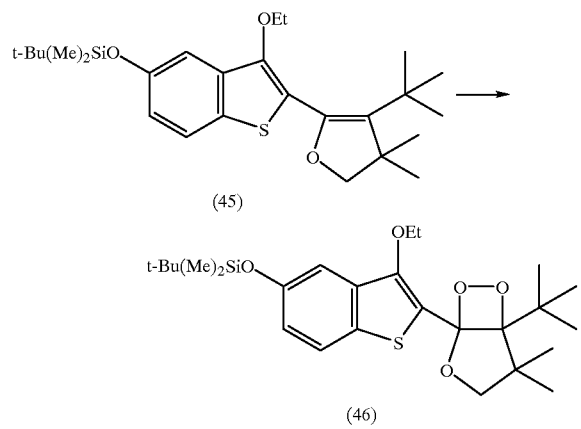

Adding 1 mg of TPP to 4 ml of methylene chloride dissolving 132 mg (0.286 mmol) of 4-t-butyl-5-(5-(t-butyldimethylsiloxy)-3-ethoxybenzothiophen-2-yl)-3,3-dimethyl-2,3-dihydrofuran (Compound [45]), the mixture was stirred in oxygen atmosphere, at the temperature of –78° C. This solution was externally irritated with a 940 W sodium lamp for 4 hours. The reaction mixture was concentrated and fractionated with aliquot thin layer chromatography using the mixture of hexane and ethyl acetate (hexane:ethyl acetate=7:1) to obtain 114 mg (0.243 mmol) of 5-t-butyl-1-(5-(t-butyldimethylsiloxy)-3-ethoxybenzothiophen-2-yl)-4,4-dimethyl-2,6,7-trioxabicyclo[3.2.0]heptane (Compound [46]) as a white compound. Yield 85.0%.

melting point: 106–107° C. (granular crystal)

¹HNMR(400 MHz, CDCl₃); δ0.23(s, 6H), 1.00(s, 9H), 1.13 (s, 6H), 1.15(s, 3H), 1.44(t, J=6.8 Hz, 3H), 1.46(s, 6H), 4.09–4.18 (m, 2H), 4.15(q$_{AB}$, J=8.3 Hz, 2H), 6.92(dd, J=8.8 and 2.4 Hz, 1H), 7.11 (d, J=2.4 Hz, 1H) 7.58 (d, J=8.8 Hz, 1H)ppm IR (KBr); 2956, 1599, 1536, 1452, 1345, 1031, 840 cm⁻¹

Reference Example 35

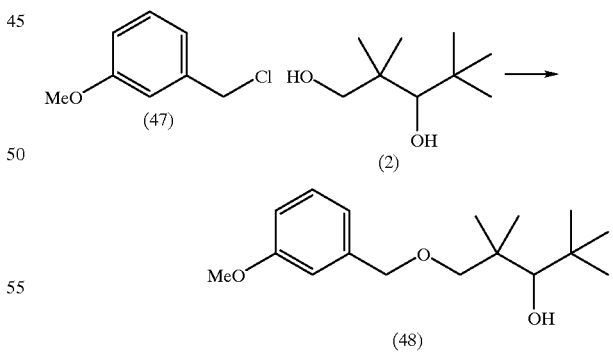

In nitrogen atmosphere, adding dropwise 15 ml of DMF dissolving 7.05 g (44.1 mmol) of 2,2,4,4-tetramethyl-1,3-pentandiol (Compound [2]) to 80 ml of DMF suspended with 2.12 g (53.0 mmol) of 60% sodium hydride over 30 minutes, then the mixture was stirred for 30 minutes. After adding dropwise 15 ml of DMF dissolving 9.07 g (57.9 mmol) of 3-methoxybenzylchoride (Compound [47]) to the mixture over 30 minutes, the mixture was stirred for 12 hours. The reaction mixture was added to saturated aqueous solution of ammonium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=10:1) to obtain 10.7 g of 1-(3-methoxybenzyloxy)-2,2,4,4-tetramethyl-3-pentanol (Compound [48]) as a colorless oil. Yield 86.7%.

$^1$HNMR(400 MHz, CDCl$_3$); δ1.03(s, 9H), 1.04(s, 3H), 1.07 (s, 3H), 3.23(d, J=4.9 Hz, 1H), 3.25(d, J=8.8 Hz, 1H), 3.41(d, J=8.8 Hz, 1H), 3.43(d, J=4.9 Hz, 1H), 3.81(s, 3H), 4.48(s, 2H), 6.81–6.91 (m, 3H), 7.23–7.28 (m, 1H) ppm IR (liquid film); 3502, 2954, 2870, 1489, 1457, 1267, 1080, 1053 cm$^{-1}$ Mass (m/z, %); 280 (M$^+$, 2), 135(31), 121(100), 107(8), 91 (9), 69(13), 55(14)

Reference Example 36

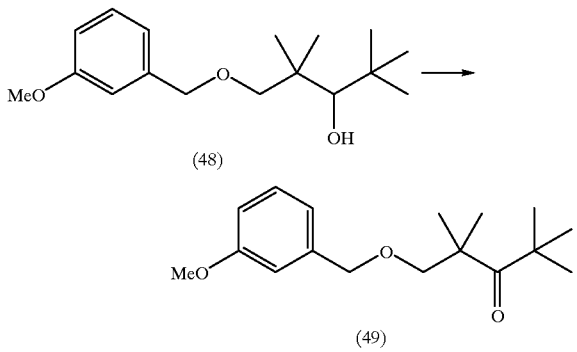

In nitrogen atmosphere at a room temperature, 9.9 g of Celite and 4.61 g (16.5 mmol) of 1-(3-methoxybenzyloxy)-2,2,4,4-tetramethyl-3-pentanol (Compound [48]) were added to 75 ml of dichloromethane and the mixture was stirred. After adding 4.26 g (19.7 mmol) of PCC and stirring for 7 hours, 800 mg (3.71 mmol) of PCC was added and then the reaction mixture was stirred over night. Adding ether to the reaction mixture, the resulting mixture was filtrated by Celite and the filtrate was concentrated. The concentrate was applied to a silica gel column and the elution was carried out with the mixture of hexane and ethyl acetate (hexane:ethyl acetate=10:1) to obtain 4.32 g of 1-(3-methoxybenzyloxy)-2,2,4,4-tetramethyl-3-pentanon (Compound [49]) as a colorless compound. Yield 94.4%.

$^1$HNMR(400 MHz, CDCl$_3$); δ1.23(s, 9H), 1.28(s, 6H), 3.50 (s, 2H), 3.80(s, 3H), 4.47(s, 2H), 6.78–6.88 (m, 3H), 7.23 (t, J=8.1 Hz, 1H) ppm IR (liquid film); 2959, 2870, 1658, 1480, 1466, 1458, 1267, 1108, 1049 cm$^{-1}$ Mass (m/z, %); 278 (M$^+$ 100), 222(50), 121(31), 97(5), 55 (8)

Reference Example 37

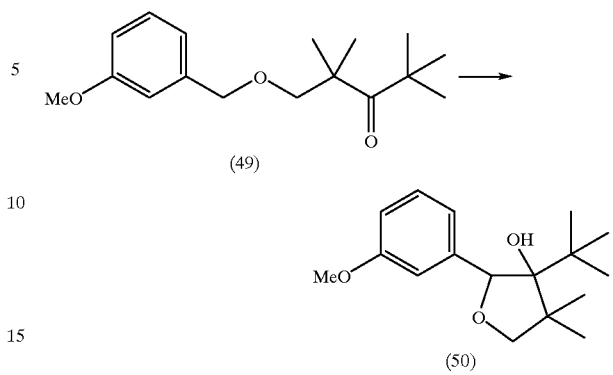

In nitrogen atmosphere, 1.50 ml (11.4 mmol) of diisopropylamin and 6.60 ml (10.6 mmol) of 1.6 M butyllithium hexane were added to 15 ml of THF anhydride at a room temperature, and the mixture was stirred for 30 minutes. Adding 10 ml of THF dissolving 1.48 g (5.32 mmol) of 1-(3-methoxybenzyloxy)-2,2,4,4-tetramethyl-3-pentanon (Compound [49]) at −78° C., the mixture was stirred for 2 hours. The reaction mixture was stirred for 200 minutes with increasing the temperature to a room temperature gradually. The mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate= 1:2) to obtain 1.30 g of 3-t-butyl-3-hydroxy-2-(3-methoxyphenyl)-4,4-dimethyl-2,3,4,5-tetrahydrofuran (Compound [50]). Yield 87.8%.

melting point; 83.0–83.5° C. (colorless granular crystal obtained by recrystallization from hexane and ethyl acetate)

$^1$HNMR(400 MHz, CDCl$_3$); δ0.90(broad s, 9H), 1.19(s, 3H), 1.39(s, 3H), 1.92(s, 1H), 3.80 (q$_{AB}$, J=8.1 Hz, 2H), 3.80(s, 3H), 5.00 (s, 1H), 6.80 (dd, J=7.8 and 2.4 Hz, 1H), 7.10 (d, J=2.4 Hz, 1H), 7.11 (d, J=7.8 Hz, 1H), 7.21 (t, J=7.8 Hz, 1H) ppm IR (liquid film); 3493, 2962, 2881, 1591, 1481, 1278, 1070, 1048 cm$^{-1}$ Mass (m/z,); 278 (M$^+$ 1), 260(29), 245(100), 203(12), 189 (45), 135(52), 121(10), 107(11), 77(9), 55(33)

Reference Example 38

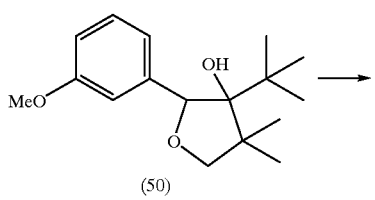

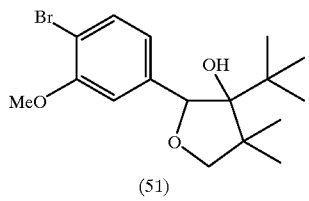

(51)

Adding 2.16 g (7.77 mmol) of 3-t-butyl-3-hydroxy-2-(3-methoxyphenyl)-4,4-dimethyl-2,3,4,5-tetrahydrofuran (Compound [50]) to the mixture of 20 ml of THF and 2 ml of H$_2$O, the mixture was stirred at the temperature of 0° C. After adding 1.54 g (8.65 mmol) of NBS, the mixture was stirred over night with increasing the temperature to a room temperature gradually, 140 mg (0.787 mmol) of NBS was added and the mixture was stirred for 6 hours. The mixture was added to saturated aqueous solution of sodium chloride and extracted with ethyl acetate. The organic layer was washed with a solution of sodium thiosulfate and a saturated aqueous solution of sodium chloride in this order, then dried with magnesium sulfate anhydride and concentrated. The concentrate was crystallized with the mixture of hexane and ethyl acetate to obtain 1.323 g of 2-(4-bromo-3-methoxyphenyl)-3-t-butyl-3-hydroxy-4,4-dimethyl-2,3,4,5-tetrahydrofuran (Compound [51]). Yield 47.7%

$^1$HNMR(400 MHz, CDCl$_3$); δ0.89(s, 9H), 1.20(s, 3H), 1.38 (s, 3H), 1.92(s, 1H), 3.80(q$_{AB}$, J=8.3 Hz, 2H), 3.89(s, 3H), 4.98 (s, 1H), 7.02 (dd, J=8.1 and 2.0 Hz, 1H), 7.12 (d, J=2.0 Hz, 1H), 7.45 (d, J=8.1 Hz, 1H) ppm Mass (m/z, %); 358 (M$^+$, 2.4), 356(M$^+$, 2.5), 340(19), 338(20), 325(79), 323(84), 215(73), 213(67), 201(18), 199 (19), 109(10, 55(100)

Reference Example 39

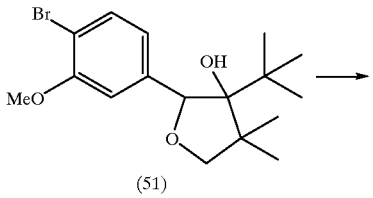

(51)

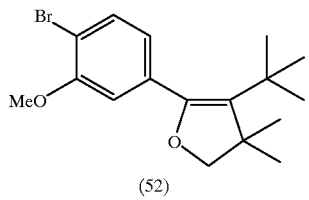

(52)

In nitrogen atmosphere at a room temperature, adding 4.68 g (13 mmol) of 4-t-butyl-(4-bromo-3-methoxyphenyl)-4-hydroxy-3,3-dimethyl-2,3,4,5-tetrahydrofuran (Compound [51]) to 30 ml of toluene anhydride, the mixture was stirred for 10 minutes. Adding 0.27 g (1.4 mmol, 0.1 equivalent) of p-toluenesulfonic acid hydrate, the mixture was stirred at 120° C. for 30 minutes. After cooling to a room temperature, the reaction mixture was added to the mixture of ethyl acetate and saturated aqueous solution of sodium chloride and extracted. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=2:1) to obtain 3.78 g (11.2 mmol) of 4-t-butyl-5-(4-bromo-3-methoxyphenyl)-3,3-dimethyl-2,3-dihydrofuran (Compound [52]) as a colorless oil. Yield 85%.

$^1$HNMR(400 MHz, CDCl$_3$); δ1.06(s, 9H), 1.33(s, 6H), 3.87 (s, 2H), 3.9(s, 3H), 6.79(dd, J=7.9 and 1.6 Hz, 1H), 6.82(d, J=1.6 Hz, 1H), 7.49(d, J=7.9 Hz, 1H) ppm IR (liquid film); 2957, 2866, 1739, 1650, 1570, 1480, 1392, 1237, 1049, 1025, 795 cm$^{-1}$ Mass (m/z, %); 340 (M$^+$+2 26), 338(M$^+$ 26), 325(97), 323(100), 283(6), 282(3), 281(4), 187(7), 185(5), 172(4), 170(3), 77(7), 55(67)

Reference Example 40

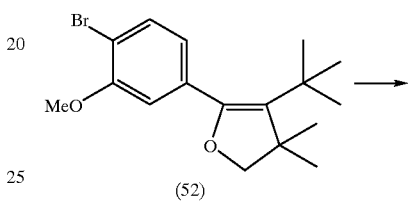

(52)

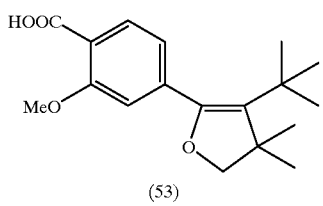

(53)

In nitrogen atmosphere at a room temperature, 0.62 g (1.8 mmol) of 4-t-butyl-5-(4-bromo-3-methoxyphenyl)-3,3-dimethyl-2,3-dihydrofuran (Compound [52]) was added to 5 mL of anhydrous THF and the mixture was stirred for 20 minutes. The temperature was then lowered to −78° C. and the mixture was further stirred for 20 minutes. To this reaction mixture was added 1.2 mL (1.8 mmol, 1 equivalent) of butyllithium, and the mixture was stirred for 25 minutes. Dry ice was put in the reaction system, which was then allowed to cool spontaneously to room temperature. This reaction mixture was poured in a mixture of ethyl acetate and saturated aqueous solution of sodium chloride and extracted. The organic layer was washed with saturated aqueous solution of sodium chloride, dried with magnesium sulfate anhydride, and concentrated. This concentrate was applied to a silica gel column and the elution was carried out with the mixture of hexane and ethyl acetate (hexane:ethyl acetate=1:1) to obtain 0.21 g (0.68 mmol) of 4-t-butyl-5-(4-carboxy-3-methoxyphenyl)-3,3-dimethyl-2,3-dihydrofuran (Compound [53]) as white solid. Yield 38%.

Recrystallization from the mixture of hexane and ethyl acetate gave white needle crystal.

$^1$HNMR(400 MHz, CDCl$_3$); δ1.07(s, 9H), 1.35(s, 6H), 3.90 (s, 2H), 4.09(s, 3H), 6.99(d, J=1.3 Hz, 1H), 7.11(dd, J=7.8 and 1.3 Hz, 1H), 8.15(d, J=7.8 Hz, 1H) ppm IR (KBr); 3570, 2955, 2867, 2666, 1690, 1604, 1462, 1400, 1308, 1230, 1055, 1036, 864, 811 cm$^{-1}$ Mass (m/z, %); 304(M$^+$, 19), 289(100), 287(6), 179(41), 151(7), 136(4), 105(8), 77(7), 55(37)

Reference Example 41

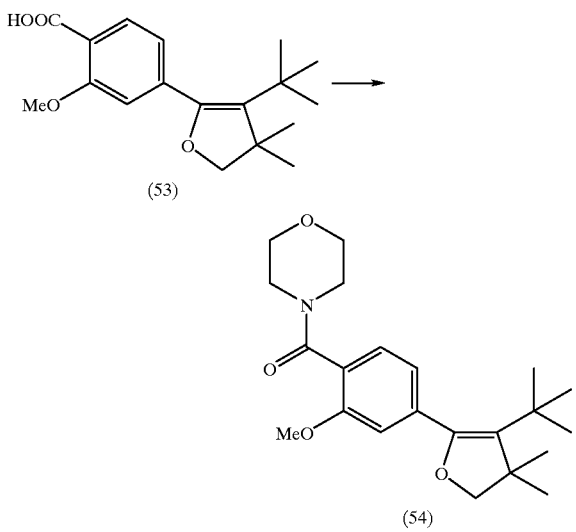

In nitrogen atmosphere at a room temperature, 203 mg (0.67 mmol) of 4-t-butyl-5-(4-carboxyl-3-methoxyphenyl)-3,3-dimethyl-2,3-dihydrofuran (Compound [53]) was added to 3 mL of anhydrous THF and the mixture was stirred for 10 minutes. To this reaction mixture was added 0.18 mL (2.1 mmol) of morpholine, and the mixture was stirred for another 2 hours. This reaction mixture was poured in a mixture of ethyl acetate and saturated aqueous solution of sodium chloride and extracted. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=1:1) to obtain 192 mg (0.51 mmol) of 4-t-butyl-5-(3-methoxy-4-(morpholinocarbonyl)phenyl)-3,3-dimethyl-2,3-dihydrofuran (Compound [54]) as colorless oil. Yield 77%.

$^1$HNMR(400 MHz, CDCl$_3$); δ1.06(s, 9H), 1.54(s, 6H), 3.20–3.25(m, 2H), 3.53–3.60 (m, 2H), 3.73–3.85(m, 6H), 3.88(s, 2H), 6.84(d, J=1.3 Hz, 1H), 6.96(dd, J=1.3 and 7.6 Hz, 1H), 7.21 (d, J=7.6 Hz, 1H) ppm IR (liquid film); 2958, 2863, 1738, 1639, 1604, 1460, 1433, 1245, 1114, 1050, 1014, 833 cm$^{-1}$ Mass (m/z, %); 373(M$^+$, 27), 358(100), 302(13), 287(10), 215(24), 187(4), 55(16)

Reference Example 42

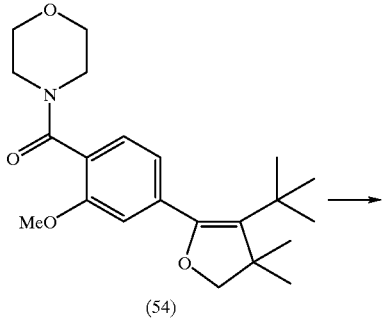

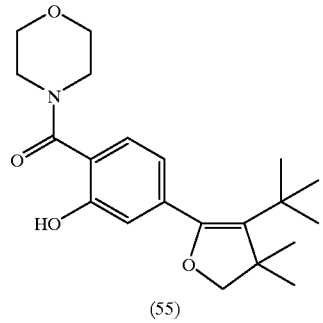

In nitrogen atmosphere at a room temperature, 187 mg (0.54 mmol) of 4-t-butyl-5-(3-methoxy-4-(morpholinocarbonyl)phenyl)-3,3-dimethyl-2,3-dihydrofuran (Compound [54]) was added to 3 mL of anhydrous DMF, followed by stirring for 10 minutes. To this mixture was added 0.26 mg (6.1 mmol, 11 equivalent) of lithium chloride, and the mixture was stirred at 165° C. for 2 hours and, then, at 185° C. for 18 hours. After cooling to room temperature, the reaction mixture was poured in a mixture of ethyl acetate and saturated aqueous solution of sodium chloride and extracted. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=1:1) to obtain 90.7 mg (0.25 mmol) of 4-t-butyl-5-(3-hydroxy-4-morpholinocarbonylphenyl)-3,3-dimethyl-2,3-dihydrofuran (Compound [55]) as white solid. Yield 50%.

Melting point; 141.0 to 141.5° C. (white granular crystals obtained by recrystallization from the mixture of methylene chloride and hexane)

$^1$HNMR(400 MHz, CDCl$_3$); δ1.07(s, 9H), 1.32(s, 6H), 3.71–3.78(m, 8H), 6.81(dd, J=8.1 and 1.5 Hz, 1H), 6.98(d, J=1.5 Hz, 1H), 7.19 (d, J=8.1 Hz, 1H) ppm IR (KBr); 3428, 3083, 2958, 2925, 2857, 1598, 1473, 1414, 1308, 1259, 1115, 1018, 824 cm$^{-1}$ Mass (m/z, %); 359(M$^+$, 23), 344(100), 288(32), 273(4), 201(33), 173(5), 119(10), 77(4), 55(19)

Example 7

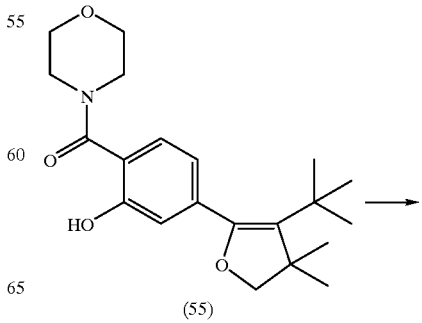

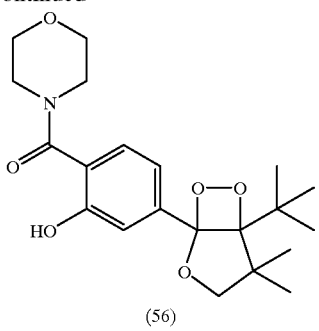

(56)

To 5 mL of methylene chloride were added 0.8 mg (1.3×10$^{-3}$ mmol, 0.02 equivalent) of TPP and 28.3 mg (7.87×10$^{-2}$ mmol) of 4-t-butyl-5-(3-hydroxy-morpholinocarboxylphenyl)-3,3-dimethyl-2,3-dihydrofuran (Compound [55]),and the mixture was stirred in an oxygen atmosphere at 0° C. for 1 hour. This reaction mixture was then concentrated. The residue was applied to a silica gel column and the elution was carried out with the mixture of hexane and ethyl acetate (hexane:ethyl acetate=1:1) to obtain 64.8 mg (6.5×10$^{-2}$ mmol) of 5-t-butyl-1-(3-hydroxy-4-(morpholinocarbonyl)phenyl)-4,4-dimethyl-2,6,7-trioxabicyclo[3.2.0]heptane (Compound [56]) as white solid. Yield 83%.

Melting point; 114.5 to 115.5° C. (white needles crystal obtained by recrystallization from the mixture of methylene chloride and hexane)

$^1$HNMR(400 MHz, CDCl$_3$); δ1.01(s, 9H), 1.15(s, 3H), 1.37 (s, 3H), 3.74(s, 8H), 3.82(d, J=8.3 Hz, 1H), 4.57(d, J=8.3 Hz, 1H), 7.15(dd, J=8.3 and 1.5 Hz, 1H), 7.25 (d, J=8.3 Hz, 1H), 7.29 (d, J=1.5 Hz, 1H) ppm $^{13}$CNMR(100 MHz, CDCl$_3$); δ18.4, 25.0, 26.9, 36.8, 45.6, 46.2,66.8, 76.7, 77.0, 77.3, 80.4, 105.3, 116.0, 117.4, 118.5, 118.6, 127.7, 140.9, 158.8, 170.3 ppm IR (KBr); 3498, 3434, 2979, 2897, 2856, 1622, 1589, 1415, 1282, 1113, 1007 cm$^{-1}$ Mass (m/z, %); 359(M$^+$-32, 6), 344(4), 248(9), 234(27), 207(23), 151(4), 123(11), 86(8), 79(9), 77(11), 55(100)

Reference Example 43

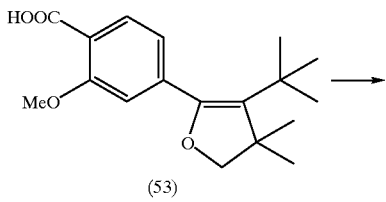

(53)

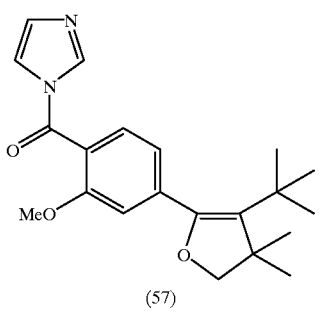

(57)

In nitrogen atmosphere at a room temperature, 146 mg (0.480 mmol) of 4-t-butyl-5-(carboxy-3-methoxyphenyl)-3, 3-dimethyl-2,3-dihydrofuran (Compound [53]) was added to 3 mL of anhydrous THF, followed by addition of 91 mg (0.565 mmol) of carbonyldiimidazole, and the mixture was stirred for 80 minutes. This reaction mixture was poured insaturated aqueous solution of sodium chloride and extracted with ethyl acetate. The extract was washed with saturated aqueous solution of sodium chloride, dried with magnesium sulfate anhydride, and concentrated. This concentrate was applied to a silica gel column and the elution was carried out with the mixture of hexane and ethyl acetate (hexane:ethyl acetate=1:1) to obtain 104 mg of 4-t-butyl-5-((4-imidazol-1-ylcarbonyl)-3-methoxyphenyl)-3,3-dimethyl-2,3-dihydrofuran (Compound [57]). Yield 61.2%.

$^1$HNMR(CDCl$_3$, 90 MHz); δ1.09(s, 9H), 1.36(s, 6H), 3.82 (s, 3H), 3.92(s, 2H), 6.95–7.13(m, 3H), 7.37–7.50(m, 2H), 7.87(broad s, 1H) ppm Reference Example 44

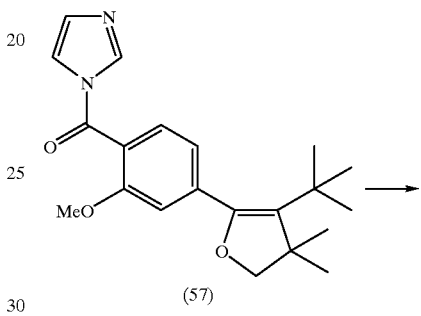

(57)

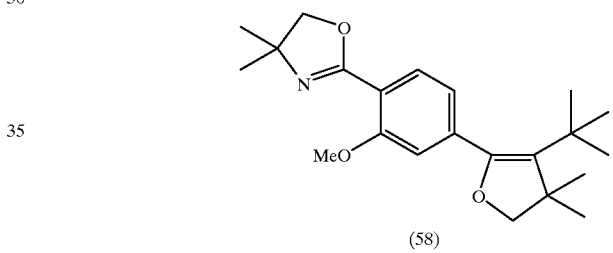

(58)

In nitrogen atmosphere at a room temperature, 104 mg (0.308 mmol) of 4-t-butyl-5-((4-imidazol-1-ylcarbonyl)-3-methoxyphenyl)-3,3-dimethyl-2,3-dihydrofuran (Compound [57]), 51 mg (0.572 mmol) of 2,2-dimethylaminoethanol and 107 mg (0.953 mmol) of potassium carbonate were added to 2 mL of anhydrous DMF and the mixture was stirred overnight. This reaction mixture was poured in saturated aqueous solution of sodium chloride and extracted with ethyl acetate. The extract was washed with saturated aqueous solution of sodium chloride, dried with magnesium sulfate anhydride, and concentrated. In nitrogen atmosphere at a room temperature, 0.25 mL (3.09 mmol) of pyridine and 0.090 mL (1.23 mmol) of thionyl chloride were serially added to solution of the concentrate obtained above in 2 mL of anhydrous dichloromethane, and the mixture was stirred overnight. This reaction mixture was poured in aqueous solution of sodium hydrogen carbonate and extracted with ethyl acetate. The extract was washed with saturated aqueous solution of sodium chloride, dried with magnesium sulfate anhydride, and concentrated. The concentrate was applied to a silica gel column and the elution was carried out with the mixture of hexane and ethyl acetate (hexane:ethyl acetate=1:1) to obtain 25 mg of 4-t-butyl-5-(3-methoxy-4-(4,4-dimethyl-4,5-dihydrooxazol-1-yl) phenyl)-3,3-dimethyl-2,3 -dihydrofuran (Compound [58]) as colorless oil. Yield 22.7%.

¹HNMR(400 MHz, CDCl₃); δ1.04(s, 9H), 1.34(s, 6H), 1.39 (s, 6H), 3.89(s, 2H), 3.89(s, 3H), 4.09(s, 2H), 6.87(d, J=1.4 Hz, 1H), 6.92(dd, J=7.8 and 1.4 Hz, 1H), 7.70(d, J=7.8 Hz, 1H) ppm Reference Example 45

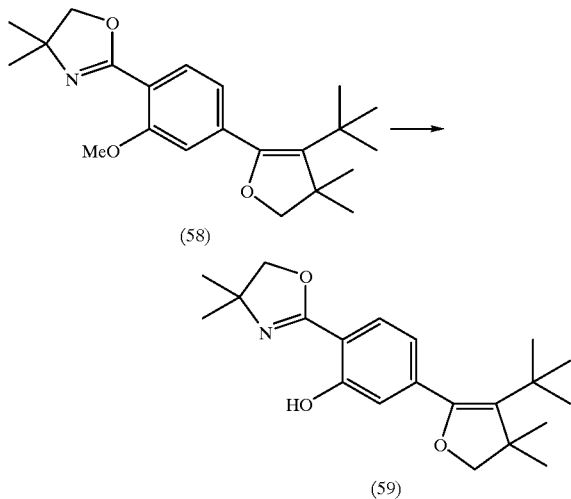

In nitrogen atmosphere, 422 mg (1.24 mmol) of 4-t-butyl-5-(3-methoxy-4-(4,4-dimethyl-4,5-dihydrooxazol-1-yl)phenyl)-3,3-dimethyl-2,3-dihydrofuran (Compound [58]) and 522 mg (12.3 mmol) of lithium chloride were added to 5 mL of anhydrous DMF and the mixture was refluxed for 2 hours. This reaction mixture was poured in water and extracted with ethyl acetate. The extract was washed with saturated aqueous solution of sodium chloride, dried with magnesium sulfate anhydride, and concentrated. The concentrate was applied to a silica gel column and the elution was carried out with the mixture of hexane and ethyl acetate (hexane:ethyl acetate=1:2) to obtain 387 mg of 4-t-butyl-5-(3-hydroxy-4-(4,4-dimethyl-4,5-dihydrooxazol-1-yl)phenyl)-3,3-dimethyl-2,3-dihydrofuran (Compound [59]). Yield 92.2%.

Melting point; 105.0 to 106.0° C. (colorless granular crystals obtained by recrystallization from ethyl acetate)

¹HNMR(400 MHz, CDCl₃); δ1.06(s, 9H), 1.32(s, 6H), 1.39 (s, 6H), 3.87(s, 2H), 4.09(s, 2H), 6.81(dd, J=8.0 and 1.5 Hz, 1H), 6.96(d, J=1.5 Hz, 1H), 7.58(d, J=8.0 Hz, 1H), 12.18 (broad s, 1H) ppm Example 8

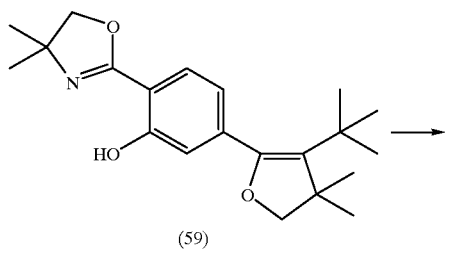

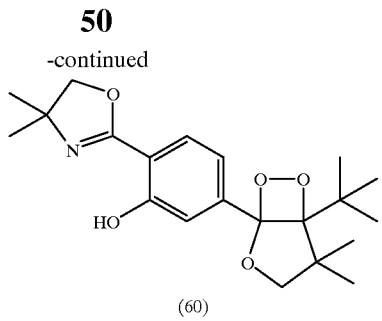

In 15 mL of dichloromethane were dissolved 49 mg (0.14 mmol) of 4-t-butyl-5-(3-hydroxy-4-(4,4-dimethyl-4,5-dihydrooxazol-1-yl)phenyl)-3,3-dimethyl-2,3-dihydrofuran (Compound [59]) and 1 mg of TPP, and the mixture was stirred in an oxygen atmosphere at −78° C. This reaction mixture was externally irradiated with a 940 W sodium lamp for 30 minutes, and then the resulting mixture was concentrated. The concentrate was applied to a silica gel column and the elution was carried out with dichloromethane and the mixture of dichloromethane and ethyl acetate (dichloromethane:ethyl acetate=3:1) in that order. As a result, 50.2 mg of 5-t-butyl-1-(3-hydroxy-4-(4,4-dimethyl-4,5-dihydrooxazol-1-yl)phenyl)-4,4-dimethyl-2,6,7-trioxabicyclo[3.2.0]heptane (Compound [60]) was obtained. Yield 93.6%.

Melting point; 141.5 to 143.0° C. (colorless granular crystals obtained by recrystallization from methanol)

¹HNMR(CDCl₃, 400 MHz); δ1.00(s, 9H), 1.15(s, 3H), 1.38 (s, 3H), 1.41(s, 6H), 4.20(q$_{AB}$, J=8.3 Hz, 2H), 4.11(s, 2H), 7.15(dd, J=7.8 and 2.0 Hz, 1H), 7.28(d, J=2.0 Hz, 1H), 7.64(d, J=7.8 Hz, 1H), 12.21(broad s, 1H) ppm
¹³CNMR(CDCl₃, 100 MHz); δ18.4, 25.0, 26.9, 28.5, 36.8, 45.6, 67.3, 78.5, 80.4, 105.3, 111.7, 116.2, 116.9, 118.5, 127.4, 141.0, 159.3, 163.1 ppm Reference Example 46

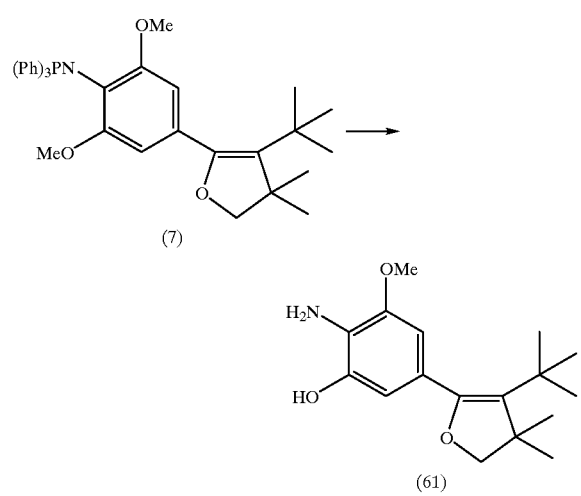

In nitrogen atmosphere at 0° C. , 6.0 mL (80.1 mmol) of ethanethiol was added to 75 mL of DMF dissolving 2.82 mg (70.5 mmol) of 60% sodium hydride. Adding 6.49 g (11.5 mmol) of 4-t-butyl-5-(3,5-dimethoxy-4-triphenylphosphorous-iminophenyl)-3,3-dimethyl-2,3-dihydrofuran (Compound [7]), the mixture was refluxed for 2 hours at 160° C. The mixture was refluxed for 2 hours at 180° C. This reaction mixture was poured in saturated aqueous solution of ammonium chloride and extracted with ethyl acetate. The extract was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=3:1) to provide 1.12 g of 5-(4-amino-3-hydroxy-5-methoxyphenyl)-4-t-butyl-3,3-dimethyl-2,3-dihydrofuran (Compound [61]) as a yellow needle crystal. Yield 33.5%.

Melting point: 134.0° C.–134.3° C.

$^1$HNMR(400 MHz, CDCl$_3$); δ1.07(s, 9H),1.31(s, 6H), 3.50–3.80(Br, 2H), 3.84(s, 3H), 3.84(s, 2H), 4.60–5.10 (Br, 1H), 6.40 (s, 2H) ppm IR(KBr); 3391, 3360, 2953, 1650, 1602, 1342, 1074 cm$^{-1}$ Reference Example 47

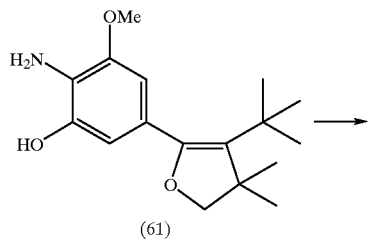

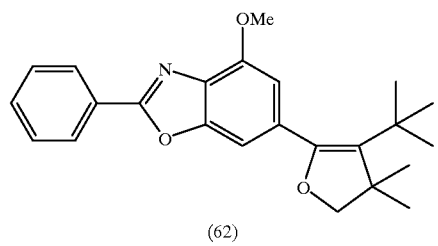

To 1.00 mL (5.82 mmol) of trimethyl orthobenzoate was added 204 mg (0.70 mmol) of 5-(4-amino-3-hydroxy-5-methoxyphenyl)-4-t-butyl-3,3-dimethyl-2,3-dihydrofuran (Compound [61]), and the mixture was refluxed for 1.5 hours at 150° C. To this reaction mixture, 2.0 ml of ethyl acetate, and 0.2 ml of H$_2$O, and 10.1 mg (0.05 mmol) of TsOH H$_2$O was added and the mixture was refluxed for 1 hours at 97° C. The resulting mixture was poured in saturated aqueous solution of sodium hydrogencarbonate and extracted with ethyl acetate. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=10:1) to obtain 207 mg of 4-t-butyl-5-(4-methoxy-2-phenylbenzo[d]oxazol-6-yl)-3,3-dimethyl-2,3-dihydrofuran (Compound [62]). Yield 78.4%.

Melting point: 68.5° C.–69.0° C. (colorless needle crystal obtained by recrystallization from hexane)

$^1$HNMR(400 MHz, CDCl$_3$); δ1.09(s, 9H), 1.37 (s, 6H), 3.92 (s, 2H), 4.07 (s, 3H), 6.75 (d, J=1.0 Hz, 1H), 7.17(d, J=1.0 Hz, 1H), 7.50–7.52(m, 3H), 8.27–8.30(m, 2H) ppm IR (KBr); 2953, 1614, 1486, 1272, 1115 cm$^{-1}$ Reference Example 48

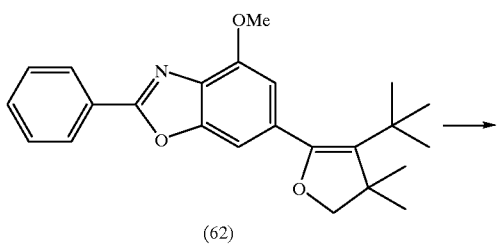

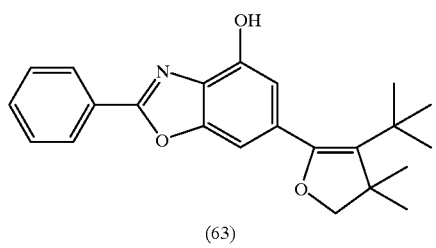

In nitrogen atmosphere at 0° C., 0.25 mL of ethanethiol was added to 3 mL of DMF dissolving 104 mg (2.6 mmol) of 60% sodium hydride. Adding 505 mg (1.3 mmol) of 4-t-butyl-5-(4-methoxy-2-phenylbenzo[d]oxazol-6-yl)-3,3-dimethyl-2,3-dihydrofuran (Compound [62]), the mixture was refluxed for 1.0 hours at 155° C. The resulting mixture was poured in pure water and extracted with ethyl acetate. The organic layer was washed with saturated aqueous solution of sodium chloride, dried with magnesium sulfate anhydride, and concentrated. The concentrate was applied to a silica gel column and the elution was carried out with the mixture of hexane and ethyl acetate (hexane:ethyl acetate= 5:1) to obtain 410 mg of 4-t-butyl-5-(4-hydroxy-2-phenylbenzo[d]oxazol-6-yl)-3,3-dimethyl-2,3-dihydrofuran (Compound [63]). Yield 82.8%.

Melting point: 160.5° C.–161.1° C. (colorless needle microcrystal obtained by recrystallization from hexane)

$^1$HNMR(400 MHz, CDCl$_3$); δ1.09(s, 9H), 1.36 (s, 6H), 3.90 (s, 2H), 6.86 (broad s, 1H), 7.12 (d, J=1.0 Hz, 1H), 7.18(s, 1H), 7.49–7.53(m, 3H), 8.19–8.21(m, 2H) ppm IR (KBr); 3065, 2961, 1619, 1481, 1312, 1056 cm$^{-1}$ Example 9

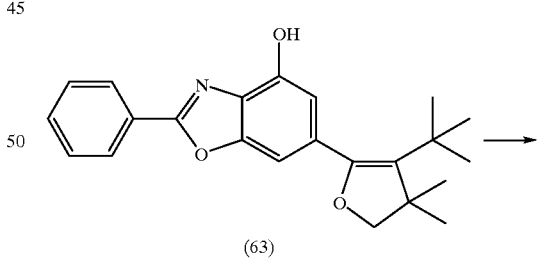

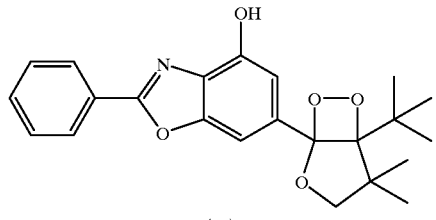

To 15 mL of methylene chloride were added 1.0 mg of TPP and 156 mg (0.43 mmol) of 4-t-butyl-5-(4-hydroxy-2- phenylbenzo[d]oxazol-6-yl)-3,3-dimethyl-2,3-dihydrofuran (Compound [63]), and the mixture was externally irradiated with a 940 W sodium lamp in an oxygen atmosphere for 30 minutes, then concentrated. The concentrate was applied to a silica gel column and the elution was carried out with the mixture of hexane and ethyl acetate (hexane:ether =1:1) to obtain 25.3 mg of 5-t-butyl-1-(4-hydroxy-2-phenylbenzo[d]oxazol-6-yl)-4,4-dimethyl-2,6,7-trioxabicyclo[3.2.0]heptane (Compound [64]) as colorless granular crystal. Yield 85.1%.

$^1$HNMR(400 MHz, CDCl$_3$); δ1.03(s, 9H), 1.18(s, 3H), 1.42 (s, 3H), 4.23 (q$_{AB}$, J=8.5 Hz, 2H), 6.77(s, 1H), 7.16(d, J=1.5 Hz, 1H), 7.51–7.56(m, 4H), 8.20–8.23 (m, 2H) ppm IR (KBr); 3395, 2967, 1619, 1489, 1319, 1279, 1112 cm$^{-1}$ Reference Example 49

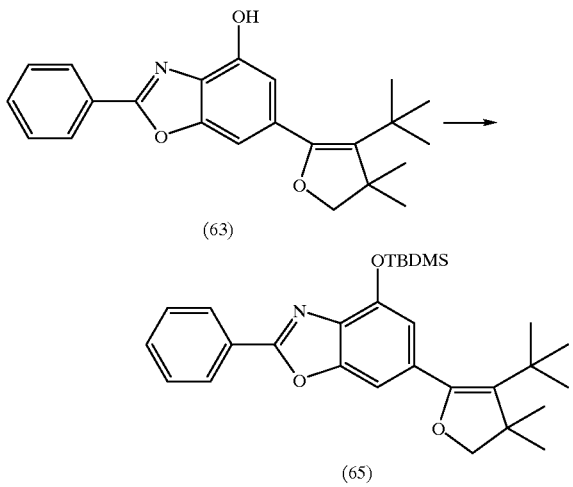

In nitrogen atmosphere at a room temperature, adding 43 mg (0.63 mmol) of imidazole and 64 mg (0.42 mmol) of TBDMSCl to 2.0 ml of DMF dissolving 102 mg (0.28 mmol) of 4-t-butyl-5-(4-hydroxy-2-phenylbenzo[d]oxazol-6-yl)-3,3-dimethyl-2,3-dihydrofuran (Compound [63]), the mixture was stirred for 2 hours. The mixture was added to saturated aqueous solution of sodium chloride and extracted with ethyl acetate. The organic layer was washed with saturated aqueous solution of sodium chloride, then dried with magnesium sulfate anhydride and concentrated. The concentrate was applied to a silica gel column and the elution was carried out with the mixture of hexane and ethyl acetate (hexane:ethyl acetate=7:1) to obtain 108 mg of 4-t-butyl-5-[4-(t-butyldimethylsiloxy)-2-phenylbenzo[d]oxazol-6-yl]-3,3-dimethyl-2,3-dihydrofuran (Compound [65]) as a colorless oil. Yield 80.6%

$^1$HNMR(400 MHz, CDCl$_3$); δ0.32 (s, 6H), 1.07 (s, 9H), 1.35 (s, 6H), 3.90(s, 2H), 6.76 (d, J=1.5 Hz, 1H), 7.14 (d, J=1.5 Hz, 1H), 7.50–7.51 (m, 3H), 8.22–8.24 (m, 2H) ppm $^{13}$CNMR(100 MHz, CDCl$_3$); δ–4.2, 18.5, 25.8, 27.4, 31.3, 32.5, 47.2, 76.7, 77.0, 77.3, 83.2, 105.5, 115.4, 117.8, 125.9, 127.4, 127.5, 128.8, 131.2, 133.6, 134.1, 147.1, 149.5, 151.9, 161.9 ppm IR (liquid film); 2954, 1616, 1481, 1274, 1103, 843 cm$^{-1}$ Example 10

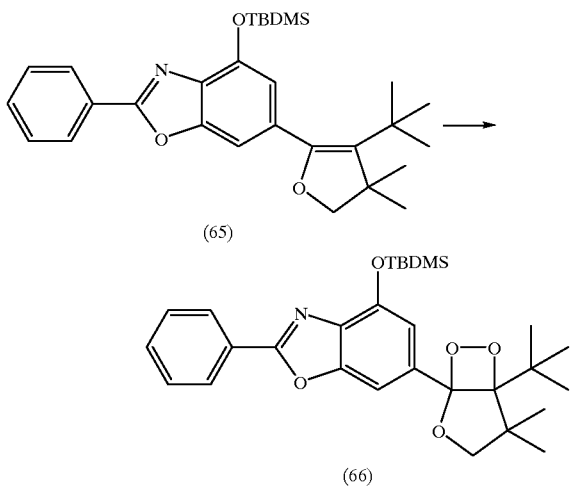

Adding 1 mg of TPP and 27.9 mg (0.058 mmol) of 4-t-butyl-5-[4-(t-butyldimethylsiloxy)-2-phenylbenzo[d]oxazol-6-yl]-3,3-dimethyl-2,3-dihydrofuran (Compound [65]) to 5 ml of methylene chloride, the mixture was externally irritated with a 940 W sodium lamp for 30 minutes in oxygen atmosphere. After concentrated, the resulting mixture was applied to a silica gel column and the elution was carried out the mixture of hexane and ethyl acetate (hexane:ethyl acetate=15:1) to obtain 25.3 mg of 5-t-butyl-1-[4-(t-butyldimethylsiloxy)-2-phenylbenzo[d]oxazol-6-yl]-4,4-dimethyl-2,6,7-trioxabicyclo[3.2.0]heptane (Compound [66]) as a purple oil. Yield 85.1%.

$^1$HNMR(400 MHz, CDCl$_3$); δ0.31 (s, 3H), 0.32 (s, 3H), 1.02 (s, 9H), 1.07 (s, 9H), 1.18 (s, 3H), 1.41 (s, 3H), 4.23 (q$_{AB}$, J=8.2 Hz, 2H), 7.10 (broad s, 1H), 7.51 (d, J=2.0 Hz, 1H), 7.52–7.53 (m, 3H), 8.23–8.25 (m, 2H) ppm IR (liquid film); 2958, 1618, 1489, 1318, 1280, 1108, 843 cm$^{-1}$ Reference Example 50

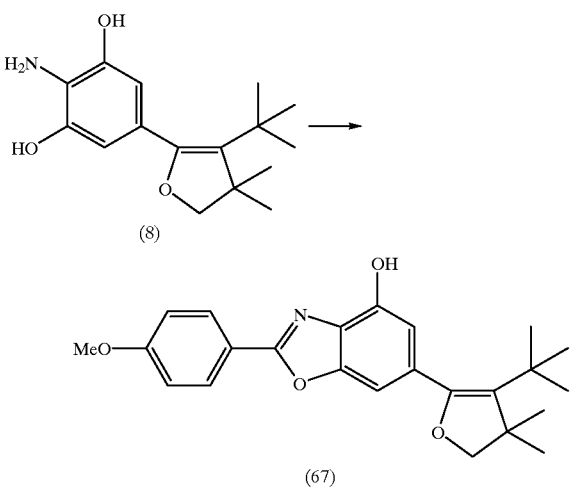

In nitrogen atmosphere at a room temperature, to 310 mg (1.46 mmol) of trimethyl 4-methoxy-1-orthobenzoate was added 1 ml of ethyleneurea dissolving 133 mg (0.48 mmol) of 5-(4-amino-3,5-dihydrophenyl)-4-t-butyl-3,3-dimethyl-2, 3-dihydrofuran (Compound [8]), and the mixture was heated for 1.0 hours at 150° C. The resulting mixture was poured in saturated aqueous solution of sodium chloride and extracted with ethyl acetate. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane: ethyl acetate=3:1), and then followed by recrystallization from the mixture of methylene chloride and hexane to obtain 155 mg of 4-t-butyl-5-(4-hydroxy-2-(p-methoxyphenyl)benzo[d]-oxazol-6-yl)-3,3-dimethyl-2,3-dihydrofuran (Compound [67]) as a colorless granular micro-crystal. Yield 81.9%.

$^1$HNMR(400 MHz, CDCl$_3$); δ1.08(s, 9H), 1.35 (s, 6H), 3.89 (s, 6H), 6.49 (s, 1H), 6.82(s, 1H), 7.02(d, J=8.8 Hz, 2H), 7.08(s, 1H), 8.14(d, J=8.8 Hz,2H) ppm IR (KBr):2295, 2958, 1615, 1497, 1314, 1261, 1085 cm$^{-1}$

Example 11

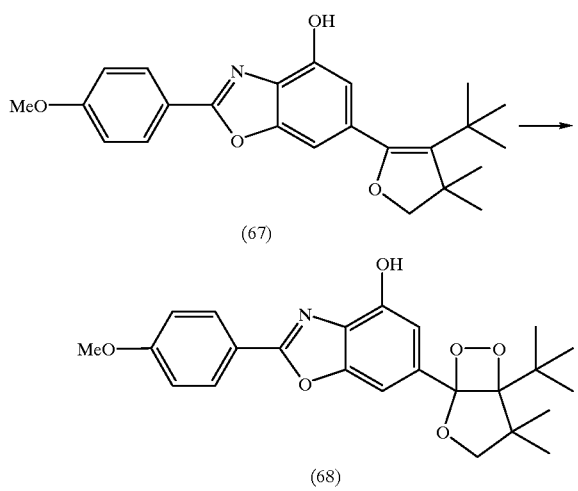

To 5 mL of methylene chloride were added 1.0 mg of TPP and 95.1 mg (0.24 mmol) of 4-t-butyl-5-(4-hydroxy-2-(p-methoxyphenyl)benzo[d]oxazol-6-yl)-3,3-dimethyl-2,3-dihydrofuran (Compound [67]), and the mixture was externally irradiated with a 940 W sodium lamp in an oxygen atmosphere for30 minutes. After the resulting mixture was concentrated, the concentrate was applied to a silica gel column and the elution was carried out with the mixture of hexane and ethyl acetate (hexane:ethyl acetate=3:1), and then followed by recrystallization from the mixture of methylene chloride and hexane to obtain 95.8 mg of 5-t-butyl-1-(4-hydroxy-2-(p-methoxyphenyl)benzo[d]oxazol-6-yl)-4,4-dimethyl-2,6,7-trioxabicyclo[3.2.0]heptane (Compound [68]) as colorless granular micro-crystal. Yield 93.1%.

$^1$HNMR(400 MHz, CDCl$_3$); δ1.03(s, 9H), 1.18(s, 3H), 1.41 (s, 3H), 4.20(q$_{AB}$, J=8.3 Hz, 2H), 3.89(s, 3H), 6.99–7.03(m, 2H), 7.02(d, J=1.0 Hz, 1H), 7.40(s, 1H), 7.49(d, J=1.0 Hz, 1H), 8.13–8.16(m,2H) ppm IR(KBr); 3419, 2968, 1614, 1498, 1314, 1258, 1092 cm$^{-1}$

Reference Example 51

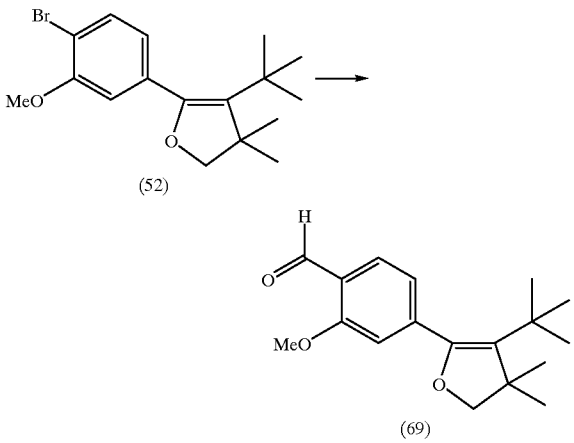

In nitrogen atmosphere at a room temperature, 3.38 g (9.96 mmol) of 4-t-butyl-5-(4-bromo-3,5-methoxyphenyl)-3,3-dimethyl-2,3-dihydrofuran (Compound [52]) was added to 30 ml of THF, and the mixture was stirred for 10 minutes at −78° C. Then, adding 1.4 ml (11.3 mmol) of N-methylformanilide, and the mixture was stirred for 1 hours and then added dropwise a little amount of H$_2$O to finish the reaction. The resulting mixture was poured in 1N hydrogen chloride and extracted with ethyl acetate twice. The organic layer was washed with saturated aqueous solution of sodium hydrocarbonate and then with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=4:1) to obtain 1.94 g (6.73 mmol) of 4-t-butyl-5-(4-formyl-3-methoxyphenyl)-3,3-dimethyl-2,3-dihydrofuran (Compound [69]) as a pale yellow oil. Yield 65.6%.

$^1$HNMR(400 MHz, CDCl$_3$); δ1.07(s, 9H), 1.35(s, 6H), 3.90 (s, 3H), 3.94(s, 2H), 6.92(d, J=1.5 Hz,1H), 6.99(dd, J=7.8and 1.5 Hz, 1H), 7.79(d, J=7.8 Hz, 1H), 10.45(s, 1H) ppm IR (liquid film); 2957, 2866, 1685, 1601, 1567, 1464, 1405, 1314, 1230, 1053 cm$^{-1}$ Mass (m/z, %); 288(M$^+$, 26), 273(100), 217(39), 163(37), 135(16)

Reference Example 52

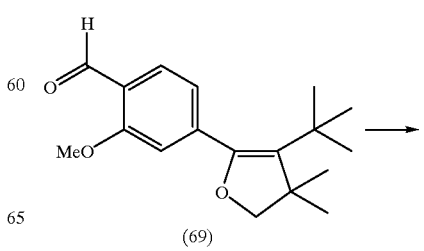

-continued

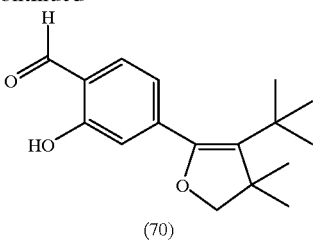

In nitrogen atmosphere at a room temperature, 2.53 g (59.7 mmol) of lithium chloride was added to DMF dissolving 1.7 g (5.89 mmol) of 4-t-butyl-5-(4-formyl-3-methoxyphenyl)-3,3-dimethyl-2,3-dihydrofuran (Compound [69]), and the mixture was refluxed for 10 hours at 170° C. The resulting mixture was poured in saturated aqueous solution of sodium chloride and extracted with ethyl acetate twice. The organic layer was washed with saturated aqueous solution of sodium chloride, dried with magnesium sulfate anhydride, and concentrated. The concentrate was applied to a silica gel column and the elution was carried out with the mixture of hexane and ethyl acetate (hexane:ethyl acetate=4:1) to obtain 1.29 g (4.70 mmol) of 4-t-butyl-5-(4-formyl-3-hydroxyphenyl)-3,3-dimethyl-2,3-dihydrofuran (Compound [70]) as a colorless needle crystal. Yield 79.8%.

$^1$HNMR(400 MHz, CDCl$_3$); δ1.07(s, 9H), 1.33 (s, 6H), 2.63 (s, 3H), 3.88(s, 2H), 6.85(dd, J=8.3 and 1.5 Hz, 1H), 6.94(d, J=1.5 Hz, 1H), 7.69(d, J=8.3 Hz, 1H), 12.24(s, 1H) ppm IR (KBr); 3194, 2955, 2864, 1669, 1616, 1557, 1461, 1383, 1300, 1180, 1055, 821 cm$^{-1}$ Mass (m/z, %); 274(M$^+$, 24), 259(100), 203(44), 149(38), 121(11),77(5),56(16)

Reference Example 53

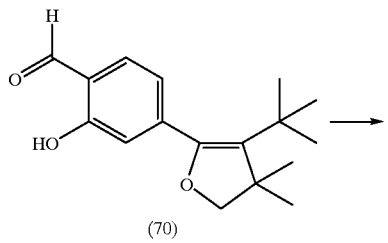

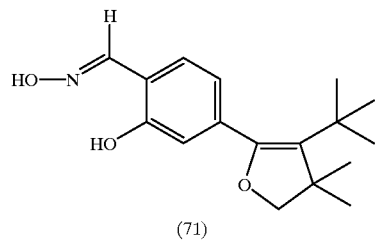

At a room temperature, 255 mg (3.04 mmol) of sodium hydrogencarbonate and 209 mg (3.01 mmol) of hydroxylamine hydrochloride were added to 6.00 ml of ethanol dissolving 545 mg (1.99 mmol) of 4-t-butyl-5-(4-formyl-3-hydroxyphenyl)-3,3-dimethyl-2,3-dihydrofuran (Compound [70]), and the mixture was refluxed for 30 minutes at 90° C. The resulting mixture was poured in saturated aqueous solution of sodium chloride and extracted with ethyl acetate twice. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate= 5:1) to obtain 520 mg (1.80 mmol) of 4-t-butyl-5-[3-hydroxy-(1-hydroxyiminomethyl)phenyl]-3,3-dimethyl-2,3-dihydrofuran (Compound [71]) as a colorless granular crystal. Yield 90.5%.

$^1$HNMR(400 MHz, CDCl$_3$); δ1.07(s, 9H), 1.33(s, 6H), 3.87 (s, 2H), 6.84–6.89(m,1H), 6.92–6.97(m,1H), 7.14(s, J=7.8 Hz, 1H), 7.18(s, 1H), 8.21(s, 1H), 9.71(s, 1H) ppm $^{13}$CNMR(100 MHz, CDCl$_3$); δ27.3, 32.5, 32.5, 47.3, 83.2, 116.2, 118.4, 121.5, 126.5, 130.2, 139.0, 148.8, 152.6, 156.7 ppm IR (KBr); 3352, 2963, 2871, 1621, 1560, 1467, 1365, 1200, 1042, 996, 821 cm$^{-1}$ Example 12

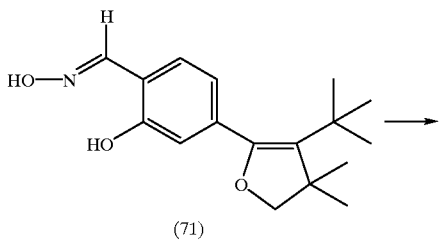

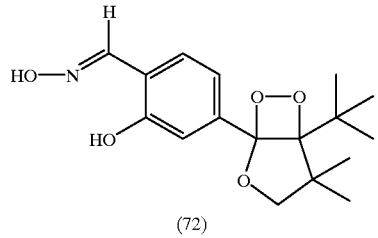

In oxygen atmosphere at 0° C., to 5 mL of methylene chloride dissolving 45.4 mg (0.157 mmol) of 4-t-butyl-5-[3-hydroxy-(1-hydroxyiminomethyl)phenyl]-3,3-dimethyl-2,3-dihydrofuran (Compound [71]) was added 2.1 mg (3.42×10$^{-3}$ mmol) of TPP, and the mixture was externally irradiated with a 940 W sodium lamp and stirred for 1 hours. After the resulting mixture was concentrated, the concentrate was applied to a silica gel column and the elution was carried out with the mixture of hexane and ethyl acetate (hexane:ethyl acetate=5:1) to obtain 47.6 mg (0.148 mmol) of 5-t-butyl-1-[3-hydroxy-4-(1-hydroxyiminomethyl) phenyl]-4,4-dimethyl-2,6,7-trioxabicyclo[3.2.0]heptane (Compound [72]) as colorless granular crystal. Yield 94.3%.

$^1$HNMR(400 MHz, CDCl$_3$); δ1.01(s, 9H), 1.15(s, 3H), 1.37 (s, 3H), 3.82(d, J=8.6 Hz, 1H), 4.58(d, J=8.6 Hz, 1H), 7.19–7.23(m,3H), 7.24–7.27(m,1H), 8.24(s, 1H), 9.76(s, 1H) ppm IR(KBr); 3415, 2971, 1623, 1566, 1467, 1373, 1200, 1033, 1002, 819 cm$^{-1}$

Reference Example 54

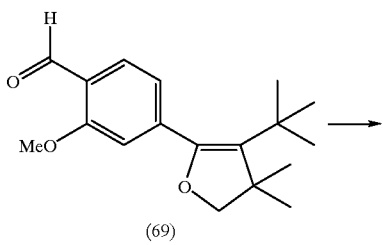

(69)

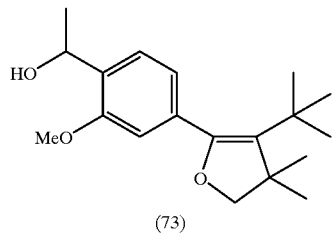

(73)

In nitrogen atmosphere at a room temperature, 1.37 g (4.75 mmol) of 4-t-butyl-5-(4-formyl-3-methoxyphenyl)-3,3-dimethyl-2,3-dihydrofuran (Compound [69]) was added to 15 ml of THF, then 5.10 ml (7.14 mmol) of 1.4 M MeLi in ether was added at −78° C., and the mixture was stirred for 1 hours. The resulting mixture was poured in saturated aqueous solution of sodium chloride and extracted with ethyl acetate twice. The organic layer was washed with saturated aqueous solution of sodium chloride, dried with magnesium sulfate anhydride, and concentrated. The residue was recrystallized from the mixture of methylene chloride and hexane, then the filtrate obtained by recrystallization was applied to a silica gel column and the elution was carried out with the mixture of hexane and ethyl acetate (hexane:ethyl acetate=4:1) to obtain 1.27 g (4.17 mmol) of 4-t-butyl-5-[4-(hydroxyethyl)-3-methoxyphenyl]-3,3-dimethyl-2,3-dihydrofuran (Compound [73]) as a colorless needle crystal. Yield 87.8%.

$^1$HNMR(400 MHz, CDCl$_3$); δ1.06(s, 9H), 1.34(s, 6H), 1.49 (d, J=6.4 Hz,3H), 2.60(d, J=4.9 Hz, 1H), 3.87(s, 3H), 3.87(s, 2H), 5.08(m,1H), 6.79(s, 1H), 6.90(d, J=7.6 Hz, 1H), 7.28(d, J=7.6 Hz, 1H) ppm IR(KBr);3419, 2962, 2870, 1651, 1604, 1461, 1402, 1229, 1129, 1088, 859 cm$^{-1}$ Mass (m/z, %); 304(M$^+$, 5), 303(9), 287(19), 271(100), 177(14),161(69),149(10),135(11),111(23),55(88)

Reference Example 55

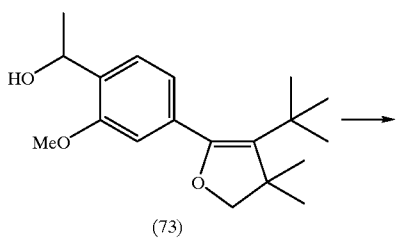

(73)

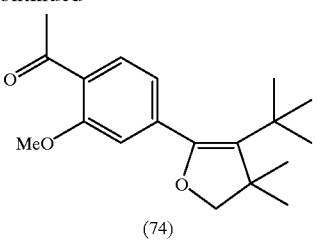

(74)

At a room temperature, 5.11 g (58.8 mmol) of maganese (IV)oxide was added to 10 ml of benzene dissolving 1.03 g (3.38 mmol) of 4-t-butyl-5-[4-(hydroxyethyl)-3-methoxyphenyl]-3,3-dimethyl-2,3-dihydrofuran (Compound [73]), and the mixture was stirred for 30 minutes. Adding 1.91 g (22.0 mmol) of maganese(IV)oxide, the mixture was stirred for 48 hours. Then the resulting mixture was filtrated by Celite and the filtrate was concentrated. The concentrate was applied to a silica gel column and the elution was carried out with the mixture of hexane and ethyl acetate (hexane:ethyl acetate=4:1) to obtain 878 mg (2.90 mmol) of 5-(4-acethyl-3-methoxyphenyl)-4-t-butyl-3,3-dimethyl-2,3-dihydrofuran (Compound [74]) as a colorless oil. Yield 85.6%.

$^1$HNMR(400 MHz, CDCl$_3$); δ1.07(s, 9H), 1.34(s, 6H), 2.61 (d, J=4.9 Hz, 1H), 3.90(s, 2H), 3.92(s, 3H), 6.89(d, J=1.3 Hz, 1H), 6.95(dd, J=7.8 and 1.3 Hz, 1H), 7.70(d, J=7.8 Hz, 1H) ppm IR (liquid film); 2957, 2868, 1676, 1600, 1464, 1401, 1232, 1174, 1052, 833cm$^{-1}$ Mass (m/z, %); 302 (M$^+$, 27), 287(100), 231(40), 203(14), 177(78), 149(9), 135(6), 55(48)

Reference Example 56

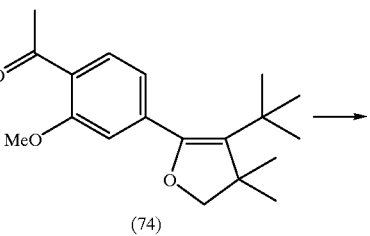

(74)

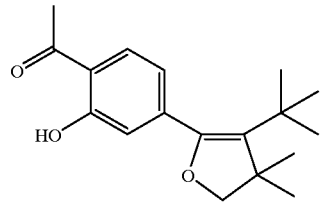

(75)

In nitrogen atmosphere at a room temperature, 214 mg (5.05 mmol) of lithium chloride was added to 1.5 ml of DMF dissolving 152 mg (0.503 mmol) of 5-(4-acethyl-3-methoxyphenyl)-4-t-butyl-3,3-dimethyl-2,3-dihydrofuran (Compound [74]), and the mixture was refluxed for 6.5 hours at 170° C. The resulting mixture was poured in saturated aqueous solution of sodium chloride and extracted with ethyl acetate twice. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=4:1) to obtain 113 mg (0.392 mmol) of 5-(4-acetyl-3-hydroxyphenyl)-4-t-butyl-3,3-dimethyl-2,3-dihydrofuran (Compound [75]) as a brown oil. Yield 77.6%.

$^1$HNMR(400 MHz, CDCl$_3$); δ1.07(s, 9H), 1.33 (s, 6H), 2.63 (s, 3H), 3.88(s, 2H), 6.85(dd, J=8.3and1.5 Hz, 1H), 6.94(d, J=1.5 Hz, 1H), 7.69(d, J=8.3 Hz, 1H), 12.24(s, 1H) ppm IR (liquid film); 3257, 2957, 2826, 1641, 1469, 1366, 1178, 1053, 800 cm$^{-1}$ Mass (m/z, %); 288(M$^+$, 23), 273(100), 257(8), 231(7), 217(51), 201(6), 163(67), 135(8), 55(56)

Reference Example 57

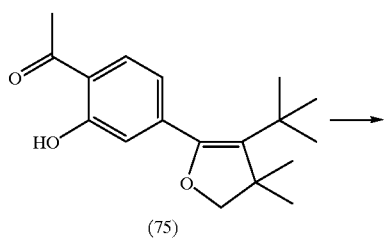

(75)

(76)

At a room temperature, 49.3 mg (0.587 mmol) of sodium hydrogencarbonate and 42.0 mg (0.604 mmol) of hydroxylamine hydrochloride were added to 7.00 ml of ethanol dissolving 113 mg (0.392 mmol) of 5-(4-acetyl-3-hydroxyphenyl)-4-t-butyl-3,3-dimethyl-2,3-dihydrofuran (Compound [75]), and the mixture was refluxed at 100° C. for 1 hour. Then adding 13.7 mg (0.197 mmol) of hydroxylamine hydrochloride, the mixture was refluxed for 15 minutes. The resulting mixture was poured in saturated aqueous solution of sodium chloride and extracted with ethyl acetate twice. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=5:1) to obtain 98.1 mg (0.323 mmol) of 4-t-butyl-5-[3-hydroxy-(1-hydroxyiminoethyl)phenyl]-3,3-dimethyl-2,3-dihydrofuran (Compound [76]) as a colorless needle crystal. Yield 82.5%.

$^1$HNMR(400 MHz, CDCl$_3$); δ1.07(s, 9H), 1.33(s, 6H), 2.35 (s, 3H), 3.87(s, 2H), 6.84(dd, J=8.3 and 1.5 Hz, 1H),6.92(d, J=1.5 Hz, 1H), 7.24(s, 1H), 7.39(d, J=8.3 Hz, 1H), 11.11(s, 1H) ppm $^{13}$CNMR(100 MHz, CDCl$_3$); δ10.8, 27.3, 32.5, 32.5, 47.2, 83.2, 118.3, 118.9, 120.9, 126.2, 127.1, 138.5, 149.0, 157.0, 159.1 ppm IR (KBr); 3316, 2955, 2723, 1618, 1559, 1465, 1176, 1041, 813 cm$^{-1}$ Example 13

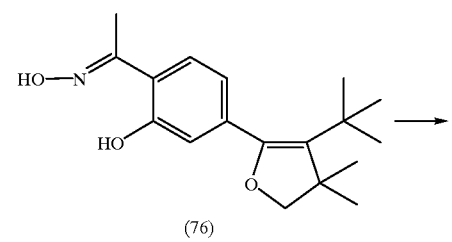

(76)

(77)

In oxygen atmosphere at 0° C. to 5 mL of methylene chloride dissolving 96.8 mg (0.319 mmol) of 4-t-butyl-5-[3-hydroxy-(1-hydroxyiminoethyl)phenyl]-3,3-dimethyl-2,3-dihydrofuran (Compound [76]) was added 1.5 mg (2.44× 10$^{-3}$ mmol) of TPP, and the mixture was externally irradiated with a 940 W sodium lamp and stirred for 1 hours. After the resulting mixture was concentrated, the concentrate was applied to a silica gel column and the elution was carried out with the mixture of hexane and ethyl acetate (hexane:ethyl acetate=5:1) to obtain 92.0 mg (0.274 mmol) of 5-t-butyl-1-[3-hydroxy-4-(1-hydroxyiminomethyl)phenyl]-4,4-dimethyl-2,6,7-trioxa-bicyclo[3.2.0]heptane (Compound [77]) as colorless needle crystal. Yield 85.9%.

$^1$HNMR(400 MHz, CDCl$_3$); δ1.01(s, 9H), 1.15(s, 3H), 1.37 (s, 3H), 2.37(s, 3H), 3.82(d, J=8.1 Hz, 1H), 4.58(d, J=8.1 Hz, 1H), 7.18(dd, J=8.1 and 1.8 Hz, 1H), 7.23(d, J=1.8 Hz, 1H), 7.26(s, 1H), 7.45(d, J=8.1 Hz, 1H), 11.18(s, 1H) ppm $^{13}$CNMR(100 MHz, CDCl$_3$); δ10.9, 18.5, 25.0, 26.9, 36.8, 45.6, 80.3, 105.2, 116.3, 117.5, 119.1, 119.4, 127.2, 138.5, 157.1, 159.2 ppm IR(KBr); 3377, 2978, 2897, 1623, 1570, 1476, 1390, 1218, 1117, 1004, 871 cm$^{-1}$ Reference Example 58

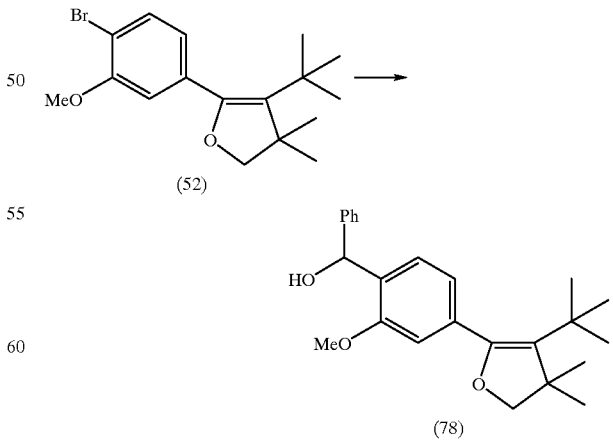

(52)

(78)

In nitrogen atmosphere at a room temperature, 2.05 g (6.04 mmol) of 4-t-butyl-5-(4-bromo-3,5-methoxyphenyl)-

3,3-dimethyl-2,3-dihydrofuran (Compound [52]) was added to 20 mL of THF and the mixture was stirred for 25 minutes at −78° C. To this reaction mixture was added 4.2 mL (6.72 mmol) of 1.6M butyllithium in hexane, and the mixture was stirred for 25 minutes. Adding 0.80 ml (7.87 mmol) of benzaldehyde, the mixture was stirred for 1 hours and then added dropwise a little amount of $H_2O$ to finish the reaction. This reaction mixture was poured in saturated aqueous solution of sodium chloride and extracted with ethyl acetate twice. The organic layer was washed with saturated aqueous solution of sodium chloride, dried with magnesium sulfate anhydride, and concentrated. This concentrate was applied to a silica gel column and the elution was carried out with the mixture of hexane and ethyl acetate (hexane:ethyl acetate=4:1) to obtain 1.49 g (4.07 mmol) of 4-t-butyl-5-[4-(1-hydroxybenzyl)-3-methoxyphenyl]-3,3-dimethy-2,3-dihydrofuran (Compound [78]) as a colorless oil. Yield 67.4%.

$^1$HNMR(400 MHz, CDCl$_3$); δ1.06(s, 9H), 1.33(s, 6H), 2.96 (d, J=5.9 Hz, 1H), 3.80(s, 3H), 3.87(s, 2H), 6.03(d, J=5.9 Hz, 1H), 6.80(d, J=1.5 Hz, 1H), 6.90(dd, J=7.8 and 1.5 Hz, 6H), 7.18–7.38(m,6H) ppm IR (liquid film); 3445, 2956, 1651, 1604, 1459, 1401, 1230, 1048, 794 cm$^{-1}$ Reference Example 59

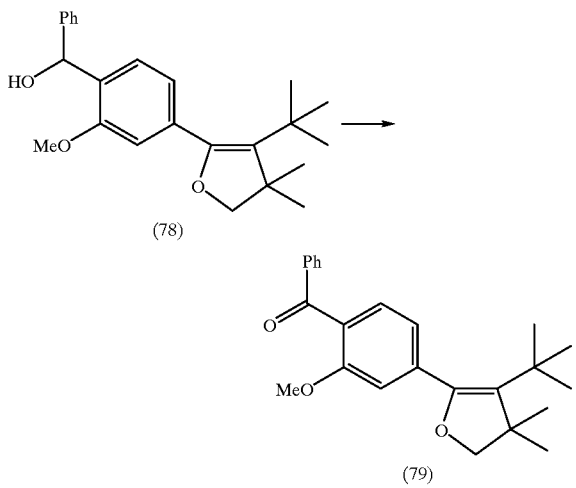

At a room temperature, 7.73 g (88.9 mmol) of maganese (IV)oxide was added to 15 ml of benzene dissolving 1.31 g (3.57 mmol) of 4-t-butyl-5-[4-(1-hydroxybenzyl)-3-methoxyphenyl] -3,3-dimethyl-2,3-dihydrofuran (Compound [78]), and the mixture was stirred for 6 hours. The resulting mixture was filtrated by Celite and the filtrate was concentrated. The concentrate was applied to a silica gel column and the elution was carried out with the mixture of hexane and ethyl acetate (hexane:ethyl acetate=4:1) to obtain 1.05 g (2.88 mmol) of 5-(4-benzoyl-3-methoxyphenyl)-4-t-butyl-3,3-dimethyl-2,3-dihydrofuran (Compound [79]) as a colorless oil. Yield 80.7%.

$^1$HNMR(400 MHz, CDCl$_3$); δ1.01(s, 9H), 1.36(s, 6H), 3.73 (s, 3H), 3.92(s, 2H), 6.92(d, J=1.1 Hz, 1H), 7.00(dd, J=7.7 and 1.1 Hz, 1H), 7.32(d, J=7.7 Hz, 1H), 7.42(t, J=7.8 Hz, 2H), 7.55(t with fine coupling, J=7.8, 1H), 7.80(dd, J=7.8 and 1.5 Hz, 2H) ppm IR (KBr); 2957, 2871, 1657, 1600, 1455, 1399, 1250, 1178, 1048, 836cm$^{-1}$ Reference Example 60

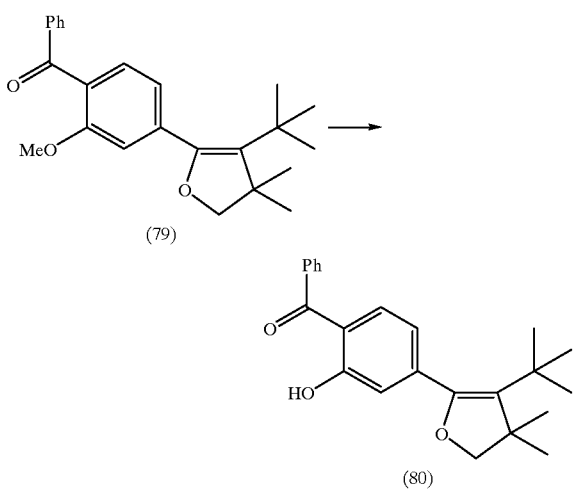

In nitrogen atmosphere at a room temperature, 1.06 g (25.0 mmol) of lithium chloride was added to 10 mL of DMF dissolving 903 mg (2.48 mmol) of 5-(4-benzoyl-3-methoxyphenyl)-4-t-butyl-3,3-dimethyl-2,3-dihydrofuran (Compound [79]), and the mixture was refluxed at 170° C. for 26.5 hours. The reaction mixture was poured in saturated aqueous solution of sodium chloride and extracted with ethyl acetate twice. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=4:1) to obtain 843 mg (2.41 mmol) of 5-(4-benzoyl-3-hydroxyphenyl)-4-t-butyl-3,3-dimethyl-2,3-dihydrofuran (Compound [80]) as a pale yellow oil. Yield 97.2%.

$^1$HNMR(400 MHz, CDCl$_3$); δ1.09(s, 9H), 1.34(s, 6H), 3.89 (s, 2H), 6.82(dd, J=8.1 and 1.6 Hz, 1H), 7.04(d, J=1.6 Hz, 1H), 7.46–7.61(m, 4H), 7.68(d with fine coupling, J=7.68 Hz, 1H), 12.01 (s, 1H) ppm IR (liquid film); 3230, 2958, 2868, 1626, 1575, 1492, 1335, 1221, 1177, 1052, 703 cm$^{-1}$ Reference Example 61

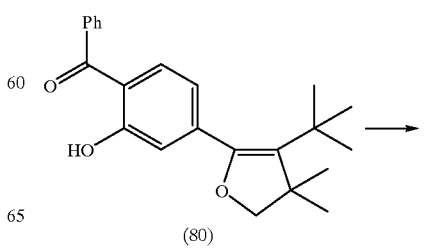

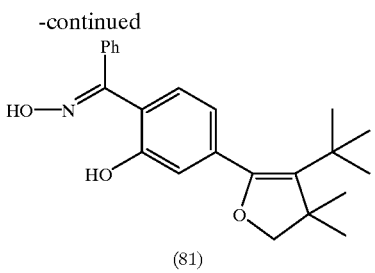

At a room temperature, 248 mg (2.95 mmol) of sodium hydrogencarbonate and 203 mg (2.92 mmol) of hydroxylamine hydrochloride were added to 6.5 ml of ethanol dissolving 673 mg (1.92 mmol) of 5-(4-benzoyl-3-hydroxyphenyl)-4-t-butyl-3,3-dimethyl-2,3-dihydrofuran (Compound [80]), and the mixture was refluxed for 150 minutes at 100° C. The resulting mixture was poured in saturated aqueous solution of sodium chloride and extracted with ethyl acetate twice. The organic layer was washed with saturated aqueous solution of sodium chloride, dried with magnesium sulfate anhydride, and concentrated. The residue was applied to a silica gel column and the elution was carried out with the mixture of hexane and ethyl acetate (hexane:ethyl acetate=4:1) to obtain 340 mg (0.930 mmol) of 4-t-butyl-5-[3-hydroxy-(1-hydroxyiminobenzyl)phenyl]-3,3-dimethyl-2,3-dihydrofuran (Compound [81]) as a colorless granular crystal. Yield 48.4%.
$^1$HNMR(400 MHz, CDCl$_3$); δ1.07(s, 9H), 1.31(s, 6H), 3.85 (s, 2H), 6.68(dd, J=8.3 and 1.5 Hz, 1H), 6.77(d, J=8.3 Hz, 1H), 6.97(d, J=1.5 Hz, 1H), 7.14(s, 1H), 7.33(dd, J=7.6and1.7 Hz,2H), 7.46–7.56(m, 3H), 10.89(s, 1H) ppm
$^{13}$CNMR(100 MHz, CDCl$_3$); δ27.3, 32.5, 32.5, 47.2, 83.1, 118.4, 118.7, 120.7, 126.2, 128.4, 128.5, 129.2, 130.0, 131.0, 138.8, 148.9, 157.4, 161.5 ppm
IR(KBr); 3305, 2956, 2871, 1612, 1561, 1461, 1386, 1224, 1179, 1046, 731 cm$^{-1}$ Example 14

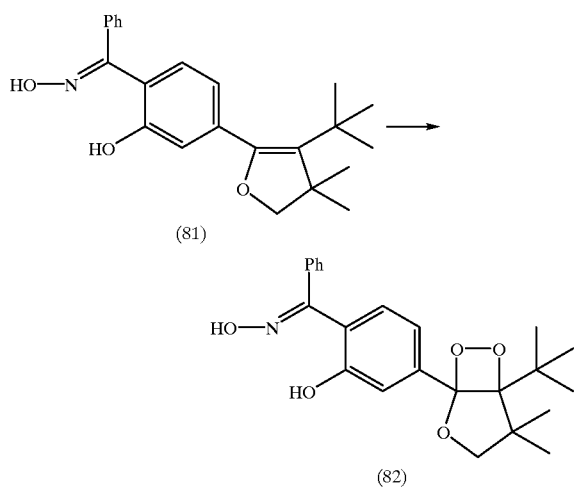

In oxygen atmosphere at 0° C., 1.4 mg (2.28×10$^{-3}$ mmol) of TPP was added to 5 mL of methylene chloride dissolving 108 mg (0.296 mmol) of 4-t-butyl-5-[3-hydroxy-(1-hydroxyiminobenzyl)phenyl]-3,3-dimethyl-2,3-dihydrofuran (Compound 81]), and the mixture was externally irradiated with a 940 W sodium lamp for 1 hours, and then concentrated. The concentrate was applied to a silica gel column and the elution was carried out with the mixture of hexane and ethyl acetate (hexane:ethyl acetate=4:1) to obtain 105 mg (0.264 mmol) of 5-t-butyl-1-[3-hydroxy-4-(1-hydroxyiminobenzyl)phenyl]-4,4-dimethyl-2,6,7-trioxabicyclo[3.2.0]heptane (Compound [82]) as colorless granular crystal. Yield 89.2%.
$^1$HNMR(400 MHz, CDCl$_3$); δ1.01 (s, 9H), 1.14 (s, 3H), 1.35 (s, 3H), 3.79(d, J=8.1 Hz, 1H), 4.56(d, J=8.1 Hz, 1H), 6.85(d, J=8.3 Hz, 1H), 7.02(d, J=8.3 Hz, 1H), 7.12(s, 1H), 7.28–7.35(m, 3H), 7.46–7.58(m, 3H), 10.93(s, 1H) ppm
IR (KBr); 3374, 2973, 1615, 1565, 1391, 1316, 1220, 1037, 1002, 795, 701 cm$^{-1}$ Test Example 1

One milliliter of a 1.00×10$^{-5}$ M 5-t-butyl-4,4-dimethyl-1-(4-hydroxy-benzo[d]oxazol-6-yl)-2,6,7-trioxabicyclo [3.2.0]heptane (Compound [10]) obtained in Example 1 in DMSO was added to 2 ml of 1.00×10$^{-2}$ M tetrabutylammonium fluoride in DMSO at 25° C. and the resulting chemiluminescence was measured with a fluorescence analyzer. The quantum yield of chemiluminescence was estimated to be 0.24, the half-life time was 28 seconds, and λmax was 453 nm.

Test Example 2

The 5-t-butyl-1-(5-(t-butyldimethylsiloxy)-benzofuran-2-yl)-4,4-dimethyl-2,6,7-trioxa-bicyclo[3.2.0]heptane (Compound [19]) obtained in Example 3 was also subjected to the same determinations as in Test Example 1. The λmax of chemiluminescence was 620 nm, the half-life time was 0.19 second, and the quantum yield was estimated to be 1.1×10$^{-3}$.

Test Example 3

The chemiluminescent characteristics of the compounds synthesized in Examples 4 to 6 were also studied by the same procedure as used in Test Example 1. As a result, the λmax, half-life time and estimated quantum yield of 5-t-butyl-1-(5-(t-butyldimethylsiloxy)benzothiophen-2-yl)-4,4-dimethyl-2,6,7-trioxabicyclo[3.2.0]heptane (Compound [26]) were 628 nm, 0.062 second and 7.4×10$^{-3}$, respectively; the corresponding values of 5-t-butyl-1-(5-(t-butyldimethylsiloxy)-3-ethoxybenzofuran-2-yl)-4,4-dimethyl-2,6,7-trioxabicyclo[3.2.0]heptane (Compound [37]) were 620 nm, 0.62 seconds; and the corresponding values of 5-t-butyl-1-(5-(t-butyldimethylsiloxy)-3-ethoxybenzothiophen-2-yl)-4,4-dimethyl-2,6,7-trioxabicyclo[3.2.0]heptane (Compound [46]) were 600 nm, 0.11 second and 4.9×10$^{-2}$.

Test Example 4

One milliliter of a 1.00×10$^{-4}$ M solution of the 5-t-butyl-1-(3-hydroxy-4-(morpholinocarbonyl)phenyl)-4,4-dimethyl-2,6,7-trioxabicyclo[3.2.0]heptane (Compound [56]) obtained in Example 7 in DMSO was added to 2 ml of 1.0×10$^{-1}$ M tetrabutylammonium fluoride in DMSO at 25° C. and the resulting chemiluminescence was measured with a fluorescence analyzer. The quantum yield of chemiluminescence was estimated to be 0.024, the half-life time was 282 seconds and the λmax was 472 nm.

Test Example 5

One milliliter of a 1.00×10$^{-4}$ M 5-t-butyl-1-(3-hydroxy-4-(morpholinocarbonyl)phenyl)-4,4-dimethyl-2,6,7- trioxabicyclo[3.2.0]heptane (Compound [561]) obtained in Example 7 in DMSO was added to 2 ml of 1.00×10$^{-1}$ M sodium hydride in DMSO at 25° C. and the resulting chemiluminescence was measured with a fluorescence analyzer. The quantum yield of chemiluminescence was estimated to be 0.0024, the half-life time was 5990 seconds, and λmax was 472 nm.

Test Example 6

The 5-t-butyl-1-(3-hydroxy-4-(4,4-dimethyl-4,5-dihydrooxazol-1-yl)phenyl)-4,4-dimethyl-2,6,7-trioxabicyclo[3.2.0]heptane (Compound (60]) obtained in Example 8 was subjected to the same determinations as in Test Examples 4 and 5. When the compound was treated with tetrabutylammonium fluoride, the quantum yield of chemiluminescence was estimated to be 0.19, the half-life time was 422 seconds, and the λmax was 482 nm. With sodium hydroxide, the quantum yield of chemiluminescence was estimated to be 0.044, the half-life time was 11300 seconds, and the λmax was 476 nm.

What is claimed is:

1. A 1,2-dioxetane derivative of general formula (I)

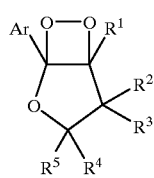

(I)

wherein $R^1$, $R^2$, $R^3$, $R^4$ and $R^5$ each independently represents hydrogen, alkyl or aryl; or wherein $R^2$ and $R^3$ or $R^4$ and $R^5$ may respectively be joined to each other to form a cycloalkyl group;

Ar represents a group of formula (A)

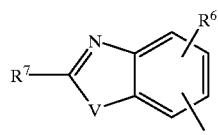

(A)

$R^6$ represents hydroxyl, alkoxyl, aralkyloxy, a phosphate group, or —OSi ($R^8R^9R^{10}$), where $R^8$, $R^9$ and $R^{10}$ each independently represents alkyl; $R^7$ represents hydrogen, alkyl, aryl, hydroxyl, alkoxyl,aryloxy or aralkyloxy; V represents oxygen or sulfur or formula (B)

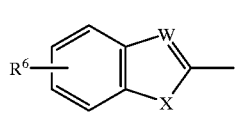

(B)

wherein $R^6$ is the same as in the formula (A); W represents nitrogen or C—$R^{11}$, wherein $R^{11}$ represents hydrogen, alkyl, alkoxyl, aryl or aralkyloxy; X represents oxygen or sulfur, or formula (C)

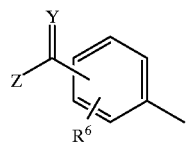

(C)

wherein $R^6$ is the same as in the formula (A); Y represents oxygen, sulfur or N—$R^{12}$; Z represents hydrogen, alkyl, aryl, $OR^{13}$, $SR^{14}$ or a group of the formula;

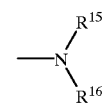

$R^{12}$ represents hydrogen, alkyl, aryl, hydroxyl, or alkoxyl group; $R^{13}$, $R^{14}$, $R^{15}$ and $R^{16}$ each independently represents hydrogen, alkyl or aryl; or wherein $R^{12}$ and $R^{13}$, $R^{12}$ and $R^{14}$, $R^{12}$ and $R^{15}$, or $R^{15}$ and $R^{16}$ may respectively be joined to each other to form a ring, which ring may contain 2 or more hetero-atoms, each independently being nitrogen, oxygen or sulfur.

2. The 1,2-dioxetane derivative according to claim 1 wherein Ar represents a group of formula (a)

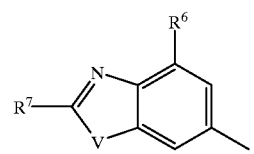

(a)

wherein $R^6$, $R^7$ and V are as defined in the formula (A), formula (b)

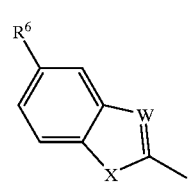

(b)

wherein $R^6$, W and X are as defined in the formula (B), or formula (c)

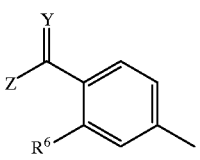

(c)

wherein $R^6$, Y, and Z are as defined in the formula (C).

3. The 1,2-dioxetane derivative according to claim 1 wherein $R^1$, $R^2$, and $R^3$ each represents alkyl and $R^4$ and $R^5$ each represents hydrogen.

4. The 1,2-dioxetane derivative according to claim 3 wherein the alkyl is an alkyl group of 1 to 4 carbon atoms.

5. The 1,2-dioxetane derivative according to claim 1, wherein Y represents oxygen, Z represents a group of the formula

wherein $R^{15}$ and $R^{16}$ are joined to each other to form a 3- through 7-membered ring.

6. The 1,2-dioxetane derivative according to claim 5 wherein $R^{15}$ and $R^{16}$ are joined to each other and Z represents a ring of the formula.

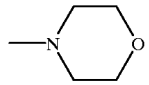

7. The 1,2-dioxetane derivative according to claim 1, wherein Y represents N—$R^{12}$, Z represents $OR^{13}$, and $R^{12}$ and $R^{13}$ are joined to each other to form a 3- through 7-membered ring.

8. The 1,2-dioxetane derivative according to claim 7 wherein $R^{12}$ and $R^{13}$ are joined to each other and (C=Y)—Z is a ring of the formula.

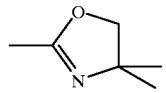

9. An immunological assay kit comprising the 1,2-dioxetane derivative according to claim 1.

10. A method for immunological assays which comprises:
(1) mixing a substance (i) with a sample containing another substance (ii) to be detected, allowing the mixture to react, said substance (i) having a specific binding affinity to the substance (ii), said substance (i) being coupled to an enzyme which is decomposable of the 1,2-dioxetane derivative according to claim 1;
(2) reacting the enzyme with the 1,2-dioxetane derivative; and
(3) measuring the intensity of the chemiluminescence.

11. The 1,2-dioxetane derivative according to claim 2 wherein $R^1$, $R^2$, and $R^3$ each represents alkyl and $R^4$ and $R^5$ each represents hydrogen.

12. The 1,2-dioxetane derivative according to claim 2 wherein Y represents oxygen, Z represents a group of the formula

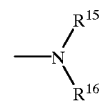

wherein a pair of $R^{15}$ and $R^{16}$ are joined to each other to form a 3- through 7-membered ring.

13. The 1,2-dioxetane derivative according to claim 3 wherein Y represents oxygen, Z represents a group of the formula

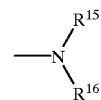

wherein $R^{15}$ and $R^{16}$ are joined to each other to form a 3- through 7-membered ring.

14. The 1,2-dioxetane derivative according to claim 4 wherein Y represents oxygen, Z represents a group of the formula

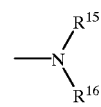

wherein $R^{15}$ and $R^{16}$ are is joined to each other to form a 3- through 7-membered ring.

15. The 1,2-dioxetane derivative according to claim 2 wherein Y represents N—$R^{12}$, Z represents $OR^{13}$, and $R^{12}$ and $R^{13}$ are joined to each other to form a 3- through 7-membered ring.

16. The 1,2-dioxetane derivative according to claim 3 wherein Y represents N—$R^{12}$, Z represents $OR^{13}$, and $R^{12}$ and $R^{13}$ are joined to each other to form a 3- through 7-membered ring.

17. The 1,2-dioxetane derivative according to claim 4 wherein Y represents N—$R^{12}$, Z represents $OR^{13}$, and $R^{12}$ and $R^{13}$ are joined to each other to form a 3- through 7-membered ring.

18. An immunological assay kit comprising the 1,2-dioxetane derivative according to claim 2.

19. An immunological assay kit comprising the 1,2-dioxetane derivative according to claim 3.

20. An immunological assay kit comprising the 1,2-dioxetane derivative according to claim 4.

* * * * *